(12) United States Patent
Tamimi Marino et al.

(10) Patent No.: US 11,629,055 B2
(45) Date of Patent: *Apr. 18, 2023

(54) MAGNESIUM PHOSPHATE HYDROGELS

(71) Applicant: INViCARE INC., Montreal (CA)

(72) Inventors: Faleh Tamimi Marino, Montréal (CA); Ashwaq Ali Al-Hashedi, Montréal (CA); Marco Laurenti, Madrid (ES); Ahmed Ebraheem Al Subaie, Brossard (CA); Mohamed-Nur Abdallah, Paphos (CY); Iskandar Tamimi Marino, Montréal (CA)

(73) Assignee: INVICARE INC., Montréal (CA)

( * ) Notice: Subject to any disclaimer, the term of this patent is extended or adjusted under 35 U.S.C. 154(b) by 301 days.

This patent is subject to a terminal disclaimer.

(21) Appl. No.: 17/111,940

(22) Filed: Dec. 4, 2020

(65) Prior Publication Data

US 2021/0163290 A1 Jun. 3, 2021

Related U.S. Application Data

(63) Continuation of application No. 16/060,462, filed as application No. PCT/CA2016/051415 on Dec. 2, 2016, now Pat. No. 10,875,772.

(60) Provisional application No. 62/265,570, filed on Dec. 10, 2015.

(51) Int. Cl.
| | |
|---|---|
| *A61L 27/52* | (2006.01) |
| *A61L 27/54* | (2006.01) |
| *A61L 27/12* | (2006.01) |
| *A61K 9/00* | (2006.01) |
| *A61K 47/02* | (2006.01) |
| *A61L 27/02* | (2006.01) |
| *C01B 25/45* | (2006.01) |
| *A61C 8/00* | (2006.01) |
| *C01B 25/34* | (2006.01) |

(52) U.S. Cl.
CPC ............... *C01B 25/45* (2013.01); *A61C 8/00* (2013.01); *A61K 9/0019* (2013.01); *A61K 9/0024* (2013.01); *A61K 47/02* (2013.01); *A61L 27/025* (2013.01); *A61L 27/12* (2013.01); *A61L 27/52* (2013.01); *A61L 27/54* (2013.01); *C01B 25/34* (2013.01); *A61C 8/0087* (2013.01); *A61L 2400/12* (2013.01); *A61L 2430/02* (2013.01); *C01P 2002/20* (2013.01); *C01P 2002/60* (2013.01); *C01P 2004/50* (2013.01)

(58) Field of Classification Search
None
See application file for complete search history.

(56) References Cited

U.S. PATENT DOCUMENTS

| | | | |
|---|---|---|---|
| 6,451,361 B1 | 9/2002 | Moore | |
| 6,669,928 B1 | 12/2003 | Gurol | |
| 2015/0150973 A1 | 6/2015 | Barralet | |

FOREIGN PATENT DOCUMENTS

WO 2013/142996 10/2013

OTHER PUBLICATIONS

International Search Report dated Feb. 14, 2017 in International (PCT) Application No. PCT/CA2016/051415.
Laurenti et al., "Two-Dimensional Magnesium Phosphate Nanosheets Form Highly Thixotropic Gels That Up-Regulate Bone Formation", Nano Letters, vol. 16, Jun. 9, 2016, pp. 4779-4787.
Tamimi et al., "Biocompatibility of magnesium phosphate minerals and their stability under physiological conditions", Acta Biomaterialia, vol. 7, Feb. 13, 2013, pp. 2678-2685.
Written Opinion of the International Searching Authority dated Feb. 14, 2017 in International (PCT) Application No. PCT/CA2016/051415.
Extended European Search Report dated Jul. 2, 2019 in corresponding European Patent Application No. 16871858.3.
Jia et al., "Development of magnesium calcium phosphate biocement for bone regeneration", Journal of the Royal Society Interface, vol. 7, No. 49, pp. 1171-1180, 2010.

*Primary Examiner* — Patricia Duffy
*Assistant Examiner* — Garen Gotfredson
(74) *Attorney, Agent, or Firm* — Wenderoth, Lind & Ponack, L.L.P.

(57) ABSTRACT

A hydrogel comprising a colloidal suspension of $M^I_x M^{II}_y P_z$ two-dimensional nanocrystals in water, wherein $M^I$ is $Na^+$ and/or $Li^+$, $M^{II}$ is $Mg^{2+}$ or a mixture of $Mg^{2+}$ with one or more $Ni^{2+}$, $Zn^{2+}$, $Cu^{2+}$, $Fe^{2+}$ and/or $Mn^{2+}$, P is a mixture of dibasic phosphate ions ($HPO_4^{2-}$) and tribasic phosphate ions ($PO_4^{3-}$). X ranges from about 0.43 to about 0.63, Y ranges from about 0.10 to about 0.18, Z ranges from about 0.29 to about 0.48, X, Y, Z being mole fractions, is provided.

19 Claims, 45 Drawing Sheets

Specification includes a Sequence Listing.

A

B

MAGNESIUM PHOSPHATE HYDROGELS

CROSS REFERENCE TO RELATED APPLICATIONS

This application is a continuation of U.S. application Ser. No. 16/060,462, filed Jun. 8, 2018, which in turn is a U.S. national stage application of PCT/CA2016/051415 filed Dec. 2, 2016, which in turn claims benefit, under 35 U.S.C. § 119(e), of U.S. provisional application Ser. No. 62/265,570, filed on Dec. 10, 2015.

SEQUENCE LISTING

A sequence listing in electronic (ASCII text file) format is filed with this application and incorporated herein by reference. The name of the ASCII text file is "2020_2904_seq_listing.txt"; the file was created on Jan. 20, 2021; the size of the file is 4 KB.

FIELD OF THE INVENTION

The present invention relates to magnesium phosphate hydrogels. More specifically, the present invention is concerned with such gels and their uses as scaffolds for bone tissue engineering, as drug delivery systems and in pastes for cleaning dental implants.

BACKGROUND OF THE INVENTION

Two-Dimensional (2D) Layered Materials

Over the past decade, the field of two-dimensional (2D) layered materials has grown extensively, especially after the isolation and characterization of graphene. 2D nanomaterials have attracted a great interest since they present extraordinary properties that are usually absent in their bulk form. Recent progress in 2D nanomaterials technologies also paved the way in developing advanced biomaterials, and in the large family of 2D nanomaterials exfoliated synthetic clays have been used in many advanced technological applications The design of nanomaterials with a well-defined 2D morphology and their large-scale manufacturing at low cost, in particular, remain crucial challenges to unfold the very promising future of nanotechnology. In fact, the synthesis of 2D nanomaterials is often time-consuming and involves multi-step procedures that may use toxic and/or expensive chemicals for the exfoliation/delamination process, or hydrothermal process at high temperatures and pressures. Overall these methods might be expensive, do not offer scope for scalability, and are inappropriate for the synthesis of biomaterials. In recent years, sonochemical techniques have been extensively used in the synthesis of nanostructured materials. During the acoustic cavitation process, very high temperatures (>5000 K), pressures (>20 MPa), and cooling rates (>$10^{10}$ K/s) can be achieved upon the collapse of the bubble. However, the application of sonochemical process to a large-scale level is a very complicated task.

Clays are plate-like polyions with a heterogeneous charge distribution that forms a physical gel in water at concentrations higher than 40 mg/mL due to the simultaneous presence of positive and negative charges that give rise to electrostatic and van der Waals interactions. This allows the gel to behave as a thixotropic material due to the formation of a 3D network of particles known as the "house of cards" structure. Thixotropic materials can be liquefied by applying mechanical energy allowing the physical gel to behave as a liquid; then when the mechanical stress is removed Brownian motions drive the particles into contact to reform the 3D network and the liquefied dispersion becomes gel-like again.

Inorganic Biomaterials, Phosphates, Magnesium

Several inorganic biomaterials such as calcium phosphates, hydroxyapatite, beta tri-calcium phosphates, monetite, brushite, and orthosilicic acid have been studied as osteoinducers. However, these materials present insufficient in vivo degradation which results in slow resorption. They also have limited injectability, and tissue regeneration limits making necessary the development of a new biomaterial generation which can facilitate the formation of functional tissues.

Magnesium is the fourth most common metal in human body, 50% of the body's magnesium is stored in bone, and it shares many chemical similarities with calcium. Magnesium plays an important role in mineral metabolism promoting calcification, hydroxyapatite (HA) crystal formation, increases bone cell adhesion, proliferation, and differentiation. Among phosphate-based materials, magnesium phosphates have demonstrated to be biocompatible and resorbable in vivo.

Binary transition metal phosphates because of their interesting industrial properties have received considerable amount of attention. The synthesis of a series of phosphates $M^IM^{II}PO_4 \cdot H_2O$ ($M^I$=K, $NH_4$; $M^{II}$=Mg, Mn, Fe, Co, Ni) was first reported in 1933.

Cleaning Dental Implants

Oral biofilm can accumulate onto the surface of dental implants causing infection and compromising implant survival. The accumulation of bacterial biofilm on titanium (Ti) implants changes the surface biocompatibility and initiates peri-implant diseases (peri-implant mucositis and peri-implantitis). These can cause marginal bone loss and eventually implant failure. Therefore, regular removal of oral biofilm from Ti implants is critical to maintain oral health and ensure long-term implant success.

Home-use and professional oral hygiene techniques are thus highly indicated to prevent or manage the peri-implant infections and thus increase implant survival. Personal and professional plaque control with brushes, polishing cups and pastes has indeed been used to remove biofilms covering implant surfaces. These techniques should be capable of removing bacterial biofilms without negatively affecting the implant biocompatibility, but they currently cannot. Further, even though these techniques decrease the symptoms of peri-implant infections, they do not achieve complete biofilm removal from the implants. In fact, available prophylaxis pastes and toothpastes present limited efficiency in cleaning implant surfaces because they were all originally designed for cleaning teeth not implants. In particular, they are made of organic thickeners and surfactants that can bind to titanium and alter its properties.

Conventional toothpastes have indeed been developed to promote dental health and assist the mechanical removal of biofilm from teeth with brushes. The composition of most toothpastes includes abrasives (hydrated silica, calcium carbonate, alumina), surfactants (glycerin, sorbitol), organic thickeners (xanthan, cellulose gums), and antimicrobials (fluoride, triclosan). However, these additives can have a negative impact on the stability and chemical properties of implant surfaces.

Fluoride ions can initiate surface corrosion of Ti metal and alloys, altering its surface chemistry, topography and roughness. The effect of fluoride is not limited to the time of oral hygiene procedure because the fluoride could be retained and concentrated in the plaque, and it can be found in saliva 24 hours after the use of fluoridated oral hygiene products.

Furthermore, organic macromolecules are known to spontaneously adsorb to metals causing alteration in their physical chemistry and surface charge. Natural and synthetic inorganic clays such as Laponite (layered magnesium silicate) are used in the prophylaxis and toothpastes as binders or stabilizer, but they are commonly incorporated with other organic thickeners (i.e. xanthan gum) to obtain the optimal consistency of a dentifrice. The organic compounds can attach tightly to the implant surface which make it impossible to clean the surface without damaging its microtexture. Moreover, clays are silicate based gels that could be too abrasive on implant surfaces.

In addition, the abrasives incorporated in regular toothpastes or polishing pastes can damage implants surfaces and increase their roughness. Abrasives are indeed added to enhance the cleaning action of the toothbrush and to physically scrub the external surface of teeth/implants, removing the organic pellicle (salivary proteins), plaque bacteria and other extrinsic stains. Calcium carbonate, silica and alumina are the common abrasive elements used in the current pastes.

Prophylaxis instruments, such as brushes or rubber cups, have been used to decontaminate implants and remove the attached biofilms with or without using prophylaxis pastes. They showed a relative moderate efficiency in biofilm removal without negative effects on the implant surfaces. However, implant surface damage was reported with the use of highly abrasive rubber cups and/or polishing paste.

In view of the above, it advisable to use toothpastes and instruments with low abrasiveness for daily oral hygiene maintenance for subjects' with Ti implants. In fact, toothpastes have to be carefully selected when implant restorations are present. Unfortunately, no specific "implant-paste" exists. Colgate™ Total toothpaste is a representative conventional toothpaste that is used for personal daily care mainly to reduce plaque and prevent gum infections. It composed of antimicrobials (sodium fluoride, triclosan), organic thickeners (cellulose gum and copolymers), abrasives (hydrated silica and titanium dioxide), and humectants (glycerin and sorbitol).

Bone Regeneration

Minimally invasive surgical interventions have been shown to reduce operation and anesthesia time, minimize intra-operative complications, minimize postoperative pain, shorten recovery duration and hospital stay which in turn reduce morbidity and mortality rates, and minimize the cost of the intervention. Thus, such interventions have gained great deal of publicity.

Bone regeneration procedures require invasive and painful interventions. Bone fixation for instance involve invasive incision through skin and muscle to expose bone in order to place fixation plates. Such intervention increase risk of damage to adjacent anatomical structure such as nerve injury.

Pain management in bone regeneration interventions is limited to the use of drugs such as non-steroidal anti-inflammatories, opioids, acetaminophen and local anesthetics. However, these drugs have several limitations. Non-steroidal anti-inflammatories delay bone healing and increase the risk of gastrointestinal diseases. Opioids are controlled drugs, and have major side effects such as constipation and addiction. Acetaminophen is usually not effective in moderate or severe bone pain. Local anesthetics are relatively the most effective and have the least side effects, however they are limited by their short duration of action.

SUMMARY OF THE INVENTION

In accordance with the present invention, there is provided a hydrogel comprising a colloidal suspension of $M^I_X M^{II}_Y P_Z$ two-dimensional nanocrystals in water, wherein:
$M^I$ is $Na^+$ and/or $Li^+$,
$M^{II}$ is $Mg^{2+}$ or a mixture of $Mg^{2+}$ with one or more $Ni^{2+}$, $Zn^{2+}$, $Cu^{2+}$, $Fe^{2+}$ and/or $Mn^{2+}$,
P is a mixture of dibasic phosphate ions ($HPO_4^{2-}$) and tribasic phosphate ions ($P_4^{3-}$),
X ranges from about 0.43 to about 0.63,
Y ranges from about 0.10 to about 0.18, and
Z ranges from about 0.29 to about 0.48,
X, Y, Z being mole fractions.

There is also provided the above hydrogel, wherein X ranges from about 0.45 to about 0.56, from about 0.45 to about 0.55, preferably from about 0.45 to about 0.53, more preferably from about 0.50 to about 0.58, and most preferably is about 0.52.

There is also provided any and all of the above hydrogels, wherein Y ranges from about 0.13 to about 0.18, preferably from about 0.14 to about 0.18, more preferably from about 0.13 to about 0.16, and most preferably is about 0.15.

There is also provided any and all of the above hydrogels, wherein Z ranges from about 0.30 to about 0.39, preferably from about 0.31 to about 0.37, more preferably from about 0.34 to about 0.37, and most preferably is about 0.33.

There is also provided any and all of the above hydrogels, wherein $M^I$ is $Na^+$; wherein $M^I$ is $Li^+$, or $M^I$ is a mixture of $Na^+$ and $Li^+$.

There is also provided any and all of the above hydrogels, wherein $M^{II}$ is $Mg^{2+}$; $M^{II}$ is a mixture of $Mg^{2+}$, and one or more $Ni^{2+}$, $Zn^{2+}$, $Cu^{2+}$, $Fe^{2+}$ and/or $Mn^{2+}$; or wherein $M^{II}$ is a mixture of $Mg^{2+}$ and $Fe^{2+}$.

There is also provided any and all of the above hydrogels, comprising one or more of $Ni^{2+}$, $Zn^{2+}$, $Cu^{2+}$, $Fe^{2+}$ and/or $Mn^{2+}$ in a total mole fraction of up to about 0.3Y, more preferably a total mole fraction of up to about 0.2Y, and more preferably a total mole fraction of about 0.16Y.

There is also provided any and all of the above hydrogels, wherein $M^I$ is $Na^+$, $M^{II}$ is $Mg^{2+}$, X is 0.516, Y is 0.144, and Z is 0.34; wherein $M^I$ is $Na^+$, $M^{II}$ is $Mg^{2+}$, X is 0.45, Y is 0.18, and Z is 0.37; wherein $M^I$ is $Na^+$, $M^{II}$ is $Mg^{2+}$, X is 0.53, Y is 0.13, and Z is 0.34; wherein $M^I$ is $Na^+$, $M^{II}$ is a mixture of $Mg^{2+}$ and $Fe^{2+}$, X is 0.55, Y is 0.14, and Z is 0.31; wherein $M^I$ is $Na^+$, $M^{II}$ is $Mg^{2+}$, X is 0.52, Y is 0.13, and Z is 0.35; wherein $M^I$ is $Na^+$, $M^{II}$ is $Mg^{2+}$, X is 0.55, Y is 0.14, and Z is 0.31, or wherein $M^I$ is $Na^+$, $M^{II}$ is $Mg^{2+}$, X is 0.56, Y is 0.13, and Z is 0.31.

There is also provided any and all of the above hydrogels, having a pH between about 7 and about 11, between about 7 to about 10, preferably between about 7 and about 9, more preferably pH between about 7.5 and about 8.5, yet more preferably between about 7.5 and about 8, and more preferably a pH of about 7.8.

There is also provided any and all of the above hydrogels, comprising between about 5% and about 50%, preferably between about 5% and about 25%, more preferably between about 5% and about 15%, and most preferably about 10% by weight of $M^I_X M^{II}_Y P_Z$, based on the total weight of the gel.

There is also provided any and all of the above hydrogels, comprising between about 50% and about 95%, preferably between about 75% and about 95%, more preferably between about 85% and about 95%, most preferably about 90% of water by weight based on the total weight of the gel.

There is also provided any and all of the above hydrogels, comprising up to 15%, preferably up to about 10%, more preferably between about 4 and about 9% of hydration water by weight based on the total weight of the gel.

There is also provided any and all of the above hydrogels, wherein the hydrogel comprises $M^I_X M^{II}_Y P_Z$ two-dimensional nanocrystals agglomerated and forming interconnected planes with water in empty spaces between the agglomerated nanocrystals.

There is also provided any and all of the above hydrogels, wherein the hydrogel comprises a honeycomb network of extended sheet-like face-to-face aggregates that are bent, twisted, branched, and intertangled with few edge-to-face contacts There is also provided any and all of the above hydrogels, further comprising one or more additive.

There is also provided any and all of the above hydrogels, further comprising one or more bioactive agents.

There is also provided any and all of the above hydrogels, for use in bone tissue engineering.

There is also provided any and all of the above hydrogels, for use as a scaffold for bone tissue engineering.

There is also provided any and all of the above hydrogels, for promoting bone regeneration and/or peri-implant bone growth There is also provided any and all of the above hydrogels, for use as a drug delivery system.

In another related aspect of the invention, there is provided a scaffold for bone growth, for bone repair, and/or for bone regeneration comprising any of the above hydrogels.

In another related aspect of the invention, there is provided a bone graft and/or a bone regeneration material comprising any of the above hydrogels.

In another related aspect of the invention, there is provided a method for:
promoting bone regeneration,
promoting bone growth (for example peri-implant bone growth),
treating a bone defect, and/or
treating a bone injury,
the method comprising the step of administering any of the above hydrogels at a site of need.

There is also provided the above method, wherein the administering step comprises implanting the hydrogel or injecting the hydrogel. There is also provided the above method, wherein the site of need is a bone defect or a bone injury.

In another related aspect of the invention, there is provided a kit comprising a container containing any of the above hydrogels and instructions for using the hydrogel for promoting bone regeneration, promoting bone growth (for example peri-implant bone growth), treating a bone defect, and/or treating a bone injury. There is also provided the above kit, wherein the container is a syringe.

In another related aspect of the invention, there is provided a pharmaceutical composition comprising one or more bioactive agents and any of the above hydrogels as a carrier for the bioactive agent. There is also provided the above pharmaceutical composition, wherein the pharmaceutical composition is an implant or an injectable. There is also provided the above pharmaceutical composition, wherein the bioactive agent is a local anesthetic.

In another related aspect of the invention, there is provided a method of delivering a bioactive agent to a patient, the method comprising the step of administering any of the pharmaceutical composition to the patient. In another related aspect of the invention, there is provided a method of targeting delivery of a bioactive agent to a site of need of a patient, the method comprising the steps of administering any of the pharmaceutical composition to the site of need. There is also provided the above methods, wherein the site of need is a bone defect or a bone injury. There is also provided the above methods, wherein said administering step comprises implanting the hydrogel or injecting the hydrogel.

In another related aspect of the invention, there is provided a paste for cleaning dental implant, the paste comprising any of the above hydrogels mixed with an abrasive agent.

There is also provided the above paste, wherein the gel has a pH between about 9 and about 10.

There is also provided the above paste, wherein, in the hydrogel, $M^I$ is $Na^+$, $M^{II}$ is $Mg^{2+}$, X is 0.56, Y is 0.13, and Z is 0.31.

There is also provided the above paste, wherein the abrasive agent is a silica, such as a magnesium phosphate silica, a nano-silicate or calcium carbonate.

There is also provided the above paste, wherein the abrasive agent is hydrated silica nanoparticles.

There is also provided the above paste, wherein abrasive agent particles have a particles size up to about 500 nm, preferably up to about 400 nm, and more preferably ranging from about 200 to about 300 nm.

There is also provided the above paste, comprising from about 5 to about 60%, preferably from about 20 to about 40%, more preferably about 30% by weight of the abrasive agent, based on the total weight of the paste.

There is also provided the above paste, further comprising one or more additives.

In another related aspect of the invention, there is provided a method of manufacturing any of the above hydrogel, the method comprising providing a first reservoir containing a first aqueous solution comprising $Mg^{2+}$ ions, dibasic phosphate ions ($HPO_4^{2-}$) and tribasic phosphate ions ($PO_4^{3-}$), and optionally further comprising one or more $Ni^{2+}$, $Zn^{2+}$, $Cu^{2+}$, $Fe^{2+}$ and/or $Mn^{2+}$,
providing a second reservoir containing a second aqueous solution comprising $Na^+$ and/or $Li^+$ ions,
providing a small-volume mixing chamber flowably connected to said first and second reservoir and having an outlet,
simultaneously feeding said first and second solutions to the mixing chamber, thereby manufacturing said hydrogel, and
collecting the hydrogel via the outlet of the mixing chamber.

DETAILED DESCRIPTION OF THE INVENTION

Hydrogel

Figure 1:
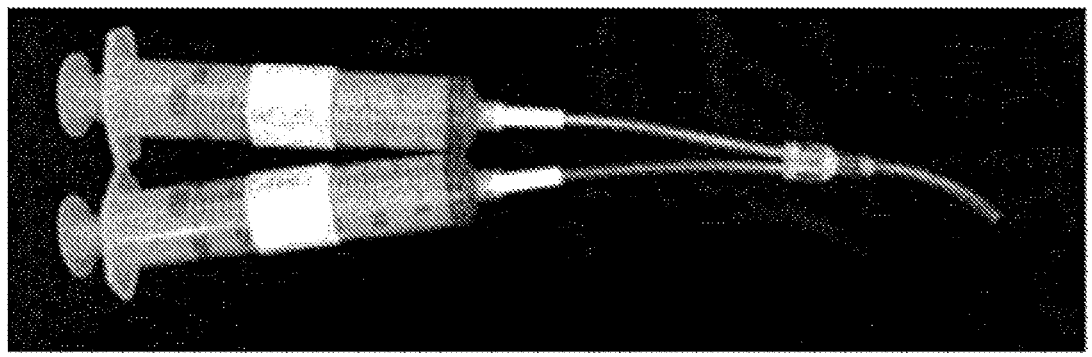
FIG. 1 shows an apparatus for manufacturing the hydrogel described herein.

In accordance with the present invention, there is provided a hydrogel comprising a colloidal suspension of $M^I_X M^{II}_Y P_Z$ two-dimensional nanocrystals in water.

In the above chemical formula:

$M^I$ is a monovalent cation and is $Na^+$ and/or $Li^+$, $M^{II}$ is a divalent cation and is $Mg^{2+}$ or a mixture of $Mg^{2+}$ with one or more $Ni^{2+}$, $Zn^{2+}$, $Cu^{2+}$, $Fe^{2+}$ and/or $Mn^{2+}$, P is a mixture of dibasic phosphate ions ($HPO_4^{2-}$) and tribasic phosphate ions ($PO_4^{3-}$), X ranges from about 0.43 to about 0.63, Y ranges from about 0.10 to about 0.18, and Z ranges from about 0.29 to about 0.48, X, Y, Z being mole fractions.

It will be readily apparent to the skilled person that, since X, Y and Z are mole fractions, their sum should be 1 (give or take the rounding errors). This is indeed the standard definition of mole fraction in the art: "In chemistry, the mole fraction is defined as the amount of a constituent divided by the total amount of all constituents in a mixture. The sum of all the mole fractions is equal to 1". Herein, the mole fractions calculation takes only the divalent cations ($M^{II}$), phosphate anions (P) and monovalent cations ($M^I$) into account. Water and optional additives that can be added to the gel are not considered.

In embodiments, X is 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, or 0.62 or more. In these or other embodiments, X is 0.63, 0.62, 0.61, 0.60, 0.59, 0.58, 0.57, 0.56, 0.55, 0.54, 0.53, 0.52, 0.51, 0.50, 0.49, 0.48, 0.47, 0.46, 0.45, or 0.44 or less. In embodiments, X is about any of the preceding values.

In embodiments, Y is 0.10, 0.11, 0.12, 0.13, 0.14, 0.15, 0.16, or 0.17 or more. In these or other embodiments, Y is 0.18, 0.17, 0.16, 0.15, 0.14, 0.13, 0.12, or 0.11 or less. In embodiments, Y is about any of the preceding values.

In embodiments, Z is 0.29, 0.30, 0.31, 0.32, 0.33, 0.34, 0.35, 0.36, 0.37, 0.38, 0.39, 0.40, 0.41, 0.41, 0.42, 0.43, 0.44, 0.45, 0.46, or 0.47 or more. In these or other embodiments, Z is 0.48, 0.47, 0.46, 0.45, 0.44, 0.43, 0.42, 0.41, 0.40, 0.39, 0.38, 0.37, 0.36, 0.35, 0.34, 0.33, 0.32, 0.31, or 0.30 or less. In embodiments, Z is about any of the preceding values.

In preferred embodiments, X ranges from about 0.45 to about 0.56, from about 0.45 to about 0.55, preferably from about 0.45 to about 0.53, more preferably from about 0.50 to about 0.58, and most preferably is about 0.52.

In preferred embodiments, Y ranges from about 0.13 to about 0.18, preferably from about 0.14 to about 0.18, more preferably from about 0.13 to about 0.16, and most preferably is about 0.15.

In preferred embodiments, Z ranges from about 0.30 to about 0.39, preferably from about 0.31 to about 0.37, more preferably from about 0.34 to about 0.37, and most preferably is about 0.33.

In preferred embodiments, the monovalent cation ($M^I$) is $Na^+$.

In embodiments, the monovalent cation ($M^I$) is $Li^+$.

In embodiments, the monovalent cation ($M^I$) is a mixture of $Li^+$ and $Na^+$.

In preferred embodiments, the divalent cation ($M^{II}$) is magnesium ($Mg^{2+}$) only.

In other embodiments, part of the magnesium is replaced by one or more of $Ni^{2+}$, $Zn^{2+}$, $Cu^{2+}$, $Fe^{2+}$, and/or $Mn^{2+}$. In other words, $M^{II}$ is a mixture of $Mg^{2+}$, with one or more of $Ni^{2+}$, $Zn^{2+}$, $Cu^{2+}$, $Fe^{2+}$ and/or $Mn^{2+}$, or any combination or subset thereof. In embodiments, the one or more of $Ni^{2+}$, $Zn^{2+}$, $Cu^{2+}$, $Fe^{2+}$ and/or $Mn^{2+}$, is $Fe^{2+}$. In gels comprising such mixtures, the one or more of $Ni^{2+}$, $Zn^{2+}$, $Cu^{2+}$, $Fe^{2+}$ and/or $Mn^{2+}$, may be present in a total mole fraction of up to about 0.3Y (which means that $Mg^{2+}$ is present in a mole fraction of at least about 0.7Y). In preferred embodiments, the gel comprises the one or more of $Ni^{2+}$, $Zn^{2+}$, $Cu^{2+}$, $Fe^{2+}$ and/or $Mn^{2+}$ in a total mole fraction of up to about 0.2Y. In embodiments, the gels comprise the one or more of $Ni^{2+}$, $Zn^{2+}$, $Cu^{2+}$, $Fe^{2+}$ and/or $Mn^{2+}$, in a total mole fraction of about 0.16Y (and thus $Mg^{2+}$ in present in a mole fraction of about 0.84Y).

It will be apparent to the skilled person that the ratio of dibasic phosphate ions ($HPO_4^{2-}$) to tribasic phosphate ions ($PO_4^{3-}$) in the gel will depend on the exact pH of the gel.

In embodiments, the hydrogel has a pH between about 7 to about 11, preferably between about 7 to about 10, between about 7 and about 9, more preferably between about 7.5 and about 8.5, yet more preferably between about 7.5 and 8, most preferably a pH of about 7.8. Non-limiting examples of hydrogels with (more or most) preferred pH include:

| Hydrogels from the Examples below | X | Y | Z | pH |
|---|---|---|---|---|
| Example 3 ($M^I = Na^+$, $M^{II} = Mg^{2+}$) | 0.516 | 0.144 | 0.34 | 7.8 |
| Example 1, Formulation B ($M^I = Na^+$, $M^{II} = Mg^{2+}$) | 0.45 | 0.18 | 0.37 | 7.8 |
| Example 4 ($M^I = Na^+$, $M^{II} = Mg^{2+}$) | 0.53 | 0.13 | 0.34 | 7.95 |
| Example 2 ($M^I = Na^+$, $M^{II} = Mg^{2+} + Fe^{2+}$) | 0.55 | 0.14 (0.02 Fe + 0.12 Mg) | 0.31 | 8.1 |
| Example 1, Formulation A ($M^I = Na^+$, $M^{II} = Mg^{2+}$) | 0.52 | 0.13 | 0.35 | 8.3 |
| Example 2 ($M^I = Na^+$, $M^{II} = Mg^{2+}$) | 0.55 | 0.14 | 0.31 | 8.46 |
| Example 3 ($M^I = Na^+$, $M^{II} = Mg^{2+}$) | 0.56 | 0.13 | 0.31 | 9.6 |

Thus, in preferred embodiments, $M^I$ is $Na^+$, $M^{II}$ is $Mg^{2+}$, X is 0.516, Y is 0.144, and Z is 0.34;

$M^I$ is $Na^+$, $M^{II}$ is $Mg^{2+}$, X is 0.45, Y is 0.18, and Z is 0.37;

$M^I$ is $Na^+$, $M^{II}$ is $Mg^{2+}$, X is 0.53, Y is 0.43, and Z is 0.34;

$M^I$ is $Na^+$, $M^{II}$ is a mixture of $Mg^{2+}$ and $Fe^{2+}$, X is 0.55, Y is 0.14 (0.02 Fe+0.12 Mg), and Z is 0.31;

$M^I$ is $Na^+$, $M^{II}$ is $Mg^{2+}$, X is 0.52, Y is 0.13, and Z is 0.35;

$M^I$ is $Na^+$, $M^{II}$ is $Mg^{2+}$, X is 0.55, Y is 0.14, and Z is 0.31; and/or $M^I$ is $Na^+$, $M^{II}$ is $Mg^{2+}$, X is 0.56, Y is 0.13, and Z is 0.31.

In any and all of the above hydrogels, the amount of $M^I_X M^{II}_Y P_Z$ in the gel typically ranges between about 5% and about 50% by weight based on the total weight of the gel, for example between about 5% and about 25%, or between about 5% and about 15%. In preferred embodiments, the gel comprises about 10% of $M^I_X M^{II}_Y P_Z$.

In any and all of the above hydrogels, the amount of water (as a dispersing phase) in the gel typically ranges between about 50% and about 95% by weight based on the total weight of the gel, for example between about 75% and about 95%, or between about 85% and about 95%. In preferred embodiments, the gel comprises about 90% of water. A distinction should be drawn between water as a dispersing phase and hydration water. Water as a dispersing phase is the medium in which the nanosheets are dispersed. This water can be removed by drying the gel at a relatively low temperature, for example a temperature below the boiling temperature of water, such as 80° C. This process will produce a product that looks and feels dry, but that still contain hydration water.

On the other hand, hydration water consists in molecules of water that are bonded or somehow associated with a solid (for example entrapped within it). These molecules are typically only removed from the solid by heating the solid above the boiling temperature of water, often well above this temperature, for example between 100 and 250° C. The above hydrogel typically contains hydration water. For example, it may contain up to about 15% of hydration water by weight based on the total weight of the gel, for example up to about 10%, or between about 4 and about 9%.

When observed by transmission electron microscopy (TEM), in embodiments, the gel morphology comprises thin nano-plates or nanosheets ($M^I_X M^{II}_Y P_Z$ two-dimensional nanocrystals). More specifically, these nanosheets can be about 200 nm wide, very thin (e.g. about 10 nm thick) and up to 1 m long. As seen by TEM, these nanosheets agglomerate, and form interconnected planes (see for example FIGS. 18 to 21).

Herein, a "colloidal suspension" refers to a mixture comprising microscopically dispersed insoluble particles (herein the $M^I_X M^{II}_Y P_Z$ two-dimensional nanocrystals) suspended throughout a medium (herein water), in which the particles do not settle or take a long time to settle appreciably.

Herein, "nanocrystals" are crystalline particles having at least one dimension smaller than 100 nanometers. Herein, "two-dimensional nanocrystals" (2D nanocrystals) are thin sheet-like nanocrystals. In other words, the thickness of the 2D nanocrystals is much smaller than their width and length. In embodiments of the invention, the $M^I_X M^{II}_Y P_Z$ 2D nanocrystals that are up to about 10 nm thick. For example, their thickness may range between about 4 and about 7 nm. The length of the nanocrystals can be as high as about 1 m, for example 600 nm, and their width can be as high as about 250 nm, for example 200 nm. (See for example FIG. 24).

The hydrogel of the invention takes the form of a colloidal suspension of two-dimensional nanocrystals. In embodiments, the 2D nanocrystals form bundles or aggregates that together produce a 3D network, with the water composing the medium of the hydrogel in the empty spaces between the bundled nanocrystals. More specifically, the nanocrystals may partially overlap each other resulting in a honeycomb network of extended sheet-like face-to-face aggregates that are bent, twisted, branched, and intertangled with generally few edge-to-face contacts.

Herein, the terms "agglomerate", "aggregate" and "bundle" are used interchangeably.

In embodiments of any and all of the above hydrogels, the gel can also comprise one or more additives, such as nanoparticles (for example of silica), alginate, chitosan, or polyethylene glycol.

In embodiments of any and all of the above hydrogels, the gel can also comprise one or more bioactive agents, depending of the desired properties and its end use. Such agents will be discussed below.

Methods of Manufacturing the Hydrogel

In another aspect, the present invention provides methods of manufacturing the above hydrogel.

In these methods, the various ions can be provided using any of their water-soluble salts, oxides, acids or bases, which will typically be provided as aqueous solutions. For biological application, pharmaceutically acceptable starting materials are preferred. In particular, the starting materials shown in the following table can be used.

TABLE 1

Starting Materials (preffered starting materials are in bold)

| Ions | Starting Material |
|---|---|
| $Na^+$ | NaOH, $Na_2HPO_4$, $Na_5P_3O_{10}$, $NaH_2PO_4$ |
| $Li^+$ | LiOH |
| $Mg^{2+}$ | $Mg(OH)_2$, $MgCl_2$, $MgO$, $Mg(H_2PO_4)_2$ and $Mg_3(PO_4)_2$ |
| $Ni^{2+}$ | $NiCl_2$, $Ni(CH_3COO)_2$ |
| $Zn^{2+}$ | $ZnCl_2$, $Zn(CH_3COO)_2$, $Zn(OH)_2$, ZnO |
| $Cu^{2+}$ | $CuCl_2$, $Cu(OH)_2$ |
| $Fe^{2+}$ | $FeCl_2$, |
| $Mn^{2+}$ | $MnCl_2$, |
| $PO_4^{3-}$ and $PO_4^{3-}$ | $H_3PO_4$, $Na_2HPO_4$, $Na_5P_3O_{10}$, $NaH_2PO_4$ |

Of note, in the above, a given starting material can provide two types of ions at once.

The hydrogel of the invention can be prepared by mixing together solutions of the above starting materials. In preferred embodiments, a solution of the starting materials for the sodium and/or lithium ions is added to a solution containing the other starting materials.

Such simple mixing is adequate for producing small volume batches (for example 50 mL). However, for larger volume batches, the solution may not be homogenized quickly enough to produce the hydrogel and other phases will rather undesirably be obtained.

To produce larger volumes of gel, it is advantageous to use a continuous method (rather than a batch method). More specifically, there is provided a method of manufacture the above hydrogel, in which small volumes of the solutions are mixed, preferably continuously mixed, to produce the hydrogel.

This can be accomplished by:
  providing a first reservoir containing a first aqueous solution comprising $Mg^{2+}$ ions (alone or as a mixture $Mg^{2+}$ with one or more $Ni^{2+}$, $Zn^{2+}$, $Cu^{2+}$, $Fe^{2+}$ and/or $Mn^{2+}$), dibasic phosphate ions ($HPO_4^{2-}$) and tribasic phosphate ions ($PO_4^{3-}$), providing a second reservoir containing a second aqueous solution comprising $Na^+$ and/or $Li^+$ ions,
  providing a small-volume mixing chamber flowably connected to said first and second reservoir and having an outlet,
  simultaneously feeding said first and second solutions to the mixing chamber, thereby manufacturing said hydrogel, and
  collecting the hydrogel via the outlet of the mixing chamber.

In this method, the small-volume mixing chamber is of a volume sufficiently small to allow rapid and homogeneously mixing of both solutions. In embodiments, the mixing chamber has a volume of up to about 100 ml, for example up to about 50 ml, up to about 25 ml.

Small volumes of both solutions should be mixed with a sufficient turbulence to form the hydrogel. In embodiments, a turbulent regime with a Reynolds number >4000 will allow adequate mixing of the solutions and continuous production of the hydrogel. The turbulence may be controlled by adjusting the flow velocity of both solutions and the morphology (volume and shape) of the mixing chamber.

In embodiments, the mixing chamber can be provided with a stirrer.

FIG. 1 shows an embodiment of an apparatus allowing implementing the above method.

Properties of the Hydrogel

In embodiments, the hydrogel may present one or more of the following properties/advantages.

The hydrogels have a controlled pH that makes them suitable for biological applications.

The hydrogels present long term stability.

The hydrogels are thixotropic.

The hydrogels are injectable (through high gauge needles).

The hydrogels are biocompatible.

The hydrogels are bioresorbable.

The hydrogels control the release of bioactive agents.

The hydrogels can trigger unique osteogenic activities. The hydrogels can accelerate bone healing and/or osseointegration by enhancing collagen formation, osteoblasts differentiation and/or osteoclasts proliferation through up-regulation of COL1A1, RunX2, ALP, OCN and/or OPN.

Use as Scaffolds for Bone Tissue Engineering

Because, in embodiments, the present hydrogels can be injected through high gauge needles into bone defects, can accelerate bone healing and osseointegration (The results reported below in the Examples show a significant enhancement of bone healing and osseointegration compared to a control group, and a total resorption after only two weeks) and are bioresorbable, they could bring a paradigm shift in the fields of minimally invasive orthopedic and craniofacial interventions. Indeed, they could minimize the invasiveness of such interventions. The hydrogels could potentially replace conventionally used cements and (bio)ceramics.

The hydrogels as described above can thus be used in bone tissue engineering, notably to promote bone regeneration and peri-implant bone growth. They provide a temporary support media as well as a resorbable graft, the hydrogels being eventually replaced by bone.

Therefore, in a related aspect of the invention, there is provided a scaffold for bone growth, for bone repair, and/or for bone regeneration comprising the above hydrogel.

There is also provided a bone graft or bone regeneration material comprising the above hydrogel.

There are also provided methods for:
promoting bone regeneration,
promoting bone growth (in embodiments, peri-implant bone growth),
treating a bone defect, and/or
treating a bone injury,
these methods comprising the steps of administering the hydrogel at a site of need. In embodiments, said administering step comprises implanting the hydrogel. In other embodiments, said administering step comprises injecting the hydrogel. In embodiments, the site of need is a bone defect or a bone injury.

The term "bone defect" as used herein includes, but is not limited to, defects or voids/gaps resulting from compression fractures, benign bone cysts, diseased bone, high energy trauma, peri-articular fractures, cranial-maxillo facial fractures, osteoporotic reinforcement (i.e. screw augmentation), joint arthrodesis, joint arthroplasty and periodontal reconstruction.

There is also provided a kit comprising a container containing the hydrogel and instructions for using the hydrogel for promoting bone regeneration, promoting bone growth (in embodiments, peri-implant bone growth), treating a bone defect, and/or treating a bone injury as described. In embodiments, the container is a syringe.

In the above, the hydrogel can optionally comprise one or more additives and/or bioactive agents. The additives may be those discussed above. The bioactive agents will be discussed in the next section.

Use as a Drug Delivery System

The hydrogels as described above can be used as drug delivery systems.

Therefore, in a related aspect of the invention, there is provided a pharmaceutical composition comprising one or more bioactive agents and the hydrogel (as described above, for example including various additives) as a carrier for the bioactive agent. In preferred embodiments, the pharmaceutical composition is an implant or an injectable.

There is also provided a method of delivering a bioactive agent to a patient, the method comprising the step of administering the above pharmaceutical composition to the patient.

There is also provided a method of targeting delivery of a bioactive agent to a site of need of a patient, the method comprising the steps of administering the pharmaceutical composition to the site of need. In embodiments, the site of need is a bone defect or a bone injury.

In embodiments of the above methods, said administering step comprises implanting the hydrogel. In other embodiments of the above methods, said administering step comprises injecting the hydrogel.

The bioactive agents carried by the above hydrogels can be any such agent known in the art. Neutral and alkaline bioactive agents are generally preferred. Acidic bioactive agents can also be used. Some acidic bioactive agents, if they lower too much the pH of the gel, may however destabilize the hydrogel. In many cases, these agents can nevertheless be used as destabilization can be avoided by using a more alkaline gel, which will result in a product with in a final pH in the stability range of the hydrogel. An example of gel with a bioactive agent is provided in Example 4.

Non-limiting examples of bioactive agents that can be carried by the above hydrogels include local anesthetics such as mepivacaine, antibiotics such as imipenem, and beta blockers such as propranolol, as well as those discussed in the next paragraph.

In preferred embodiments, the hydrogel is used for bone tissue engineering as described above and as a drug delivery system simultaneously. In other words, in the scaffold for bone growth, the bone graft material, the bone regeneration material, the methods and the kit described in the previous section, the hydrogel comprises a bioactive agent for delivery to the patient. Suitable bioactive agents when the hydrogel is used in bone tissue engineering as described above include anesthetics, antibiotics, hormones and growth factors (i.e. osteogenic, vasogenic, or neurogenic growth factors) and proteins (i.e. osteopontin). Preferred bioactive agents in such case include anesthetics, more preferably local anesthetics, as well as antibiotics and osteogenic proteins. Examples of local anesthetics include mepivacaine. Examples of antibiotics include imipenem. Examples of hormones include melatonin. Examples of growth factors include platelet derived growth factors (PDGF), transforming growth factors (TGF-$\beta$), insulin-like growth factors (IGF's), fibroblast growth factors (FGF's), epidermal growth factor (EGF), human endothelial cell growth factor (ECGF), granulocyte macrophage colony stimulating factor (GM-CSF), nerve growth factor (NGF), vascular endothelial growth factor (VEGF), cartilage derived morphogenetic protein (CDMP). Examples of osteogenic proteins include OP-1, OP-2, BMP2, BMP3, BMP4, BMP9, DPP, Vg-1, 60 A, and Vgr-1, including naturally sourced and recombinant derivatives of the foregoing.

In such embodiments, the hydrogels advantageously provide pain relief and a minimally invasive technique for bone repair. Indeed, a material that can relief pain and be administered through minimal invasive procedures (e.g. injection) could bring a paradigm shift to the fields of orthopedic and craniofacial interventions, for example. This would potentially minimize the invasiveness of bone regeneration procedures, shorten the healing period and mobilization time, while eliminating or reducing the need for systemic drugs administration for pain management.

In embodiments, the hydrogel controls (for example, retards or extends) the delivery of the bioactive agent, thereby potentially enhancing its therapeutic window. This is notably the case with local anaesthetic mepivacaine (see the Example below).

Use in a Paste for Cleaning Dental Implants

The hydrogels as described above can also be used to produce a paste for cleaning dental implants.

Compared to conventional toothpastes commonly used for daily personal care, the paste of the invention is specifically designed for cleaning dental implants, which have cleaning requirements that differ significantly from natural teeth. To the inventor's knowledge, there is currently no product on the market specially designed and optimized for implant surface decontamination.

In embodiments, the paste of the invention allows removing biofilm contamination from titanium implant surfaces, while minimizing topographical changes to these surfaces (i.e. without affecting surface integrity). In contrast, regular commercial toothpastes, which are organic-based, are less effective in that context and may even contaminate the titanium implant surfaces—see the Examples below.

The paste of the invention could allow dentists and patients to remove biofilm from implants, control the peri-implant infections and/or favor re-osseointegration in case of bone loss. It could also be used for surgical decontamination of implant surfaces or professional cleaning of implants during maintenance visits. It could also be used for daily personal care to clean titanium abutments in case of overdenture or even to clean exposed implant surfaces.

Indeed, when wearing dental implants, titanium surfaces just below the crown, i.e. the "neck" of the implant, are commonly exposed.

Therefore, in an aspect of the invention, there is provided a paste for cleaning dental implants comprising the above hydrogel mixed with an abrasive agent. In the paste for cleaning dental implants, the hydrogel acts as a thickener and as carrier for the abrasive agent.

In preferred embodiments, the pH of the gel is between about 9 and about 10, especially is the implants to be cleans are made of titanium. One such gel is a gel in which, $M^I$ is $Na^+$, $M^{II}$ is $Mg^{2+}$, X is 0.56, Y is 0.13, and Z is 0.31.

In preferred embodiments, the paste is completely inorganic, i.e. it is free of organic compounds.

Turning to the abrasive agent, hard abrasive materials with large particle sizes should preferably be avoided as they can induce surfaces scratches or rounded edges on the implant, thus potentially increasing plaque accumulation. As such, the abrasive agent should have a relatively small average particle size, for example up to about 500 nm, preferably up to about 400 nm, and more preferably from about 200 to about 300 nm. Suitable abrasive agents include particles of silica, including magnesium phosphates silica, nano-silicates (that show osteoconductive properties that help inducing and accelerating bone regeneration) and/or calcium carbonate. More preferably, the abrasive agent is hydrated silica nanoparticles, especially those with average particles size of about 200 to about 300 nm.

The abrasive agent can be present in the paste at a concentration ranging from about 5% to about 60%, preferably from about 20% to about 40%, and more preferably about 30% by weight based on the total weight of the paste.

The paste for cleaning dental implants can comprise further additives, in particular such additives that are known as useful in dental cleaning pastes. Such additives include taste enhancers, coloring agents, sparkles as well as other functional ingredients. As noted above, such additives should be carefully selected to avoid inducing contamination of the implants with organic compounds.

Definitions

Herein, "to implant" means to insert something into a person's body, for example (but not limited to) by surgery. An "implant" is a material that is intended/designed to be implanted into a person's body.

Herein, "to inject" means to introduce something into a person's body using a needle. An "injectable" is a material that is intended/designed to be injected into a person's body.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Any and all combinations and sub-combinations of the embodiments and features disclosed herein are encompassed by the present invention. For example, all the disclosed components, properties and uses of the gel may be combined.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1—Magnesium Phosphate Gels that Up-Regulate Bone Formation and Bone Regeneration Here, we describe a novel nanocrystalline material with a 2D nanostructure and relevant properties for biomedical applications. We were able to synthesize a 2D biomaterial with properties such as biocompatibility, bioresorption, long term stability, thixotropy and/or injectability using a simple, potentially scalable, method. We discovered that sodium ions can regulate the precipitation of magnesium phosphate by interacting with the surface of the crystals causing a preferential crystal growth resulting in 2D morphology. The 2D material gave rise to a physical hydrogel base on a nanocrystalline material. This hydrogel was characterized in vitro and in vivo. We show below that it has a combination of osteogenic activities and accelerates bone healing and osseointegration by enhancing collagen formation, osteoblasts differentiation and osteoclasts proliferation through up-regulation of COL1A1, RunX2, ALP, OCN and OPN.

Experimental Section

Study and Characterization of the NaOH—Mg(OH)—$H_3PO_4$ System

Figure 2:
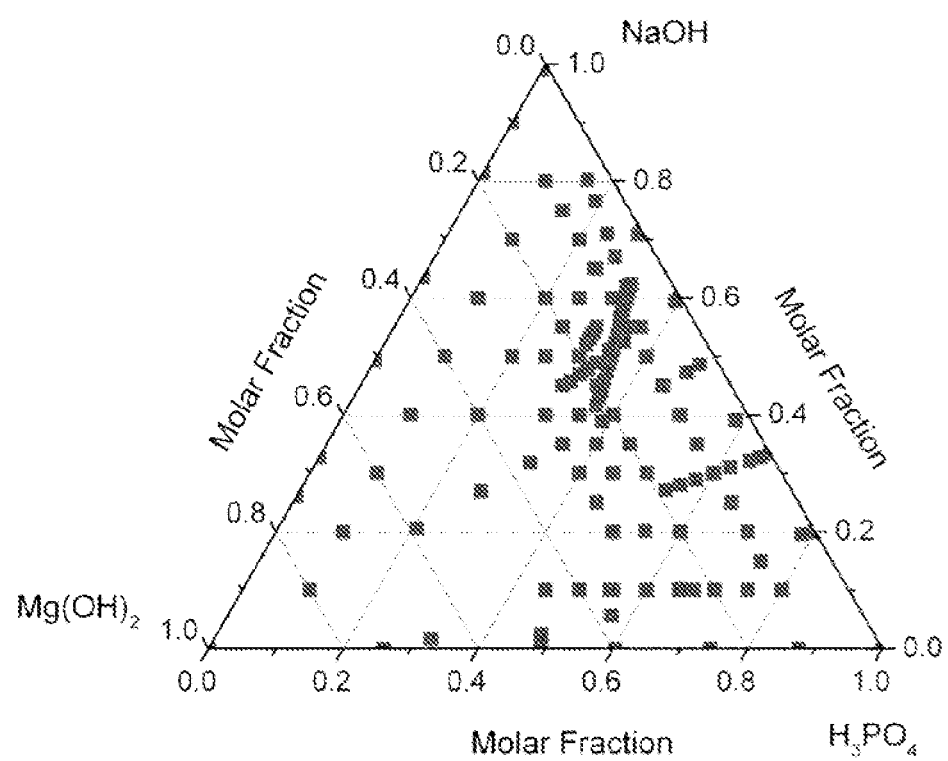
FIG. 2 shows the total points used to determine the different crystal phases of the ternary diagram of the system NaOH—Mg(OH)$_2$—H$_3$PO$_4$.

The title ternary system was investigated by varying the mole fraction of NaOH, $Mg(OH)_2$, and $H_3PO_4$ in different solutions. A fixed volume of 7 mL was used in all chemical reactions and the maximum reagents concentration was 10.5 mmol, in order to avoid any possible concentration effect. The ternary diagram was built using 141 different points obtained by mixing the three components at different mole fractions (FIG. 2). Precipitates obtained during the determination of the ternary diagram were prepared using the following procedure. 85 mg of $Mg(OH)_2$ were dissolved in 2.2 mL of $H_3PO_4$ 1.5 M and after complete dissolution 3.8 mL of NaOH 1.5 M were added under vigorous stirring. After mixing the two solutions, the resulting colloidal suspension was let stand for 2 hours, centrifuged at 4000 rpm for 5 minutes, and the supernatant was discarded. The solid precipitate was vacuum dried at room temperature and stored for characterization. The different crystal phases of the precipitates obtained during the ternary diagram were identified by means of X-ray diffraction (XRD). The diffraction patterns of the dried precipitates were recorded with a Bruker D8 Discover (Bruker AXS GmbH, Karlsruhe, Germany) from 50 to 58θ 2θ with a copper source ($\lambda_{Cu,K\alpha}$=1.5406 Å) at 40 kV and 40 mA and GADDS detector. The diffraction patterns were processed with EVA software (Bruker AXS GmbH, Karlsruhe, Germany) and phase composition was determined by comparing the acquired spectra with the phases identified in the International Centre for Diffraction Data (ICDD) database PDF-4.

Composition of the Stable NMP (NaMgPhosphate) Suspension

The elemental composition of stable NMP suspensions was determined using Inductively Coupled Plasma Optical Emission Spectroscopy (ICP-OES) with a Thermo Scientific iCAP 6000 Series ICP-OES (Thermo Fisher Scientific Inc, East Grinstead, UK). In a typical procedure, 6 mg of dried NMP powder was digested for 2 hours at 95° C. in 5 mL of $HNO_3$ 67% trace metals basis and all samples were prepared in triplicate. After digestion, the samples were let to cool down at room temperature and then diluted with deionized water up to 50 mL. From this solution 1 mL was taken and diluted with deionized water to 10 mL and measured by ICP-OES. The calibration curves were prepared using freshly prepared standards solution of $Mg^{2+}$, $Na^+$, and $P_4^{3-}$ with a concentration of 10, 5, 2, 1, and 0.1 ppm in $HNO_3$ 4%. The standard solutions were prepared by dilution from a certified standard solution of 1000 ppm in $HNO_3$ 4% (SCP Science Inc, Baie D'Urfe, Canada). The analysis pump rate was set to 50 rpm, the plasma radio frequency power was 1150 W, the auxiliary and nebulizer gas flow were set to 0.5 L min$^{-1}$. All measurements were performed in axial/radius mode.

Fourier Transform Infrared Spectroscopy (FT-IR) of the dried and heat treated NMP precipitates were recorded using a Perkin Elmer Spectrum Two (Perkin Elmer Inc, Waltham, Mass., USA) with single bounce diamond for Attenuated Total Reflectance (ATR). Spectra were recorded at room temperature from 450 to 4000 cm$^{-1}$ with a resolution of 4 cm$^{-1}$ and 64 scans.

Thermogravimetric analysis (TGA) was performed to calculate the amount of crystallization water of the dried NMP precipitates (SDT Q600 TA Instruments, TA Instruments-Waters L.L.C. New Castle, USA). TGA was done in vertical mode on a platinum pan from 30 to 1100° C. using a heating rate of 5° C./min, and in air atmosphere with a purge flow rate of 100 mL min-.

Figure 7:
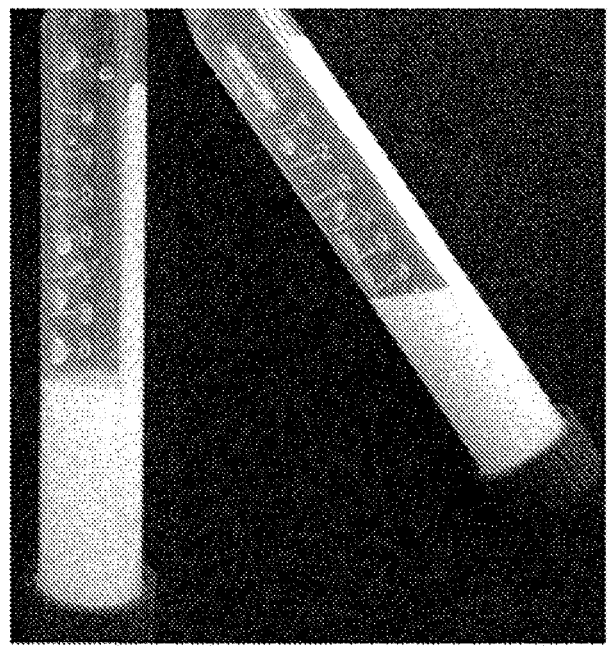
FIG. 7 is a picture of the suspension after 30 seconds from the beginning of the reaction.
Figure 8:
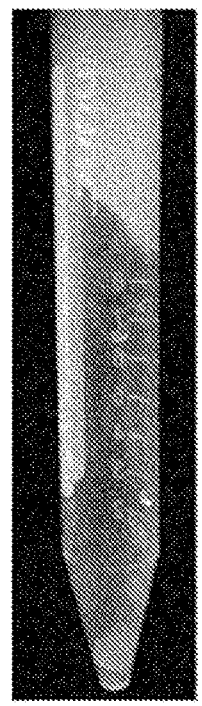
FIG. 8 shows the NMP colloidal suspension after 10 minutes.
Figure 9:
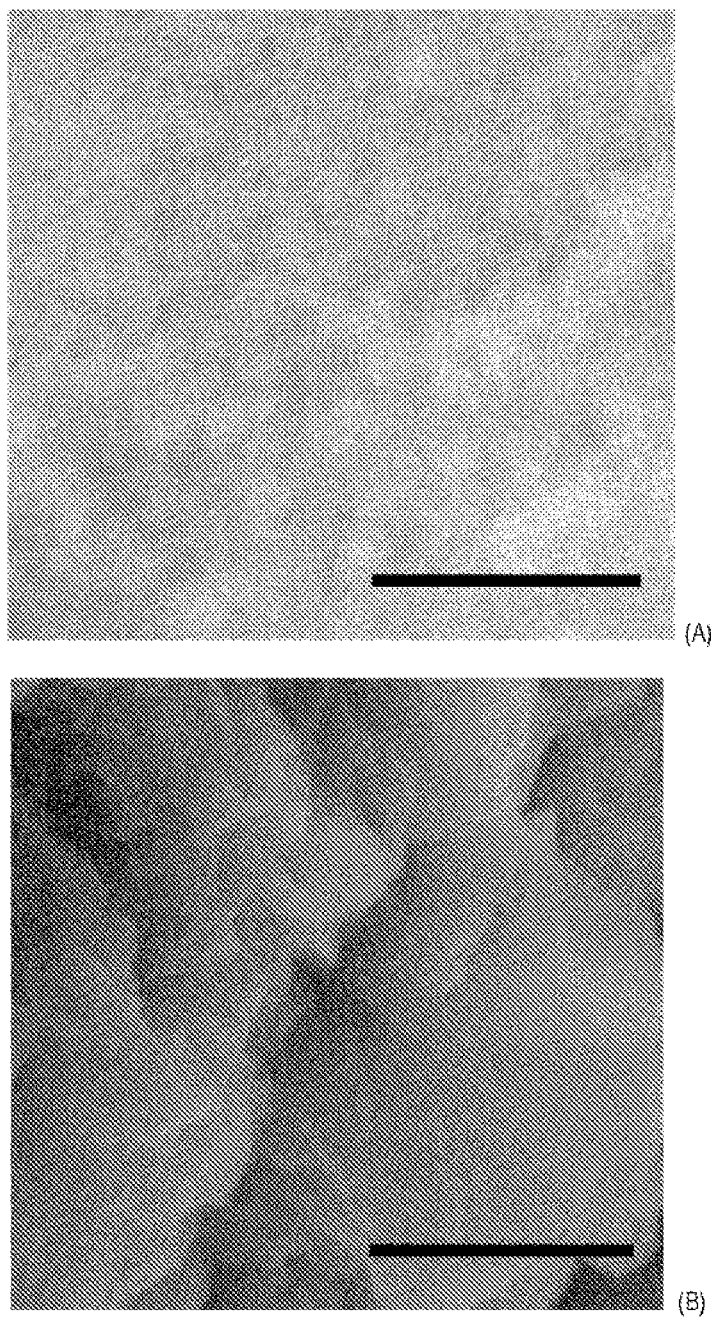
FIGS. 9 A and B show the NMP nanocrystals evolution during the reaction.
Figure 10:
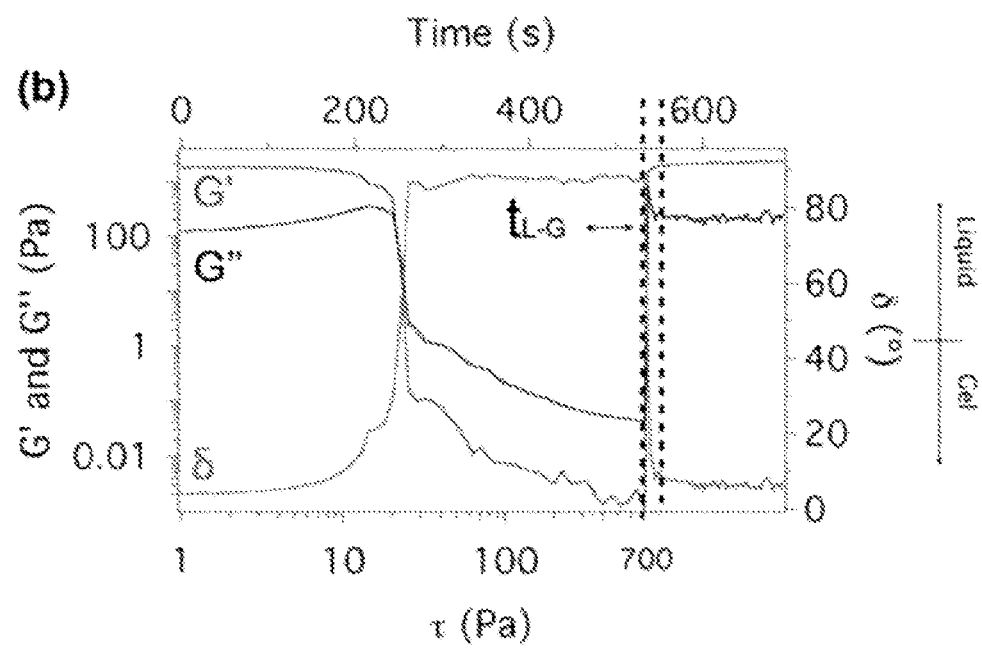
FIG. 10 shows the evolution of G', G" and δ of the gel of formulation A as a function of the increasing shear stress with time.
Figure 11:
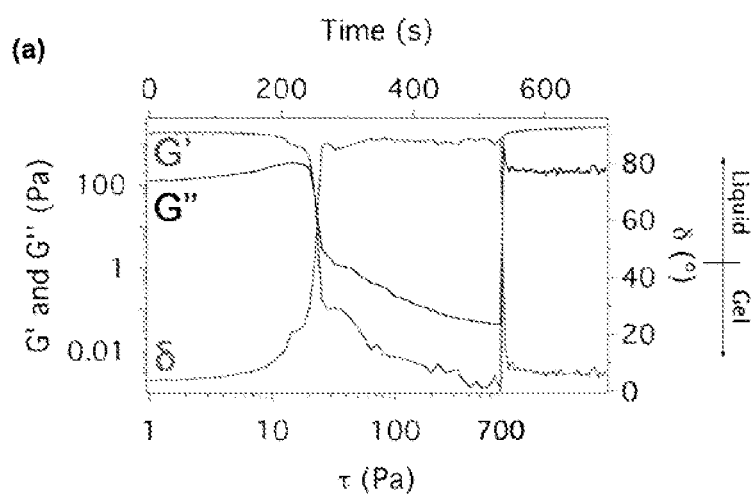
FIG. 11 shows the evolution of G', G" and δ of different gel formulations as a function of the increasing shear stress with time—rheology measurements of formulation A.
Figure 12:
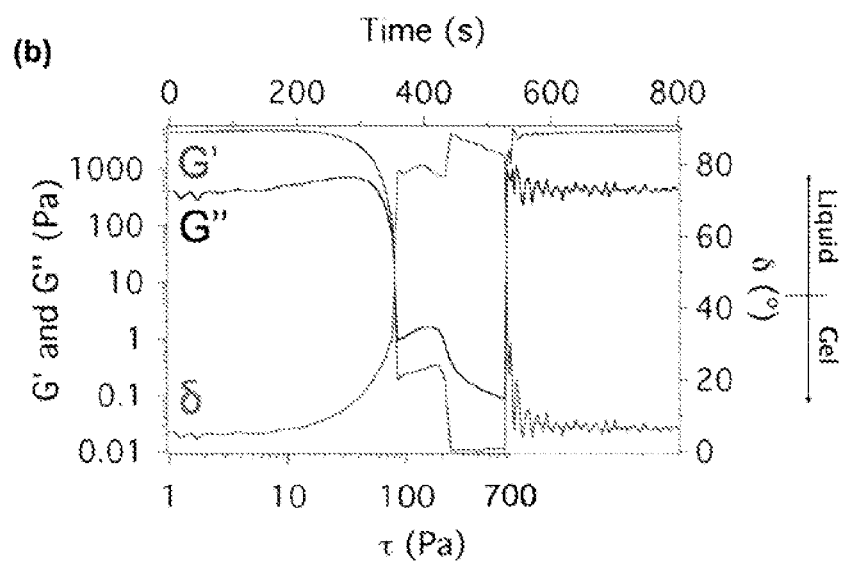
FIG. 12 shows the evolution of G', G" and δ of different gel formulations as a function of the increasing shear stress with time—rheology measurements of formulation B.
Figure 13:
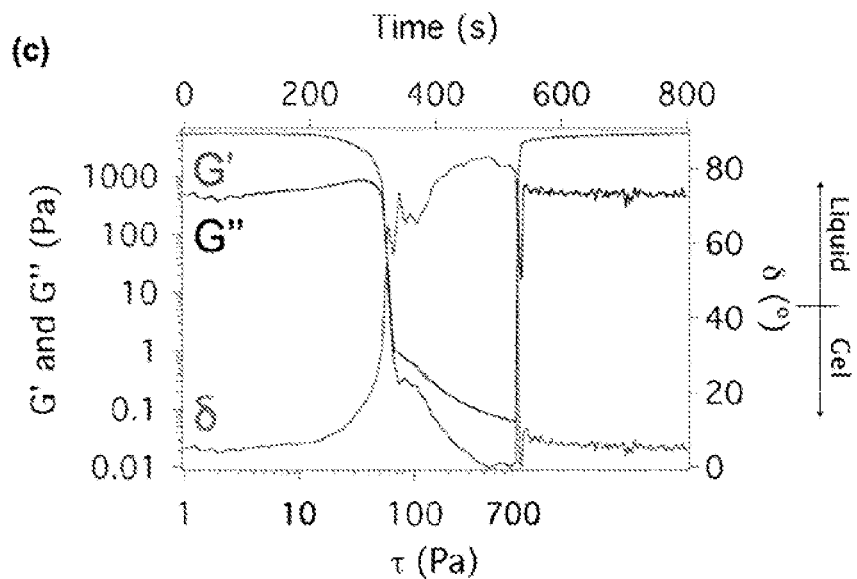
FIG. 13 shows the evolution of G', G" and δ of different gel formulations as a function of the increasing shear stress with time—rheology measurements of formulation C.
Figure 14:
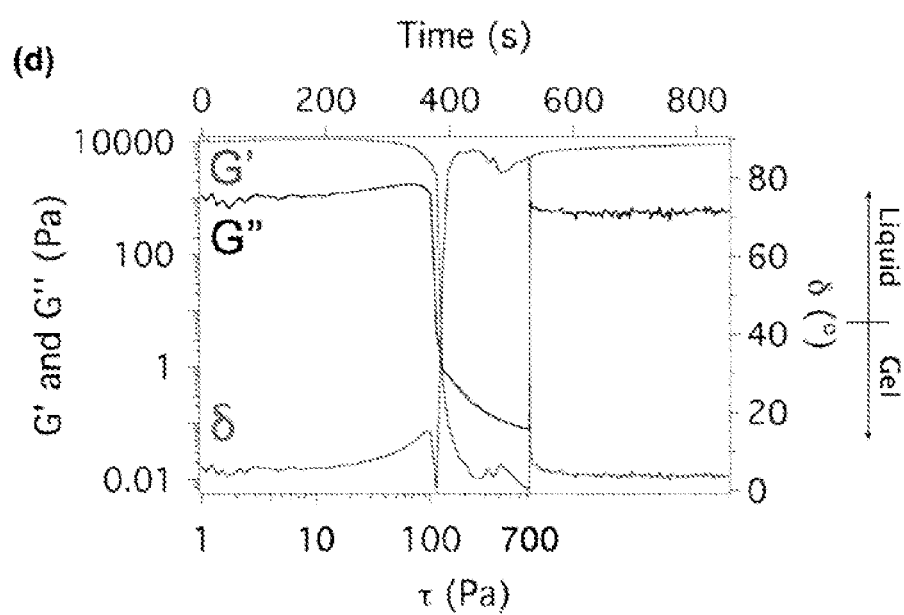
FIG. 14 shows the evolution of G', G" and δ of different gel formulations as a function of the increasing shear stress with time—rheology measurements of formulation D.

In a typical synthesis to produce NMP, in a solution of $H_3PO_4$ ($\eta H_3PO_4$=0.37) the pH value increased from 0.8 to 1.9 after adding and dissolving $Mg(OH)_2$ ($\eta Mg(OH)_2$=0.18). The addition of the NaOH solution ($\eta NaOH$=0.45, pH 8.3) provoked the instantaneous formation of a white liquid suspension made of nanocrystals with a uniform size of 50 nm. The pH of the suspension remained constant for 4 minutes before it began to slowly decrease and the white suspension became grey and solidified. During the following 30 minutes, the pH of the suspension stabilized at 7.8, and the small nanocrystals increased their size forming the final suspension composed of 2D nanocrystals with an undulate structure (FIGS. 7 to 9). The observed pH acidification during the reaction might arise from deprotonation of acidic phosphate moieties during the reaction as a result of the formation of tribasic orthophosphate ($PO_4^{3-}$).

Rheology, Nanocrystals Morphology, and 3-D Structure of the NMP Colloidal Suspension Colloidal suspensions of NMP were subjected to rheological measurements to determine the shear stress required for the gel-liquid transition, the liquid-gel transition time ($t_{L-G}$) upon removal of the shear stress, and the viscosity. The rheological experiments were performed with a rheometer AR2000 of TA Instruments (TA Instruments-Waters L.L.C. New Castle, USA) using parallel plates with a diameter of 40 mm and a distance between plates of 0.1 mm. Oscillatory measurements were conducted at a constant frequency (f=1 Hz), and the oscillatory stress sweeps ranged from 1 to 700 Pa. The equilibration time before to run the measurements was set to 10 minutes and all the measurements were performed at room temperature.

The force required to inject the NMP nanocrystals through an insulin needle of 160 μm of internal diameter was measured using the instrument Mach-1 V500cs and Mach-1 Motion software version 4.3.1 (Biomomentum Inc., Laval, Canada). The force was measured with a multiple-axis load cell of 70 N (resolution of 0.007 N) and acquisition rate of 100 Hz. The gel was loaded into the syringe avoiding the presence of bubble and then the plunger was inserted into the load cell. The force value was measured applying a constant vertical stage velocity of 1 mm s$^{-1}$ (resolution of 0.1 μm). The syringe loaded with deionized water required a force of 0.14±0.01 N, while for the NMP gels of formulation A-D were comprised in a range of 0.22±0.03 N and 0.77±0.04 N. At lower stage velocity (0.3 mm s$^{-1}$) the required force to inject the NMP samples was considerably higher reaching a maximum of 18±1 N and a minimum of 9±1.2 N.

Freeze-fracture replica was used to investigate the organization and morphology of the nanocrystals forming the thixotropic material. The stable NMP colloidal suspension was quickly frozen in liquid nitrogen (cooling rate >10$^5$ K s$^{-1}$) immobilizing the nanocrystals instantaneously (Acharya et al., Journal of International Oral Health 2014, 6, 36 1). The resulting frozen suspension was fractured, the ice was removed by vacuum freeze etching, and a thin layer of carbon was sputtered onto the surface to produce a carbon replica. The sample surface was shadowed with platinum vapor and the carbon-metal replica was put on a Formvar/Carbon coated copper mesh-200 grid (2SPI, Structure Probe Inc, West Chester, USA) and examined by Transmission Electron Microscopy (TEM) using a Tecnai T12 working at 120 kV (FEI Inc, Hillsboro, Oreg., USA). Selected Area Electron Diffraction and TEM imaging of the water dispersion of the NMP nanocrystals were performed on a TEM grid Formvar/Carbon coated copper mesh-200 grid (2SPI, Structure Probe Inc, West Chester, USA). The grid was prepared by deposition of a 5 μL drop of a 1% v/v water dispersion of the NMP gel, and the drop was blotted with filter paper after 90 seconds. Scanning Electron Microscopy (SEM) was used to characterize the nanocrystals at different time points during the reaction to obtain the NMP and the adhesion of osteoblast onto the surface of the nanocrystals. For time-point analysis, an aliquot of 2 mL was withdrawn from the reaction and poured into a Buchner filter, washed with water first (20 mL), ethanol (20 mL), and then dried in a vacuum oven at 25° C. This process was performed at 0.5, 5, 10, and 30 minutes from the beginning of the reaction. SEM was carried out using a FEI Inspect F-50 FE-SEM (FEI Inc, Hillsboro, Oreg., USA) operated at 10 kV. For osteoblast adhesion, cultures were fixed using a 2.5% glutaraldehyde solution for 20 minutes, and then dehydrated using a series of ethanol solutions from 50 to 100%. Afterwards, the samples were dried with ethanol/trichlorotrifluoroethane solutions using the subsequent ratios: 75/25, 50/50, 25/75, and 0/100 for 15 minutes and 0/100 until complete evaporation.

Figure 34:
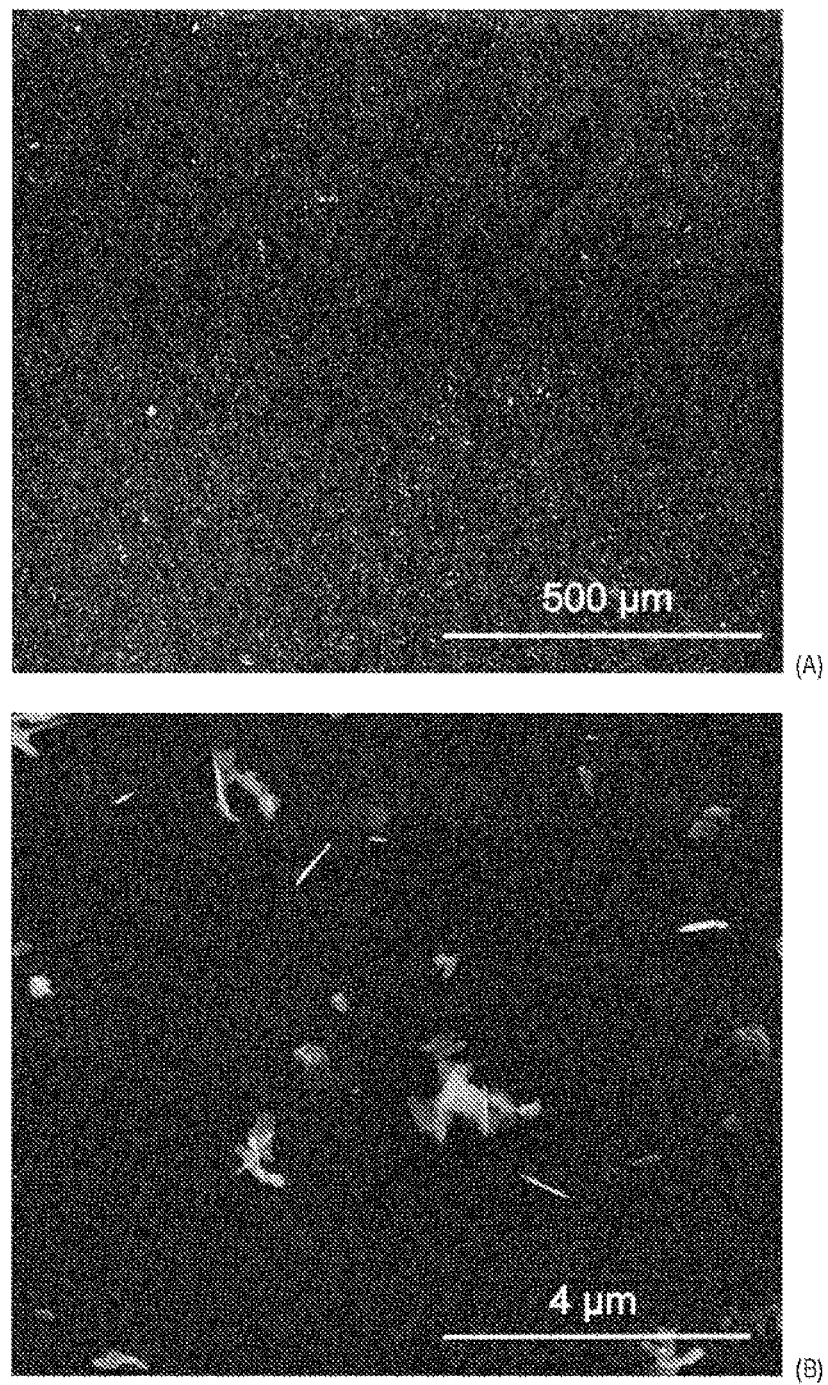
FIGS. 34 A and B show the deposition of NMP on a negatively charged glass surface.
Figure 35:
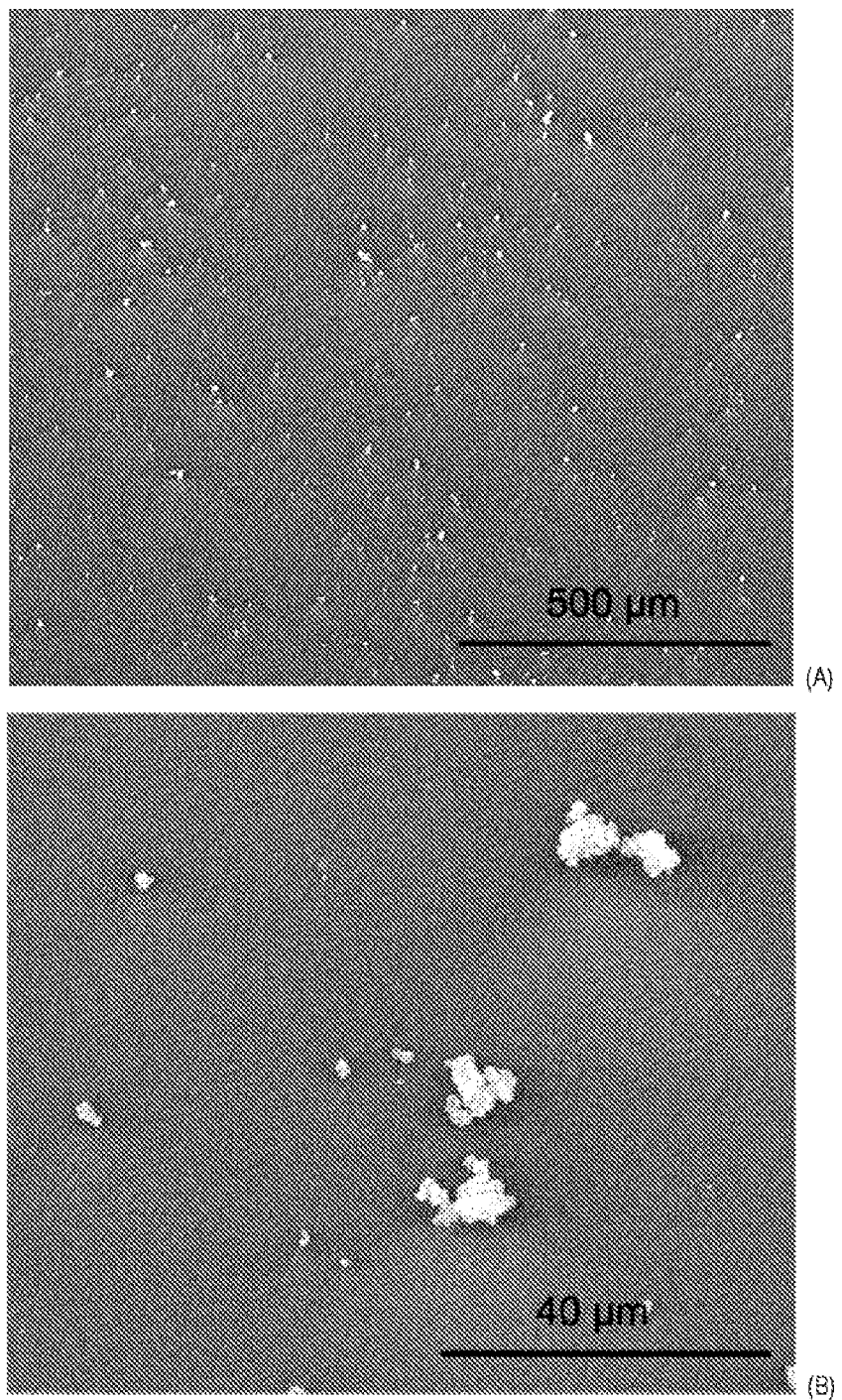
FIGS. 35 A and B show NMP powder deposited on a positively charged glass surface.

Zeta potential measurements were carried out to assess the superficial charge of the nanocrystals using a Malvern Nano ZS equipped with disposable folded capillary cells (Malvern Instruments Ltd, Malvern, UK). The concentration of the gel used in the measurements was 20 mg mL$^{-1}$ and the temperature was kept constant at 25° C. To assess the simultaneous presence of negative and positive charges, the interaction of the NMP nanocrystals with positively and negatively charged glass surfaces was studied (FIGS. 34 and 35). NMP nanocrystals were attracted to both positively and negatively charged glass surfaces. However, only negatively charged glass interacted with the edge of the nanocrystals indicating the presence of a positive charge on the edge of the NMP nanocrystals. Like clays, the simultaneous presence of positive and negative charges appears to allow the novel synthesized colloidal NMP dispersion to form a physical hydrogel with a "clay-like" behavior.

Surface Characterization

XPS measurements were carried out with a Thermo K-alpha spectrometer (Thermo Fisher Scientific Inc, East Grinstead, UK) equipped with monochromatic Al Kα X-rays source operating at 1486.6 eV. Due to the non-conductive nature of the powder composing the gel, the charging effect was minimized using a low-energy flood-gun to provide efficient charge neutralization. To preclude charging effects in the resulting spectra the binding energy (BE) scale was calibrated from the hydrocarbon contamination using the C1s peak at 285.0 eV. During the measurement, the residual pressure inside the analysis chamber was 1×10$^{-8}$ mbar. The survey spectra were recorded with an X-ray beam diameter size of 400 m and a passing energy of 200 eV, dwell time of 50 ms, and energy step size of 1 eV. High resolution spectra were recorded using a passing energy of 50 eV, dwell time of 50 ms, and energy step size of 0.1 eV. The surface depth profile experiment was realized using an Ar ions gun working at low current and ion energy of 500 eV that would produce an etching rate of 0.05 nm s$^{-1}$ on a surface of TaO$_2$. The etching time was 5 seconds and the process repeated for 5 times. Avantage software (5.932v) was used to fit photoelectron spectra using a least-squares algorithm. The background in narrow range spectra was accommodated by a nonlinear Shirley function, and the experimental curves were fitted using combinations of Gaussian and Lorentzian distributions (Aguzzi, C. et al., Appl Clay Sci. 2007, 36 (1-3), 22-36.) Quantification was performed on the basis of Scofield's relative sensitivity factors (AlAbbas, F. M. et al., Journal of Pipeline Engineering, 2012. 11(1): p. 63).

Biocompatibility of the NMP Colloidal Dispersions

Cell viability of NMP colloidal suspensions was carried out using primary human fibroblast (HF) cells. HFs were kindly provided by Dr. C. Doillon (Université Laval). HFs were derived from foreskins after written informed consent which was approved by the Centre Hospitalier Universitaire de Quebec (CHUQ) Ethics Committee. HFs were seeded on circular coverslips in 24 well-plate (0.8×105 well), cultured in DMEM cell culture media (10% FBS, 1% penicillin-streptomycin) at 37° C. in a humidified atmosphere of 5% CO$_2$ and grown overnight. A solution of 10% Alamar-Blue reagent was prepared in cell culture medium DMEM and used for the assay. HF cells without materials were used as positive control, NMP without HF cells was used as a blank, and colloidal suspension of formulation A and B were put in direct contact with HF cells for the cell viability test. After 1 day, the cell culture medium was removed and 500 µL of a 10% solution of Alamar-Blue reagent was added to each well and incubated at 37° C. in a humidified atmosphere of 5% CO$_2$ for 3 hours. From each sample 100 µL of culture medium was collected and deposited in a 96 well-plate. The fluorescence intensity was measured at 585 nm using a $\lambda_{exc}$ of 550 nm using a Microplate Reader SpectraMax M2 (Molecular Devices, L.L.C. Sunnyvale, Calif., USA). The same procedure was used for end point day 4 and 7.

Live/Dead Assay. HFs were seeded on circular coverslips in 24 well-plate (0.4×105 well), cultured in DMEM cell culture media (10% FBS, 1% penicillin-streptomycin) at 37° C. in a humidified atmosphere of 5% CO$_2$ and grown overnight. The staining solution was prepared mixing calcein (2 µmol L$^{-1}$), Etd-1 (4 mol L$^{-1}$), and Hoechst 33258 (4 g mL$^{-1}$). HF cells without materials were used as positive control, colloidal suspension formulation A and B were put in direct contact with HF cells for the Live-Dead assay. Negative control HF cells were treated with 70% of methanol for 30 minutes at room temperature. The culture medium was removed, and the cells were washed three times with 500 µL of phosphate buffer solution (PBS). 400 µL of the staining solution was added to each coverslip and incubated for 40 minutes at room temperature protected from light. Cells were washed again with PBS (500 µL) and the coverslips mounted on glass slides. Zeiss Axio Imager M2 (Carl Zeiss Microscopy GmbH, Goettingen, Germany) was used to take the photographs of the Live/Dead assay using three different sets of filters; green for calcein, red for Etd-1, and blue for Hoechst 33258. The same procedure was used for end point day 4 and 7. All assays were performed in triplicate.

Genes Expression of Osteoblast Differentiation

Mouse-derived bone marrow cells (mBMCs) were kindly provided by Dr. S. Komarova (McGill University). Animal experiments were performed in accordance with the McGill University guidelines established by the Canadian Council on Animal Care. Mouse-derived bone marrow cells (mBCMs) were collected from mouse tibia and femora using a procedure previously described (C57BL6/J, male, 6 weeks old, purchased from Charles River)—see Hussein et al., Bone 2011, 48, 202, incorporated herein by reference. mBMCs were cultured using a procedure previously described—see Tamimi et al., Acta Biomater. 2011, 7, 2678, incorporated herein by reference. Briefly, mBMCs were cultured in 75 cm$^2$ tissue culture flasks (2.5×10$^6$ cells cm$^{-2}$) in MEM (Wisent Inc., Canada) with 10% serum (Fisher Scientific, Canada), 1% penicillin/streptomycin antibiotics (Wisent Inc., Canada), 1% sodium pyruvate (Wisent Inc.) and 50 g mL-1L-ascorbic acid (Sigma-Aldrich Co., USA). After 7-10 days, cells were detached with trypsin/EDTA (Wisent Inc.) and plated at a density of 10$^4$ cells cm-2 directly onto the surface of the materials or the tissue culture treated polystyrene (Corning Life Sciences, Lowell, Mass., USA). mBMCs were cultured for 3, 5, 7, 14 and 21 days using MEM 10% serum, 1% antibiotics, 1% sodium pyruvate, 50 µg mL$^{-1}$ ascorbic acid, 10 mM glycerol 2-phosphate disodium salt hydrate, and dexamethasone 1×10$^{-9}$ M. Cell cultures were supplemented with fresh medium every second day. Total RNA was isolated from mBMC primary cultures using TRI-zol© reagent (Invitrogen™, USA) following the manufacturer's protocol and quantified in a spectrophotometer by absorbance readings at 260 nm. For real-time PCR, 1 g of total RNA from each sample was reverse transcribed using a high-capacity cDNA reverse transcription kit (Applied Biosystems, USA) in accordance with the manufacturer's instructions. The resulting cDNAs were used for real-time PCR using Power SYBR Green PCR Master Mix (Applied Biosystems). Reactions were carried out in a 7500 Real-time PCR System (Applied Biosystems) for 40 cycles (95° C. for 15 s, 60° C. for 30 s and 72° C. for 45 s) after the initial 10-minute incubation at 95° C. A cycle threshold value for each reaction was calculated using Applied Biosystems sequence detections software and the relative ratio of expression was determined using a previously described algorithm—see M. W. Pfaffl, Nucleic Acids Res. 2001, 29, incorporated herein by reference. Primers used to amplify specific targets are as follows: RunX2 (runt-related transcription factor 2: sense, 50-GGCTTGGGTTTCAGGTTAG-30 (SEQ ID NO: 1); antisense, 50-CGGTTTCTTAGGGTCTTGGA-30 (SEQ ID NO: 2)), TNALP (tissue nonspecific alkaline phosphatase: sense, 50-GGGGACATGCAGTATGAGTT-30 (SEQ ID NO: 3); antisense, 50-GGCCTGGTAGTTGTTGTGAG-30 (SEQ ID NO: 4)), COL1A1 (collagen type I, alpha 1: sense, 50-GAGGCATAAAGGGTCATCGTGG-30 (SEQ ID NO: 5); antisense, 50-CATTAGGCGCAGGAAGGTCAGC-30 (SEQ ID NO: 6)), OCN (osteocalcin: sense, 50-TGAACAGACTCCGGCG-30 (SEQ ID NO: 7); antisense, 50-GATACCGTAGATGCGTTTG-30 (SEQ ID NO: 8)), and OPN (osteopontin: sense, 50-CTGCTAGTACACAAGCAGACA-30 (SEQ ID NO: 9); antisense, 50-CATGAGAAATTCGGAATTTCAG-30 (SEQ ID NO: 10)).

In Vivo Study of Bone Healing and Implant Osseointegration

The in vivo part of this study was approved by McGill Ethics Board Committee in accordance to Canadian Council on Animal. This part was conducted on thirty-nine 10-12 week-old Sprague-Dawley rats (Charles River Laboratories, Montreal, QC). The rats were housed in Genome Animal facility of McGill University and caged in a controlled environment at 22° C. with 12-hour light/dark cycles and humidity of 50%. A rodent breeding diet and water were provided ad libitum. All rats were allowed to acclimatize to this environment for 2 weeks prior to surgical intervention.

Twenty-four animals were used to assess the effect of NMP gel on bone healing and implant osseointegration. These animals were divided into two groups; first control (12 rats) and; second NMP gel (12 rats). To provide sufficient analgesia during surgical procedure, rats were injected with Carprofen (5-10 mg/kg, subcutaneous, Pfizer Animal Health, Montreal, QC) thirty minutes prior to surgical intervention. The rats were anesthetized with isoflurane (4% during the induction and 2.5% during the surgical procedure); the legs were shaved, disinfected with chlorhexidine gluconate solution (Omega Laboratories, Montreal, Canada) and covered with a sterile drape. A full thickness incision was made to expose the proximal third of the tibia. A uni-cortical defect (2.5 mm ø) was created in the right tibia using straight hand-piece under constant saline irrigation. The same procedure was performed in the contralateral side but custom made titanium (Ti) implant (1.5 mm ø×2.0 mm in depth) was placed in the defect. In NMP group, the Ti implants were coated with NMP gel before insertion in the defect and the contralateral defects were filled with the NMP gel (20 µL). The implant and the defects were not treated in the control group. Incisions were sutured using 5-0 monocryl sutures. In order to provide sufficient analgesia to the rats following surgery, they were administered with Carprofen every 24 hours for the first 3 days. Rats were allowed to heal for two weeks and then were euthanized using $CO_2$ asphyxiation, and the tibiae were extracted and preserved in 10% neutral buffered formalin (Richard Allan Scientific, Kalamazoo, Mich.). Samples were code labeled and codes were blinded to the person who did the analyses.

Micro-CT

Since the introduction of metallic implants for medical use by Branamark in 1981 (ref), histology has beenc considered the most accurate method for assessing osseointegration. However, histology has several limitations: it only allows two-dimensional assessment, it is expensive, multi-step processing may be expensive, and it destroys the sample. Therefore, µ-ct was introduced as a method for bone volumetric analysis. However, it had disadvantages too since assessment of the bone surrounding implants was not possible due to difference in densities between the bone and the metallic implant. Here, we introduce a new method to assess osseointegration using µ-ct. The right tibiae (bone defect samples) were scanned using a micro-CT (SkyScan1172; SkyScan; Kontich, Belgium) set at 12.7 µm resolution, 50 kV voltage, 200 µA current, 0.5 degree rotation step and 0.5 mm aluminum filter. The original bone defect (2.5 mm 0, full thickness of cortex) was identified as a region of interest (RO). The ROI was analyzed and the volume of the defect was calculated by subtracting the bone volume from the total volume of the ROL.

The left tibiae samples with Ti implants were also scanned using a micro-CT (SkyScan1172; SkyScan; Kontich, Belgium) but set at 4.5 µm resolution, 100 kV voltage, 100 pA current, 0.4 degree rotation step and aluminum/copper filter. The reconstructed images were segmented by different thresholding to obtain two ROIs. The first ROI included the titanium implant only by thresholding the intensity of the white color at low 80 and high 255. The second ROI included the implant/bone in the peri-implant area by an exact dilation of the the first ROI and followed by thresholding the intensity of the white color at low 10 and high 255. The final ROI (the peri-implant bone) was determined by subtracting the first ROI from the second ROI and the bone peri-implant area was analyzed.

Gene Expression of in vivo Study

Twelve rats were used to assess the effects NMP gel on RunX2 and COL1A1 gene expression. Two uni-cortical defects (2.5 mm ø) were created in both tibiae. The right tibial defect was administered with NMP gel while the contralateral side was left empty. COL1A1

Primers used to amplify specific targets are as follows: RunX2 (runt-related transcription factor 2: sense, 50-GGCTTGGGTTTCAGGTTAG-30 (SEQ ID NO: 1); antisense, 50-CGGTTTCTTAGGGTCTTGGA-30 (SEQ ID NO: 2)), TNALP (tissue nonspecific alkaline phosphatase: sense, 50-GGGGACATGCAGTATGAGTT-30 (SEQ ID NO: 3); antisense, 50-GGCCTGGTAGTTGTTGTGAG-30 (SEQ ID NO: 4)), COL1A1 (collagen type I, alpha 1: sense, 50-GAGGCATAAAGGGTCATCGTGG-30 (SEQ ID NO: 5); antisense, 50-CATTAGGCGCAGGAAGGTCAGC-30 (SEQ ID NO: 6)), OCN (osteocalcin: sense, 50-TGAACAGACTCCGGCG-30 (SEQ ID NO: 7); antisense, 50-GATACCGTAGATGCGTTTG-30 (SEQ ID NO: 8)), and OPN (osteopontin: sense, 50-CTGCTAGTACACAAGCA- GACA-30 (SEQ ID NO: 9); antisense, 50-CATGAGAAAT-TCGGAATTTCAG-30 (SEQ ID NO: 10)).

Bone Healing and Osseointegration

Samples with bone defects were dehydrated in ascending concentrations of ethanol (70-95%). Three sections obtained and stained with either tartrate resistance acid phosphatase (TRAP) to assess the number of osteoclasts, alkaline phosphatase (ALP) to assess the effects on the osteoblast number, and Von Kossa to assess the mineralization. Histological sections were recorded using an optical microscope (Carl Zeiss Microscopy, Germany). The number of osteoclasts and osteoblasts were quantified using an imaging software (ZEN 2012 SP2, Germany). Osteoclasts data were presented as osteoclast number per square millimeter of mineralized tissue ($OC/mm^2$). Similarly, the osteoblasts data were presented as osteoblasts number per square millimeter of mineralized tissue ($OB/mm^2$). The percentage of mineralized tissue in the defect was analyzed using Image J (Wayne Rasband; National Institute of Health, Bethesda, Md.) and data were presented as mineralized tissue present (MT %). All data are presented as mean±standard deviation. Left tibiae samples with Ti implants were dehydrated in ascending concentrations of ethanol (70%-100%) and infiltrated with poly(methyl-methacrylate) histological resin (Technovit 9100, Heraeus Kulzer, Wehrheim, Germany). After polymerization, samples were sectioned into 30 μm thick histological slides using a diamond saw (SP1600, Leica Microsystems GmbH, Wetzlar, Germany) and stained using basicfuchsine and methylene blue. Histological sectionswere imaged using an optical micro-scope (Carl Zeiss Microscopy, Germany) and analyzed using ImageJ software (Wayne Rasband; National Institute of Health, Bethesda, Md.). The bone-implant contact was calculated by dividing the bone-covered implant perimeter by the total implant perimeter.

Statistical Analysis

The sample size for the in vivo part of the study was calculated to give a power of 80% at 95% confidence level to reject the null hypothesis that there is no difference between NMP gel-coated and non-coated implants. A 10% difference was considered to be clinically relevant, 12% potential standard deviation was assumed based on previous study, and a 10% potential drop-out was expected (based on our previous experiment using similar model and intervention). Shapiro-Wilk test was used to assess data normality and Student's t test was used to compare between groups. Origin 9 software (Origin Lab Co., Northampton, Mass.) was used for data analyses. Statistical significance was set at $p<0.05$.

Results

Identification, Characterization, nanocrystals morphology and structure of the NMP phase The novel 2D Nanocrystalline Magnesium Phosphate (NMP) biomaterial is identified in the ternary diagram of the system $NaOH—Mg(OH)_2—H_3PO_4$ (FIG. 2).

Figure 3:
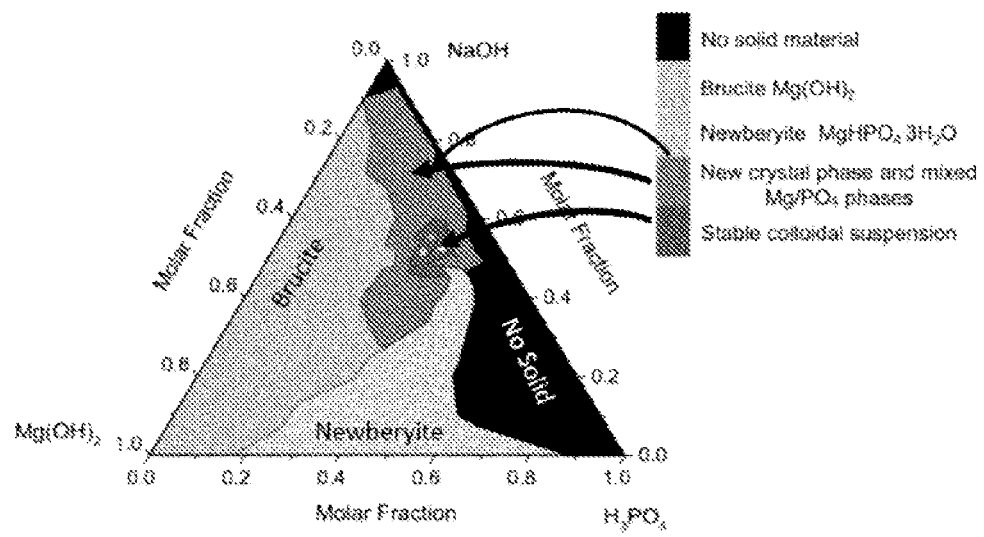
FIG. 3 shows the ternary diagram of the Mg(OH)$_2$—NaOH—H$_3$PO$_4$ system with the different phases obtained by mixing the three components at different mole fractions.

NMP gels were obtained in a small region of the ternary diagram (FIG. 3, area labelled "Stable colloidal suspension"). The symbols on this area of the ternary diagram refer to specific formulations A=▲, B=♦, C=■, and D=⊛ reported in Table 2. ▲♦

Figure 4:
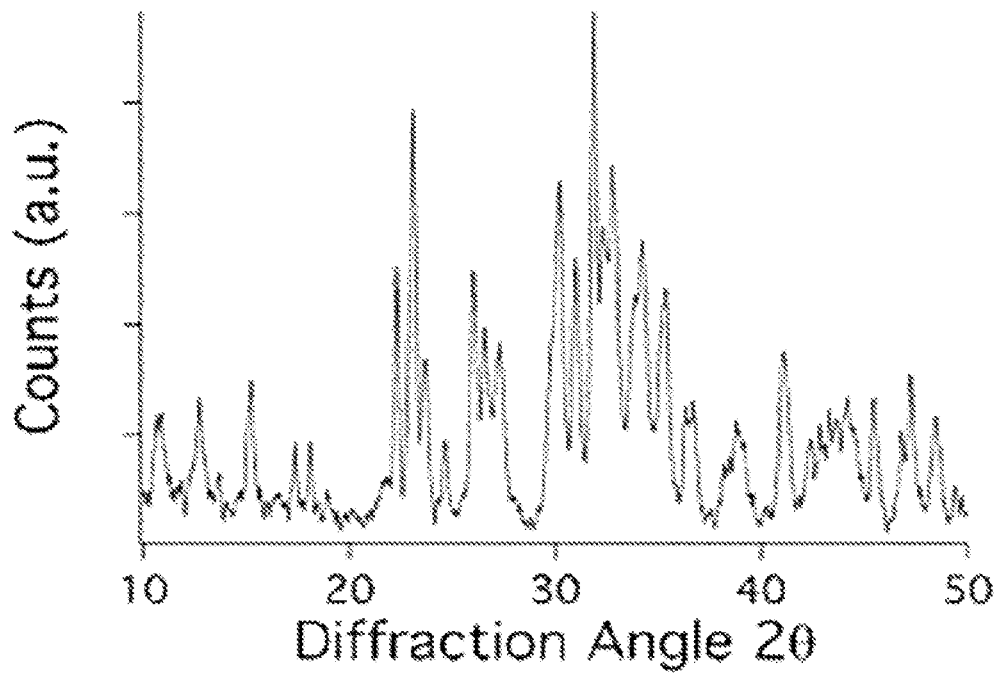
FIG. 4 shows the X-ray diffraction pattern of a new unidentified crystalline phase obtained in the are a labelled "New crystalline phase and mixed Mg/PO$_4$ phases in FIG. 3.

Depending on the mole fractions used, the remaining crystals phases identified ranged from di- and tribasic magnesium phosphate such as Newberyite $MgHPO_4.3H_2O$, Farringtonite $Mg_3(PO_4)_2$, Bobierrite $Mg_3(PO_4)_2.8H_2O$, and Brucite $Mg(OH)_2$. In addition, a new unidentified crystal phase (X-ray diffraction pattern shown in FIG. 4) and unstable gel-like colloidal suspension were obtained (FIG. 3, are a labelled "New crystal phase and mixed $Mg/PO_4$ phases" surrounding the area labelled "Stable colloidal suspension").

Solutions with a mole fraction (η) of $H_3PO_4$ higher than 0.8 were too acidic and no precipitates were obtained (see FIG. 3, black area on the right hand side of the diagram).

The composition of the NMP was comprised of a range of $[Mg^+]$, $[Na^+]$, $[PO_4^{3-}]$, and $[HPO_4^{2-}]$ and the formula can be assumed to be $Mg_XNa_Y(HPO_4^{2-})_Z.(PO_4^{3-})_T.nH_2O$ with [5≤X≤7], [1≤Y≤2], [3≤Z≤5], and [1≤T≤3] where [7≤X+Y≤8] and [5≤Z+T≤6].

Figure 5:
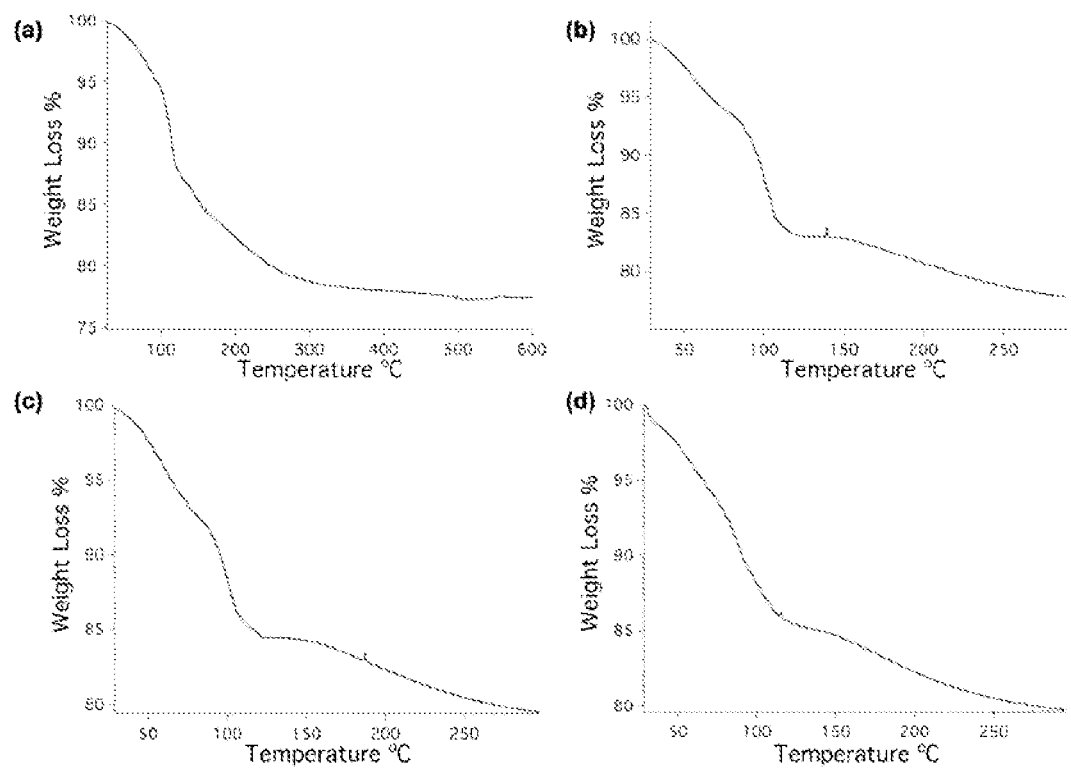
FIG. 5 shows the thermogravimetric analysis of the different formulations: from a to d—Formulations A, B, C, and D, respectively.

The crystallization water was determined by thermogravimetric analysis and was comprised between [3≤n≤4] (Table 2 and FIG. 5).

TABLE 2

Composition of the four different formulations obtained as stable colloidal suspension measured using ICP-OES. The amount of water of the dried powder was determined using TGA. The symbols refer to specific formulations showed in the area labelled "Stable colloidal suspension" in FIG. 3.

| Formulation | Mole fraction $H_3PO_4$/NaOH/$Mg(OH)_2$ | Atomic % P | Atomic % Na | Atomic % Mg | pH |
|---|---|---|---|---|---|
| A ▲ | 0.35/0.52/0.13 | 16.2 ± 1.3 | 6.5 ± 0.2 | 17.5 ± 0.4 | 8.3 ± 0.1 |
| B ♦ | 0.37/0.45/0.18 | 19.5 ± 2.3 | 3.3 ± 0.4 | 19.5 ± 2.2 | 7.8 ± 0.1 |
| C ■ | 0.3/0.55/0.15 | 20.3 ± 3.0 | 3.4 ± 1.0 | 24.7 ± 3.5 | 10.9 ± 0.1 |
| D ⊛ | 0.3/0.52/0.18 | 20.4 ± 1.5 | 3.2 ± 1.5 | 22.2 ± 1.8 | 10.8 ± 0.1 |

The atomic ratio Mg/P was between 1 and 1.15, suggesting that the NMP gel might present similarity with the crystalline precipitate Newberyite $MgHPO_4.3H_2O$.

Figure 6:
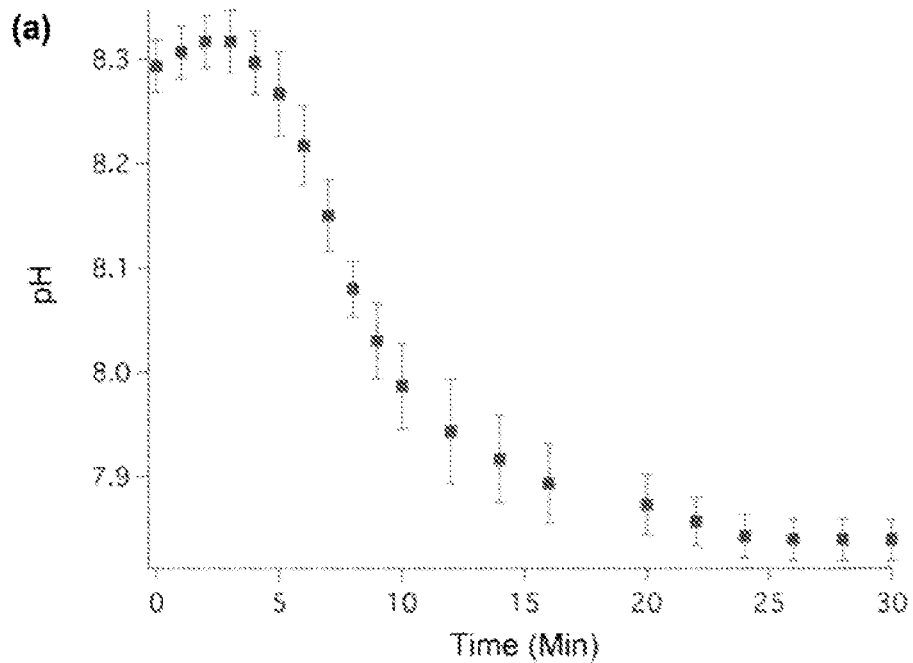
FIG. 6 shows the pH of the colloidal suspension as a function of the reaction time.

The evolution of various physical aspect of the NMP colloidal suspension during the synthesis was as follows. FIG. 6 shows the pH of the colloidal suspension as a function of the reaction time. The mole fraction of $H_3PO_4$/NaOH/$Mg(OH)_2$ was 0.37/0.45/0.18 and the total volume was 7 mL. FIG. 7 is a picture of the suspension after 30 seconds from the beginning of the reaction. The colloidal suspension was white and liquid, visible by tilting the tube. FIG. 8 shows that after 10 minutes, the NMP colloidal suspension transformed from liquid to solid changing its color from white to gray. Finally, FIGS. 9 A and B show the NMP nanocrystals evolution during the reaction. The SEM micrographs show the evolution of the morphology nanocrystals after 30 s (d) and 30 minutes (e). The scale bar represents 500 nm.

The zeta potential of the NMP nanocrystals showed an overall negative charge comprised between −10.1±4.3 and −18.1±6.7 mV.

Rheological measurements confirmed the thixotropy of the NMP colloidal suspension with a solid content of 5-10 wt. % (FIGS. 10 to 14). After liquefaction (G'≤G"), $t_L$-G is the time taken for G', G" and θ to return to their original levels when shear stress is removed.

At low stress the material remained in solid state, as indicated by G'>G" (δ<45°), and upon increasing stress it started to liquefy (G'=G" and θ=45°). The minimum shear stress required for this to occur is defined as the liquefaction stress $\tau_y$, and its value ranged between 22 and 127 Pa. The increase of $\tau_y$ and viscosity is usually attributed to the increasing number and extent of interactions between the nanocrystals due to their growing association. After stress removal, the material recovered the gel-like state with a recovery time ($t_{L-G}$) as quick as 12 s which is faster than water dispersion of 2D clay Laponite (20 minutes). T varied according to the viscosity because Brownian motions are inversely proportional to the medium viscosity; higher viscosity decreased the mobility of the nanocrystals increasing the $t_{L-G}$ needed to reform the original 3D network.

In addition, viscosity was inversely proportional to the size of the nanoparticles, so by varying the mole fraction of the three components it was possible to modify the rheological and physical properties of the NMP suspensions (Table 3).

Figure 17:
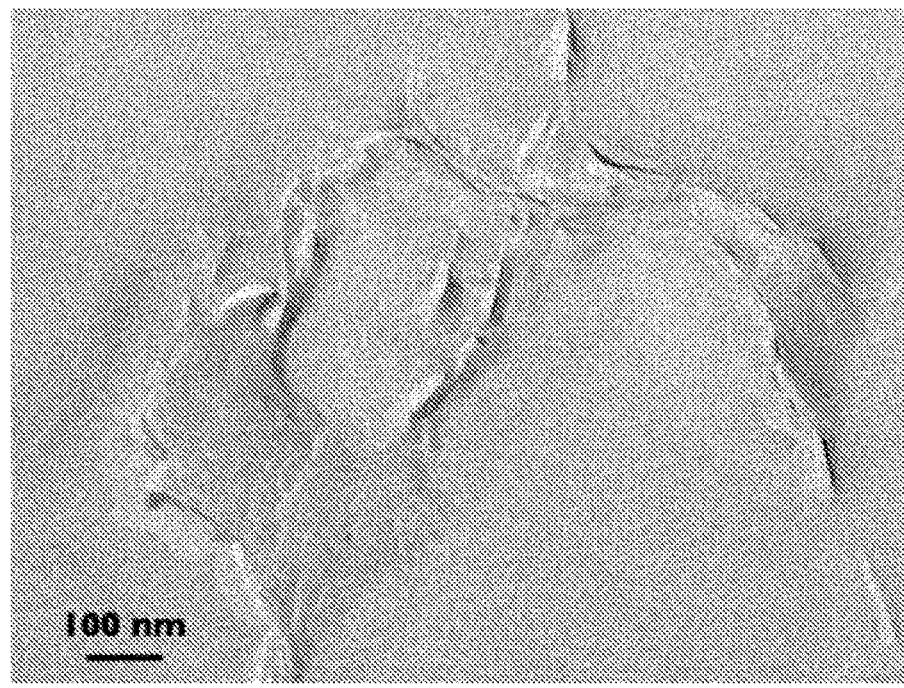
FIG. 17 is a high magnification TEM micrograph of the carbon-platinum replica grid showing the laminar structure of the ultra-thin nanocrystals of formulation A with a face-to-face arrangement and a thickness of 4-7 nm.
Figure 18:
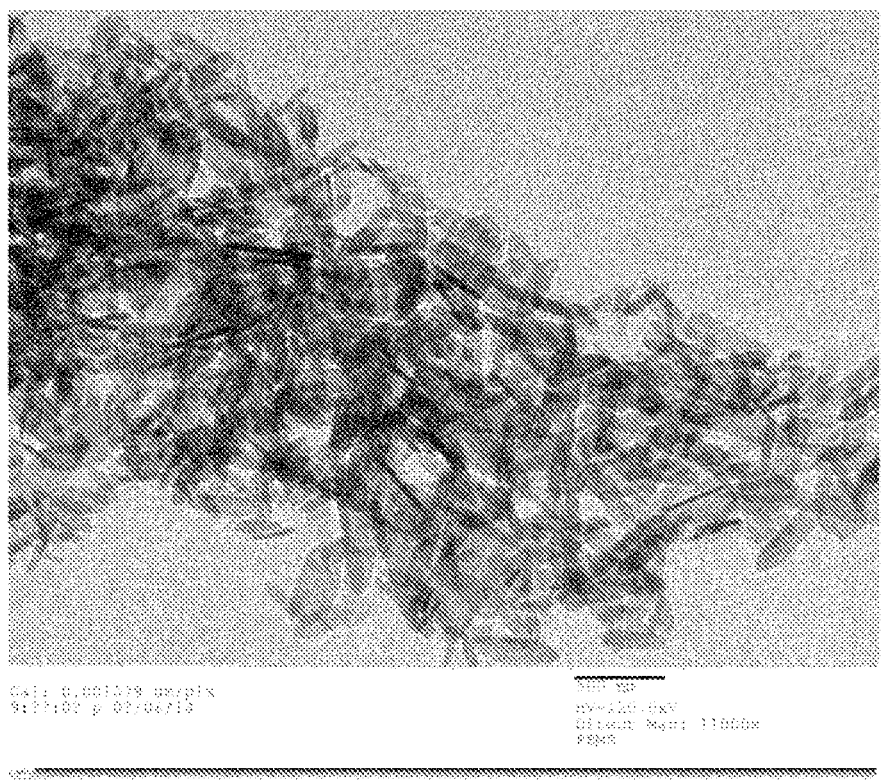
FIG. 18 is a TEM micrograph of the NMP colloidal suspensions of Formulation A.
Figure 19:
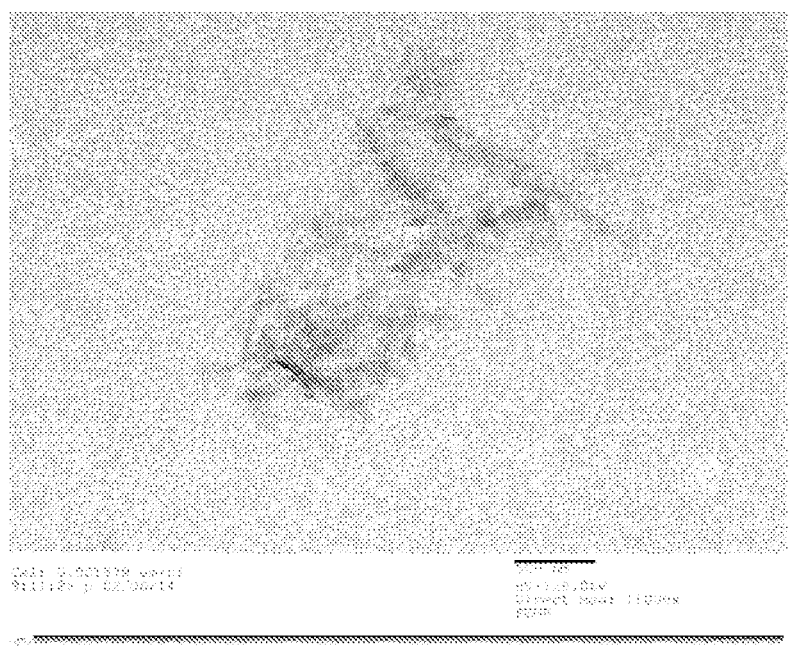
FIG. 19 is a TEM micrograph of the NMP colloidal suspensions of Formulation B.
Figure 20:
FIG. 20 is a TEM micrograph of the NMP colloidal suspensions of Formulation C.
Figure 21:
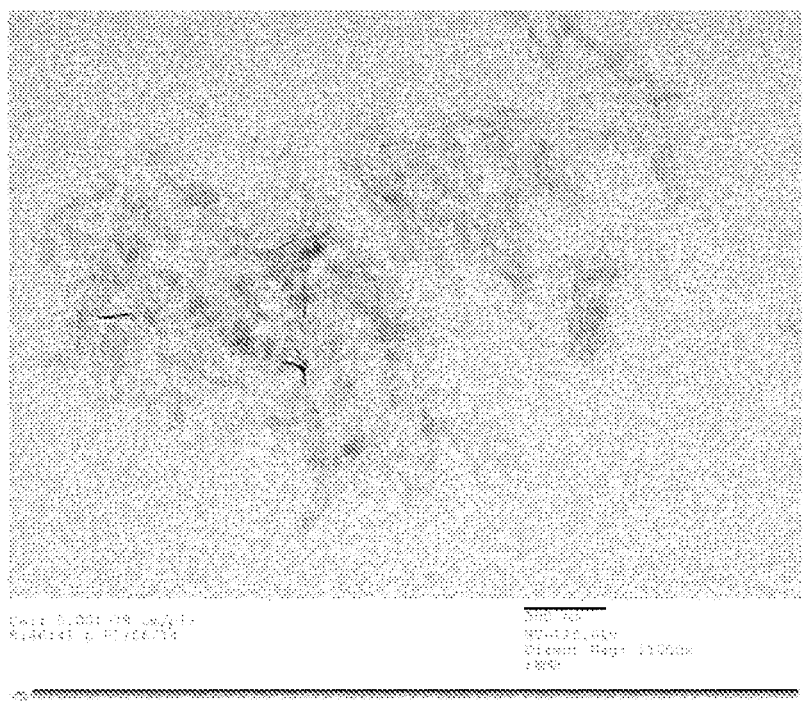
FIG. 21 is a TEM micrograph of the NMP colloidal suspensions of Formulation D.
Figure 22:
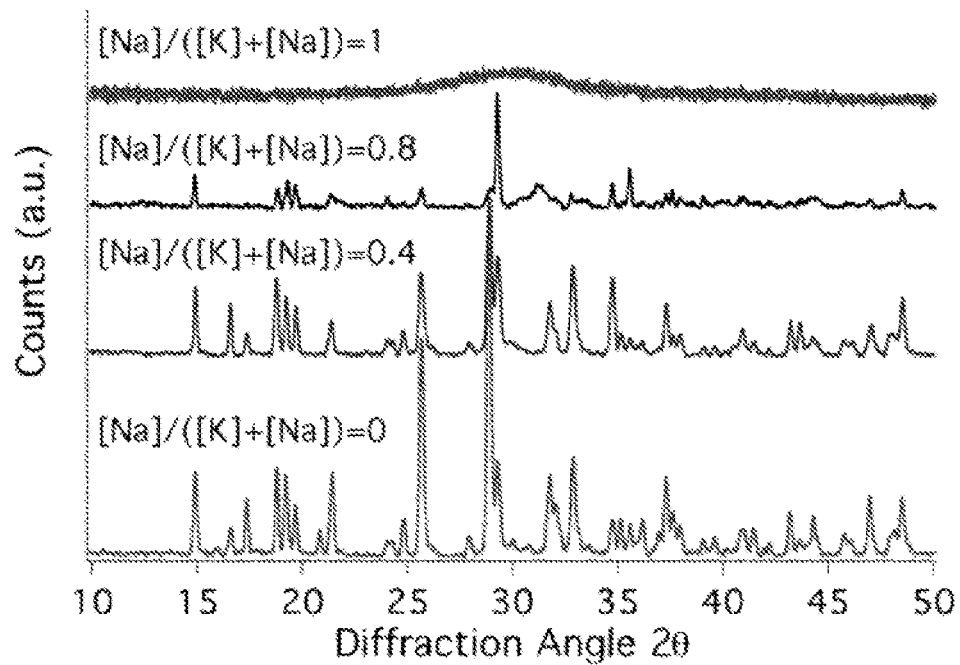
FIG. 22 shows the XRD patterns of different powders showing the partial or total conversion of nanocrystalline NMP into crystalline Newberyite.
Figure 23:
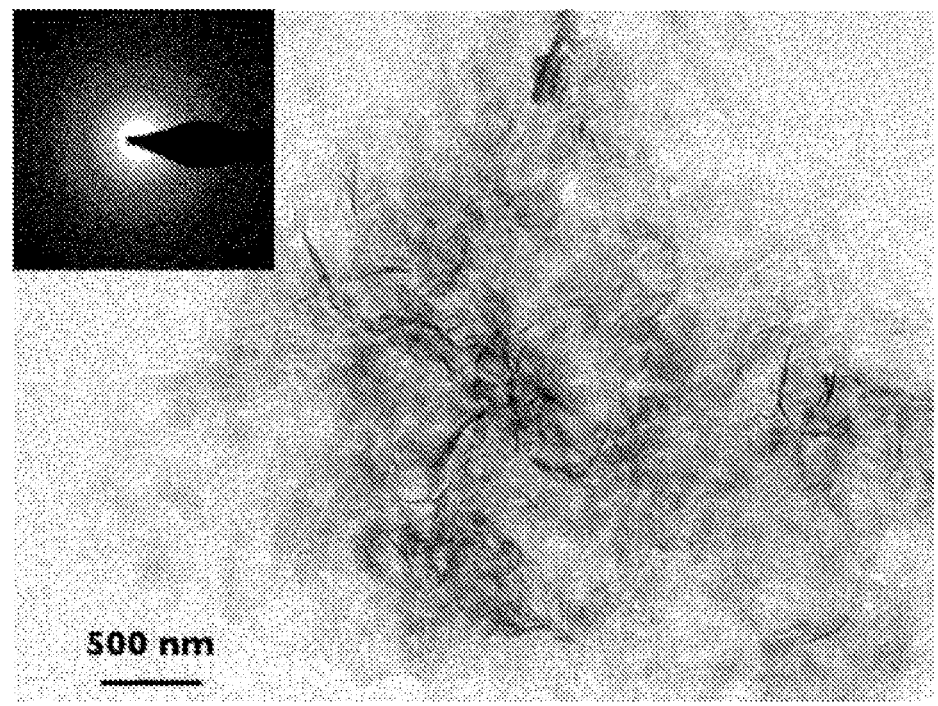
FIG. 23 is a TEM micrograph of a NMP colloidal dispersion of formulation A with a concentration of 1% v/v in water (In the inset, selected area electron diffraction (SAED) shows the nanocrystallinity of the NMP nanocrystals.)

One of the models used to explain thixotropy is the aforementioned "house of cards", where the particles are held together by edge-to-face contacts due to the simultaneous presence of positive and negative charges on the edge and face of the particles. High magnification TEM micrograph reveals that the type of aggregation of the nanocrystals mainly consist of face-to-face associations. The nanocrystals partially overlap each other resulting in a honeycomb network of an extended sheet-like face-to-face aggregates that are bent, twisted, branched, and intertangled with few edge-to-face contacts (FIGS. 17 and 23).

Figure 24:
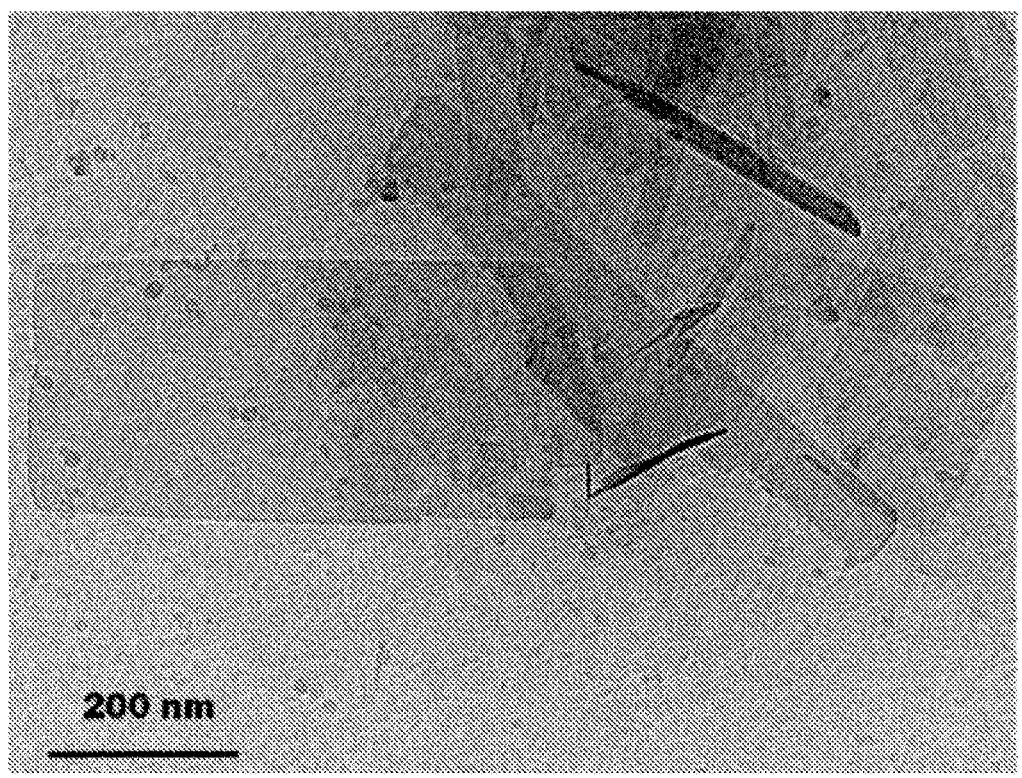
FIG. 24 is a Titan Krios micrograph of the NMP gel of formulation A showing the very thin structure of the 2D nano-sheet.

The very thin structure of the 2D nano-sheet is visible on the Titan Krios micrograph of the NMP gel (FIG. 24).

Sodium Ions Stabilize NMP Nanocrystals

Figure 25:
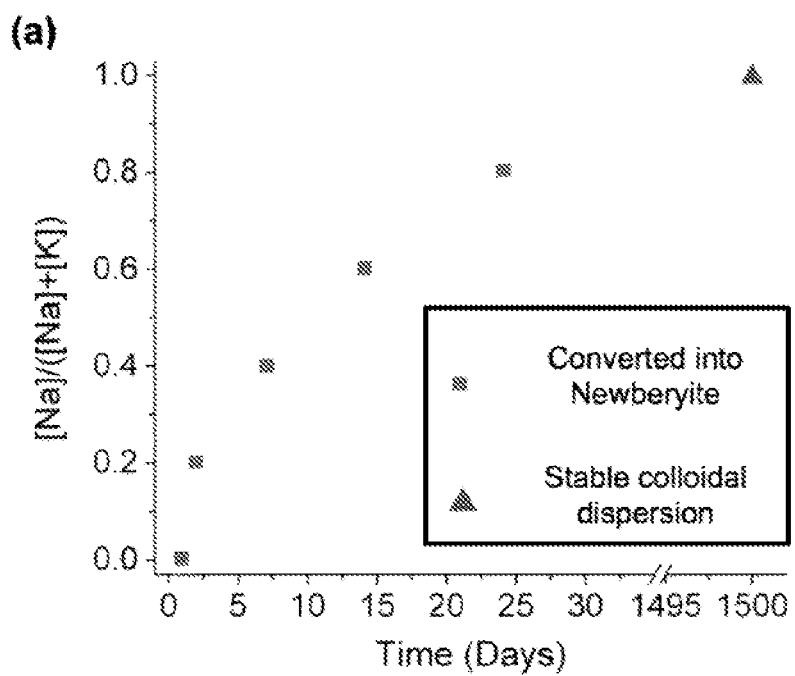
FIG. 25 shows the stability of the thixotropic suspension over time as a function of the ratio [Na]/([Na]+[K]
Figure 28:
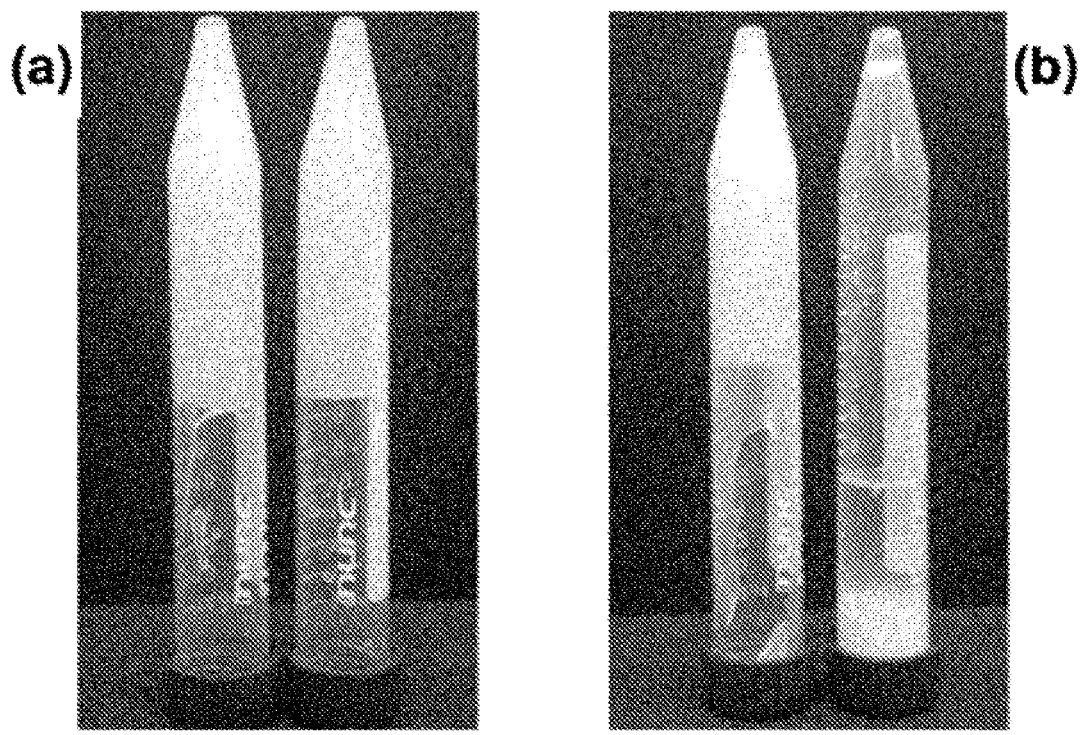
FIG. 28 shows vials tubes with the colloidal dispersions (a) after the synthesis and (b) after 3 days—the gel synthesized using LiOH (on the left in both pictures) remained stable while the gel using KOH (on the right) lost its stability and converted into Newberyite ($MgHPO_4.3H_2O$)

The synthesis of the thixotropic NMP biomaterial was achieved using different alkaline bases (NaOH, KOH, and LiOH) and the material showed very long term stability (>1500 days, 20° C.). However, the stability was dramatically influenced by the type of alkali ion used. Smaller ions such as $Li^+$ and $Na^+$ (ionic radius 76 and 102 μm, respectively) produced stable hydrogels, whereas larger $K^+$ ions (ionic radius 138 μm) resulted in unstable hydrogels that eventually converted to Newberyite $MgHPO_4.3H_2O$ (FIG. 28). The replacement of $Na^+$ with $K^+$ ions affected the stability of the suspension that decreased from >4 years to <1 day resulting in a quick conversion of NMP to Newberyite (FIG. 25); the speed of conversion was directly correlated to the ratio [Na]/([K]+[Na]). The stable NMP

TABLE 3

Physical properties of NMP hydrogels synthesized with different mole fractions.

| Formulation | Mole fraction $H_3PO_4/Mg(OH)_2$ | Crystal Size L × W (nm) | Zeta Potential (mV) | Storage Modulus G' (Pa) | Liquefaction Stress Ty (Pa) | $t_{L-G}$ |
|---|---|---|---|---|---|---|
| A | 2.7 | 285 ± 133 × 54 ± 18 | −10.7 ± 0.5 | 1769 | 22 | 12 s |
| B | 2.1 | 237 ± 83 × 64 ± 25 | −10.1 ± 4.3 | 4316 | 56 | 60 s |
| C | 2 | 156 ± 84 × 39 ± 8 | −17.4 ± 5.5 | 5199 | 80 | 95 s |
| D | 1.6 | 141 ± 82 × 39 ± 12 | −18.1 ± 6.7 | 10540 | 127 | >300 s |

Figure 15:
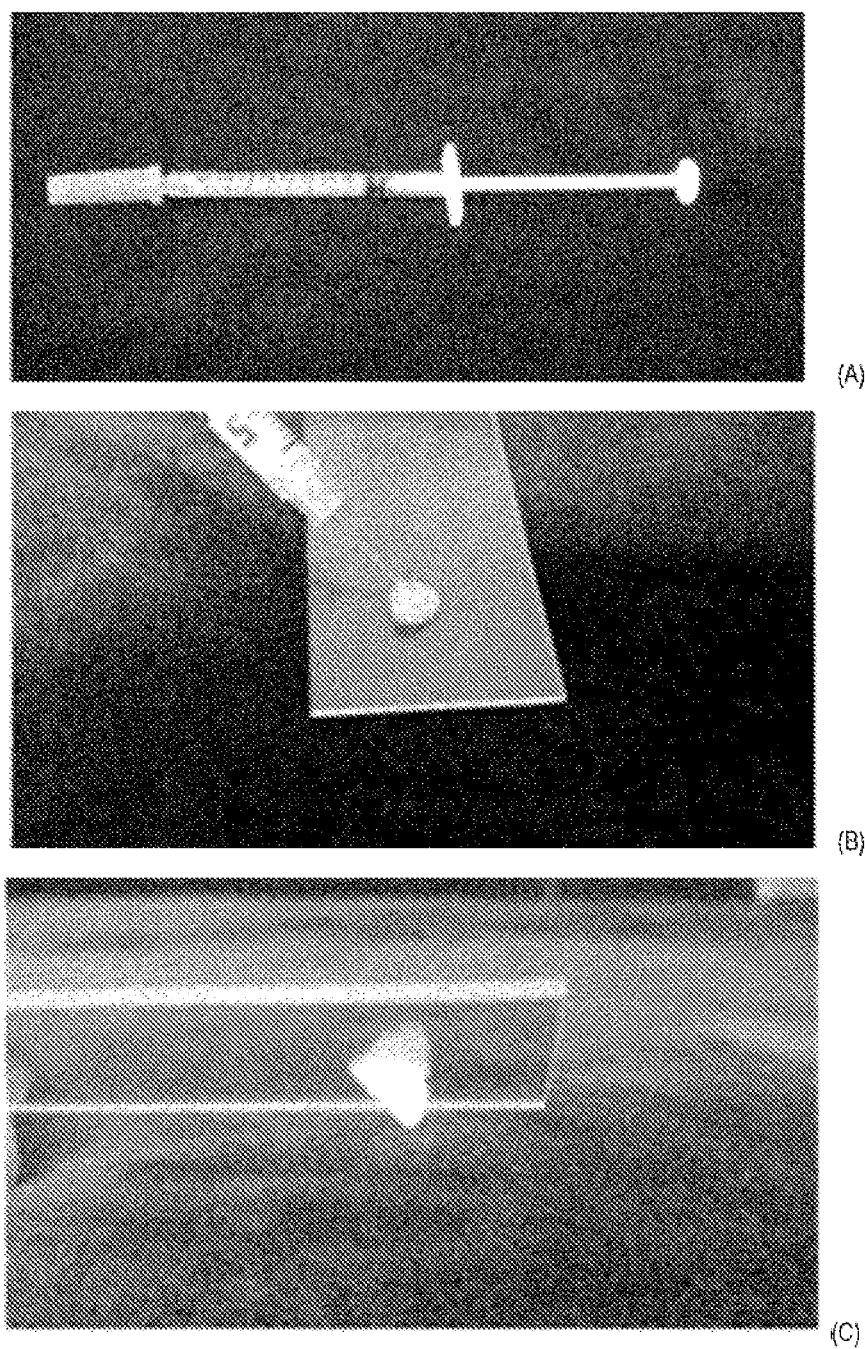
FIG. 15 shows the physical aspect of the NMP suspension (A) in a syringe, (B) while injected through an insulin needle (160 μm internal diameter), and (C) after injection.

The NMP gel could be injected easily through an insulin needle and after manual injection the colloidal suspension would regain solid-like behavior (FIG. 15). The force required to inject the NMP material through the insulin needle was only 0.08-0.63 N more than the force required to inject water (0.14±0.03 N Experimental Section, above). After flipping the glass slide, the suspension behaved like a solid material.

Figure 16:
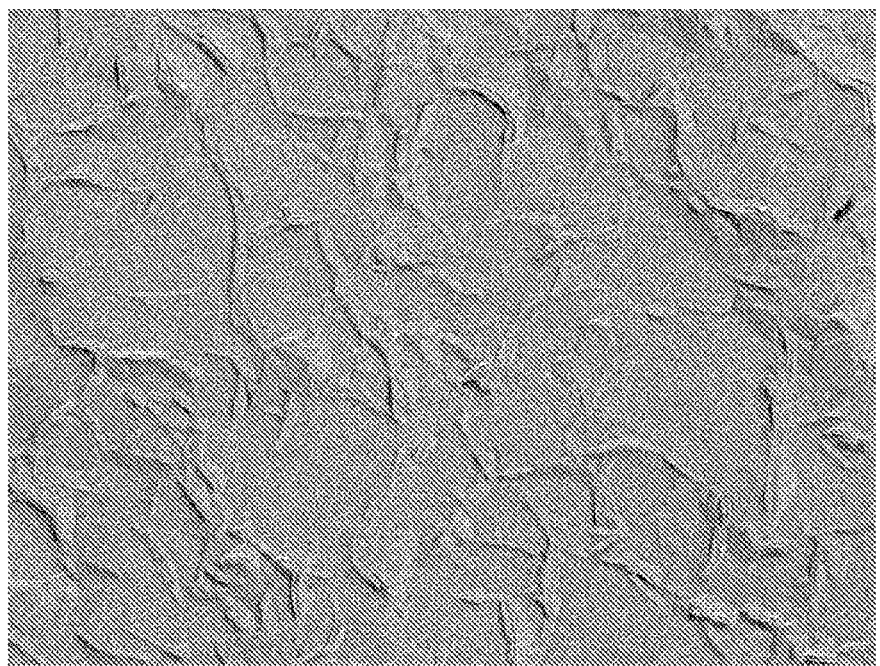
FIG. 16 is a representative TEM micrograph of a freeze-fractured carbon-platinum replica of a 5% w/w NMP suspension.

The real 3D structure of the colloidal suspension was revealed with TEM freeze-etching fracture technique due to the inherent sample technique preparation. The nanocrystals are kept in place by the underlying ice matrix, and after being exposed for replication, the carbon-metal replica shows the network formed by the nanocrystals. Low magnification TEM micrograph of the carbon-metal replica of a freeze-fractured suspension shows bundled NMP nanocrystals forming the 3D network, the water composing the medium of the hydrogel being in the empty space between the bundled nanocrystals (FIG. 16). The surface of the replica showed a stepped pattern revealing the thickness of the nanocrystals that was estimated to range between 4 and 7 nm (FIG. 17).

Figure 26:
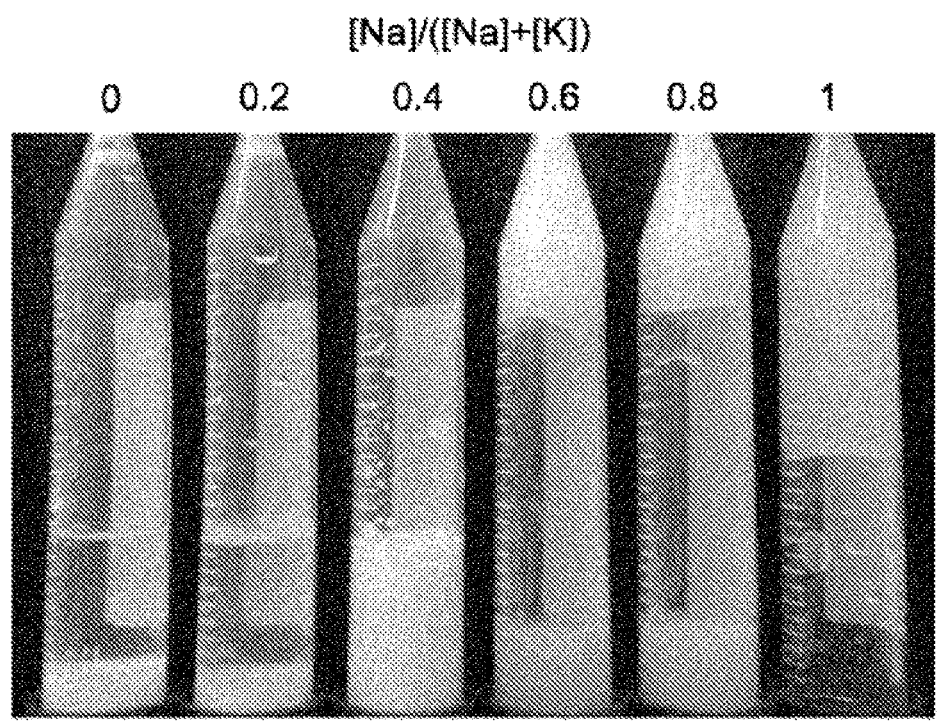
FIG. 26 shows the physical aspect after one week of NMP suspensions with different ratios of [Na]/([Na]+[K])
Figure 27:
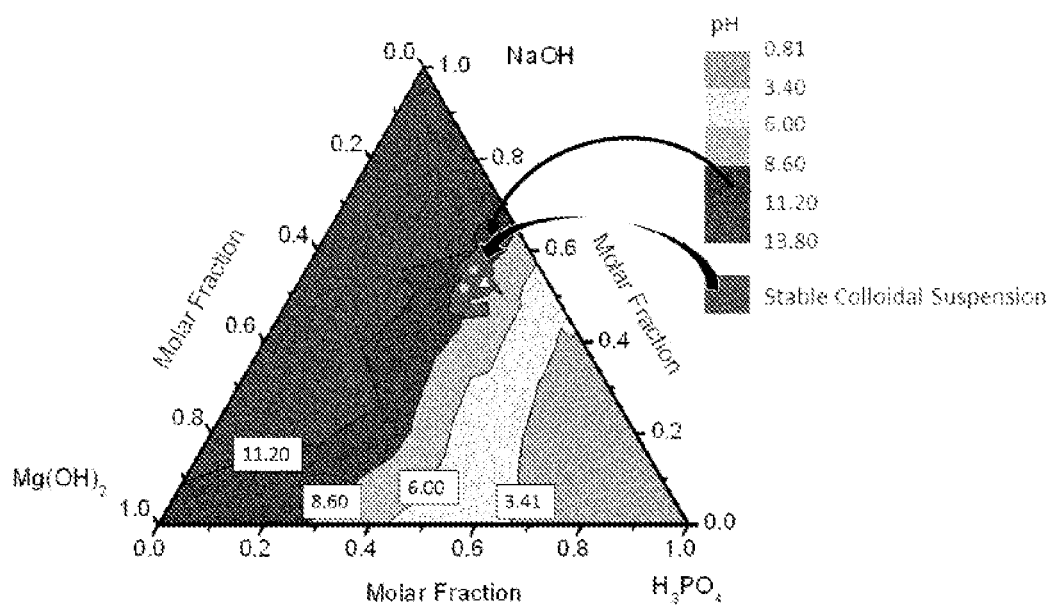
FIG. 27 shows the ternary diagram of the pH as a function of the mole fraction of $Mg(OH)_2$, $NaOH$, and $H_3PO_4$.

TEM micrographs illustrated the high aspect ratio of the nanocrystals, and selected area electron diffraction showed the nanocrystalline nature of the biomaterial (FIGS. 18 to 22).

suspension made with sodium remained in the gel state and it had no phase change after 4 years as shown by XRD (FIG. 26). Both NMP and Newberyite have similar Mg/P ratio, they form in a similar pH range 6.4-9.4 (FIG. 27, arrows).

NMP contains both $HPO_4^{2-}$ and $P_4^{3-}$. This was demonstrated by performing onto the washed NMP powder FT-IR, solid state magic angle spinning (MAS) NMR, and XPS.

Figure 29:
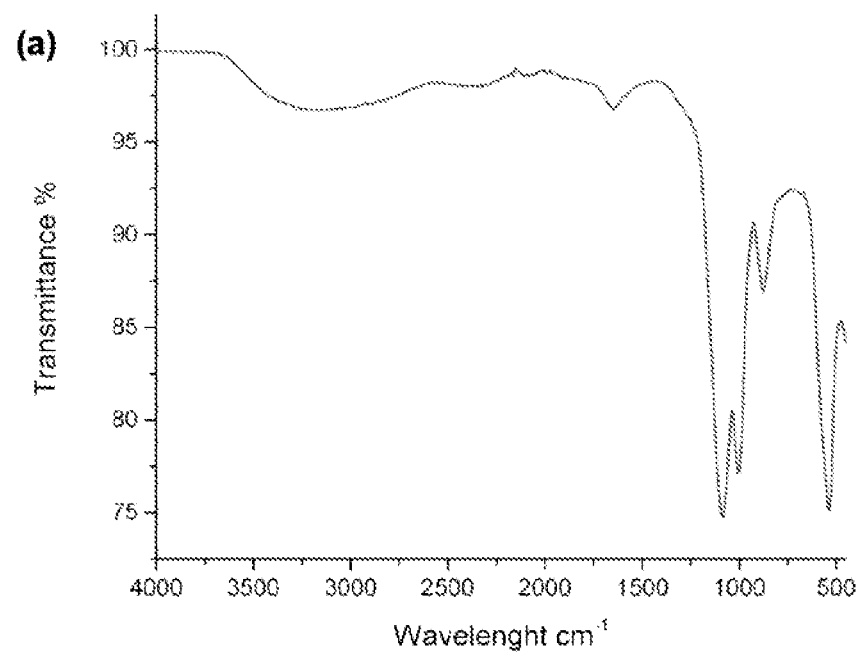
FIG. 29 shows the FT-IR spectrum of the dried and washed NMP powder of formulation A.

The FT-IR spectrum of formulation A (FIG. 29) showed a broad absorptions band from 3600 to 2600 $cm^{-1}$, indicating a combination of 0-H stretching of intermolecular and weakly bonded crystallization water and stretching of (P)O—H. As in other hydrogen phosphates (e.g. Monetite $CaHPO_4$) the OH stretching of the $HPO_4^{2-}$ anion give rise to at least two broad bands around 2855 and 2385 $cm^{-1}$. The band around 2855 $cm^{-1}$ was covered by the broad absorption of the water molecules, while the band at 2355 $cm^{-1}$ was visible. The broad absorption at 1647 $cm^{-1}$ was also attributed to a combination of HOH bending and rotation of residual crystallization and free water. The absorptions bands at 1080 and 1005 $cm^{-1}$ were associated with the stretching vibrations of P=O, the band at 875 $cm^{-1}$ was attributed to the bending of P—O—H, while the band at 535 $cm^{-1}$ was attributed to the bending of P=O.

Figure 30:
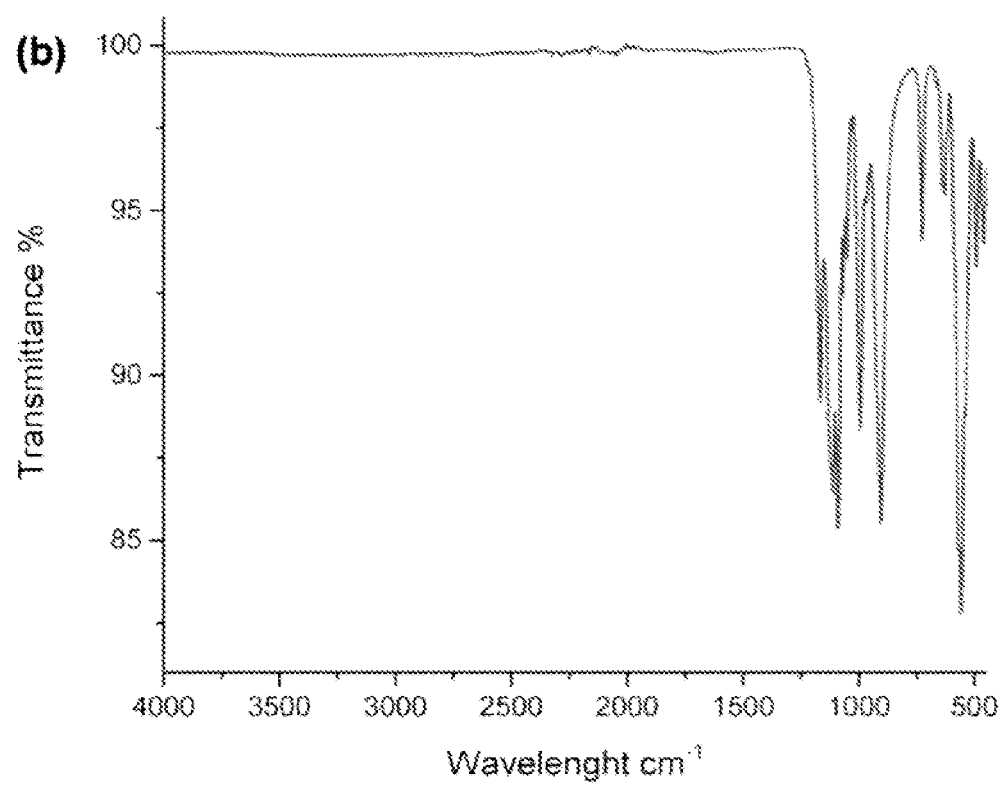
FIG. 30 shows the FT-IR spectrum of the same powder after calcination at 700° C. for 8 hours.

FIG. 30 shows the FT-IR spectrum of the same powder after calcination at 700° C. for 8 hours. As can be observed, the vibrations of the P—O—H moiety disappeared and new additional vibrational modes appeared in the frequency range of 1250-450 cm$^{-1}$ that were assigned to the presence of $P_2O_7^{4-}$, demonstrating the transformation of $HPO_4^{2-}$ to $P_2O_7^{4-}$.

Figure 31:
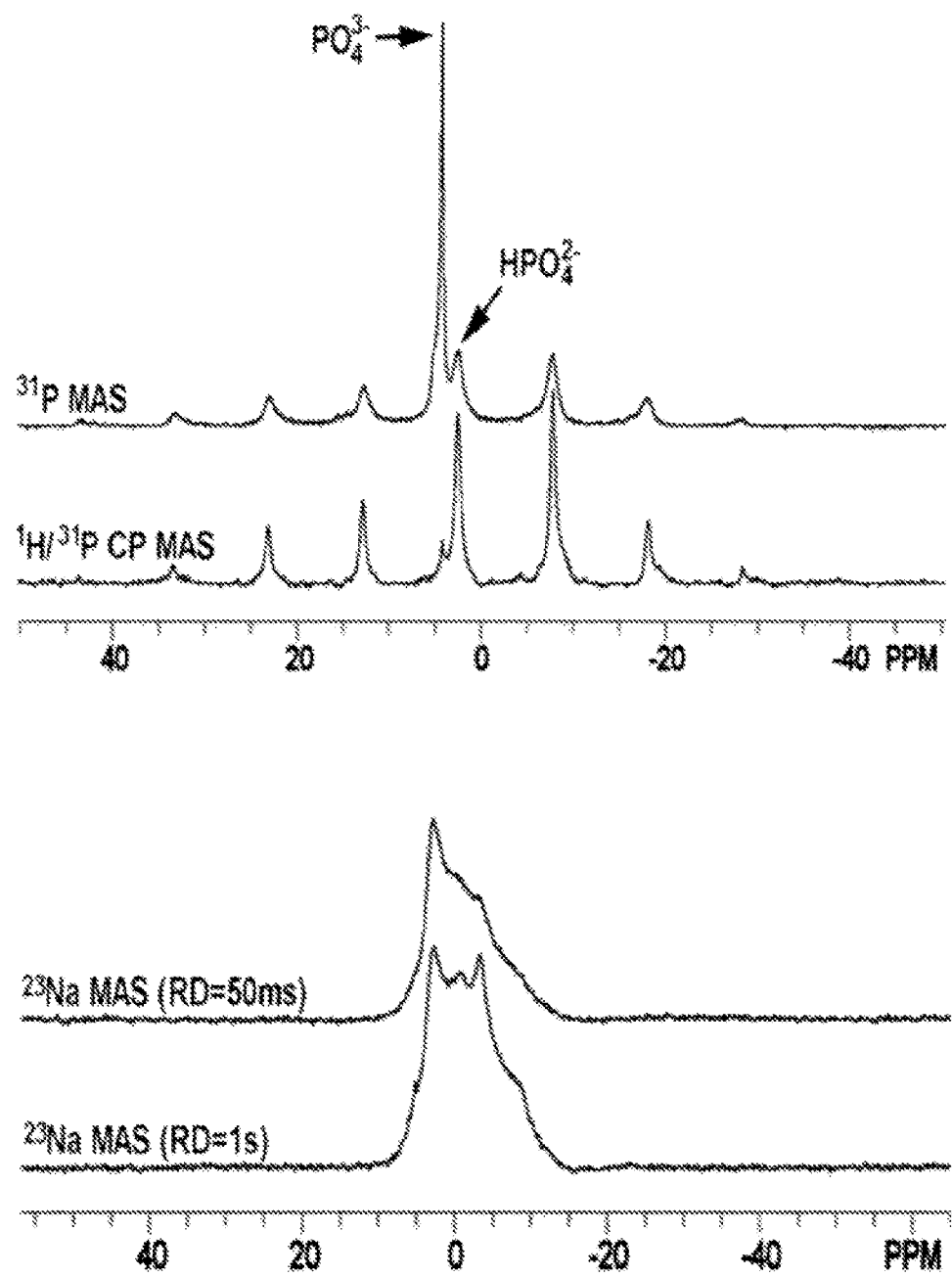
FIG. 31 shows the NMR spectra of formulation A, taken using a14T spectrometer.

The $^{31}P$ spectra (FIG. 31 top) revealed two peaks. The left one without visible sidebands was assigned as $P_4^{3-}$, whereas the right one with sidebands presented a stronger signal at the CP experiment and it was assigned as $HPO_4^{2-}$. $^{23}Na$ spectra taken with two different recycle delays (50 ms and 1 s) are shown in FIG. 31 bottom. One of the peaks was more evident at RD=50 ms. MAS NMR showed that, $HPO_4^{2-}$ cross polarizes intensely due to the small distance between hydrogen and phosphate ions in its chemical molecular structure. Therefore, $HPO_4^{2-}$ yields a stronger signal in the CP MAS spectra, as compared with $PO_4^{3-}$. On the other hand, $PO_4^{3-}$ yields a stronger and narrower signal in the regular $^{31}P$ MAS spectra with no detectable sidebands, indicating the isotropic nature of the crystals of this ion and the presence of a smaller spin-spin coupling effect.

Figure 32:
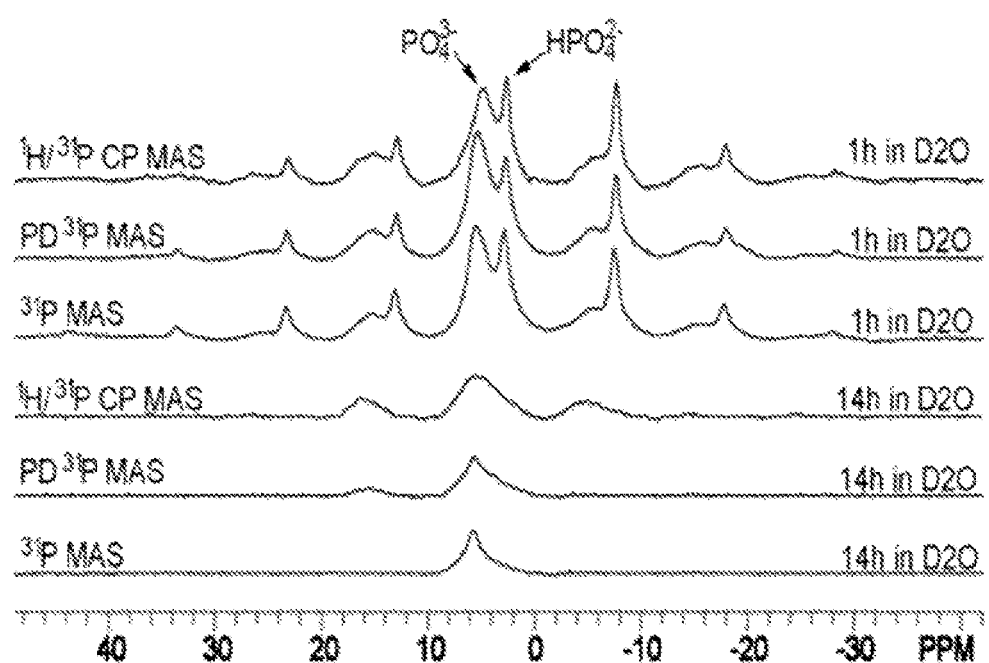
FIG. 32 shows the NMR spectra of the biomaterial of formulation A after immersion in $D_2O$.

After immersing the NMP gel in the $D_2O$ signal from $HPO_4^{2-}$ has been progressively weakened, with no remaining signal found in the experiment with 14 hours in $D_2O$, which indicates the protons exchange between this molecule and $D_2O$. On the other hand, all signals from $PO_4^{3-}$ have been broadened, and now presenting short and broad sidebands (more clearly noticeable in the CP experiments). This may have occurred due to the alteration of the chemical environment due to the presence of $D_2O$, causing different isotropic chemical shifts for $PO_4^{3-}$ and leading to a less organized crystallographic structure (FIG. 32).

Figure 33:
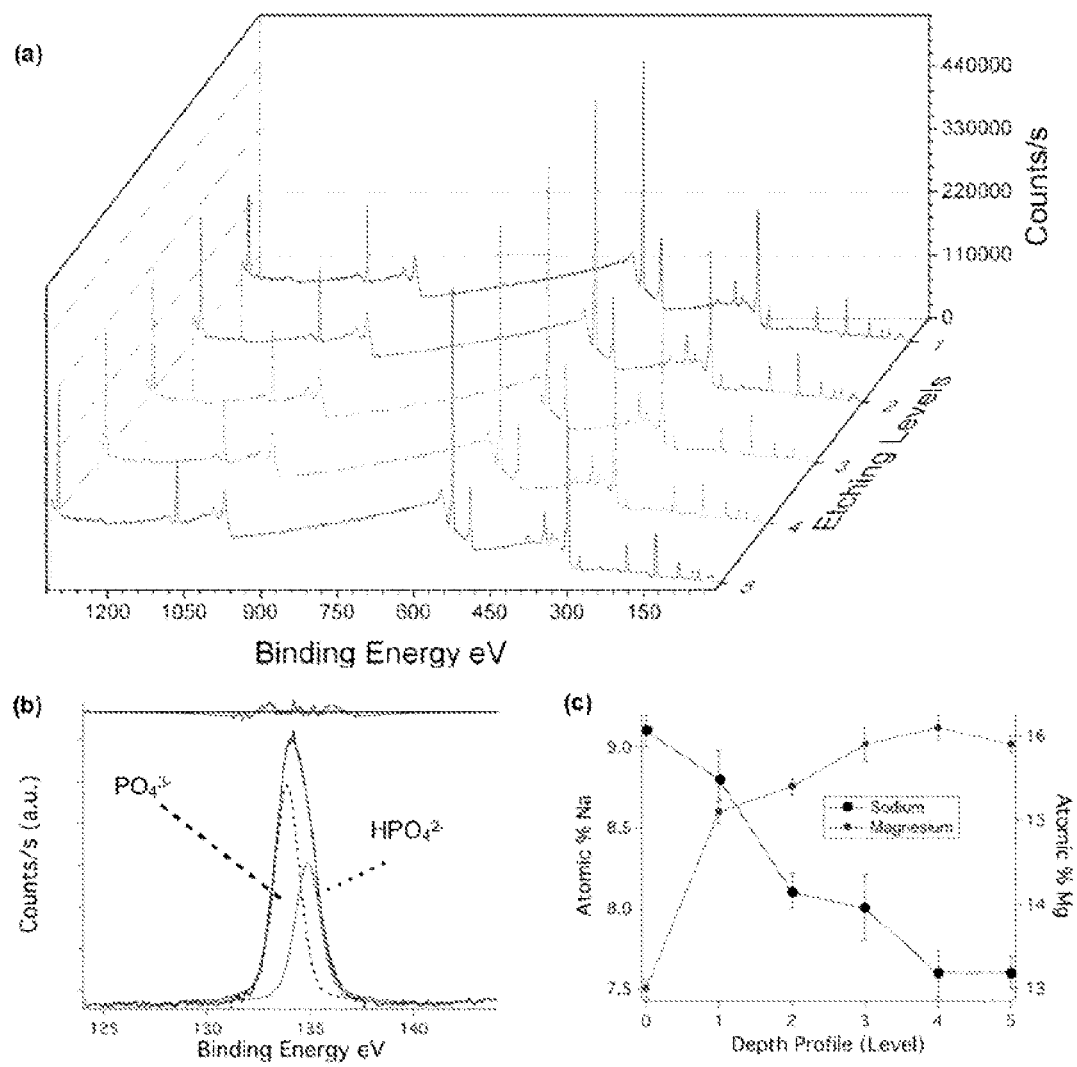
FIG. 33 shows a) XPS depth profile experiment of the NMP colloidal suspension synthesized on formulation A, b) the deconvolution of high resolution XPS spectra of P2p confirmed the presence of $PO_4^{3-}$ and $HPO_4^{2-}$, and c) the variation of the at. % of $Na^+$ and $Mg^{2+}$ of formulation A after mild etching using Ar ions.

High resolution XPS spectra P2p confirmed the presence of two different kinds of phosphate anions, and its deconvolution into two peaks at 133.7 and 134.9 eV were assigned respectively to $PO_4^{3-}$ and $HPO_4^{2-}$ (FIGS. 33 (a) and (b)).

XPS depth profile (FIG. 33 (c)) also revealed that the concentration of sodium slightly decreased from 9.1 to 7.6 at. % after mild etching using Ar ions at very mild condition. The superficial excess of sodium on the outer surface of the nanocrystals could be due to the presence of negative charges on the faces of the nanocrystals, and those ions might be responsible of the stabilization of the metastable nanocrystalline phase.

The deposition of NMP powder onto different treated glass surfaces was also studied. FIG. 34 shows the deposition of NMP on a negatively charged glass surface. The nanocrystals can adopt a parallel or perpendicular direction to the surface. FIG. 35 show NMP powder deposited on a positively charged glass surface. The nanocrystals adopt only a parallel configuration to the glass surface. In addition, the amount of nanocrystals deposited onto the substrate surface with negative charge was considerably higher than the positive surface. Note the contrast in FIGS. 34 and 35 was enhanced for visibility in black and white.

Cytocompatibility of NMP Colloidal Suspension

Figure 36:
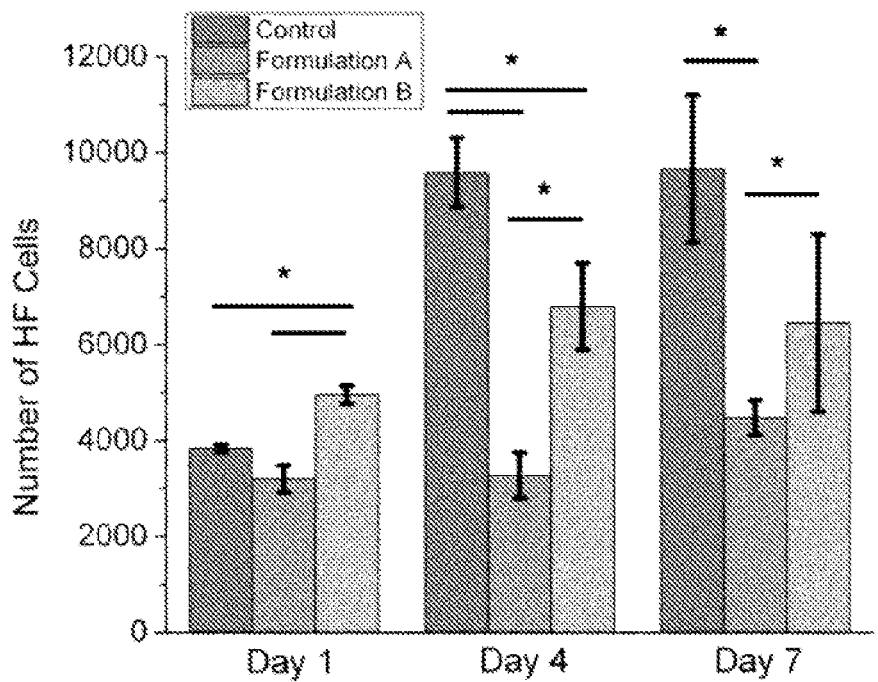
FIG. 36 shows the results of the metabolic activity using Alamar-Blue assay and live/dead assay on HF cells—number of HF cells.

We further investigated the cytotoxicity of the NMP nanocrystals by means of live-dead assay and Alamar-Blue assay to measure the metabolic activity. Alamar-Blue assay on Human Fibroblast cells seeded in direct contact with the NMP gel revealed that the metabolic activity of formulation A and B increased from day one to day seven (FIG. 36). Formulation B showed a higher metabolic activity than formulation A during the seven days of the experiment, and at day seven no significant difference was observed between the control and formulation B. The higher value of formulation B might arise from its more physiological pH (7.8) than formulation A (8.3) Live-dead assay results suggested good cell viability for the tested formulations A and B (FIG. 37 to 41).

Figure 37:
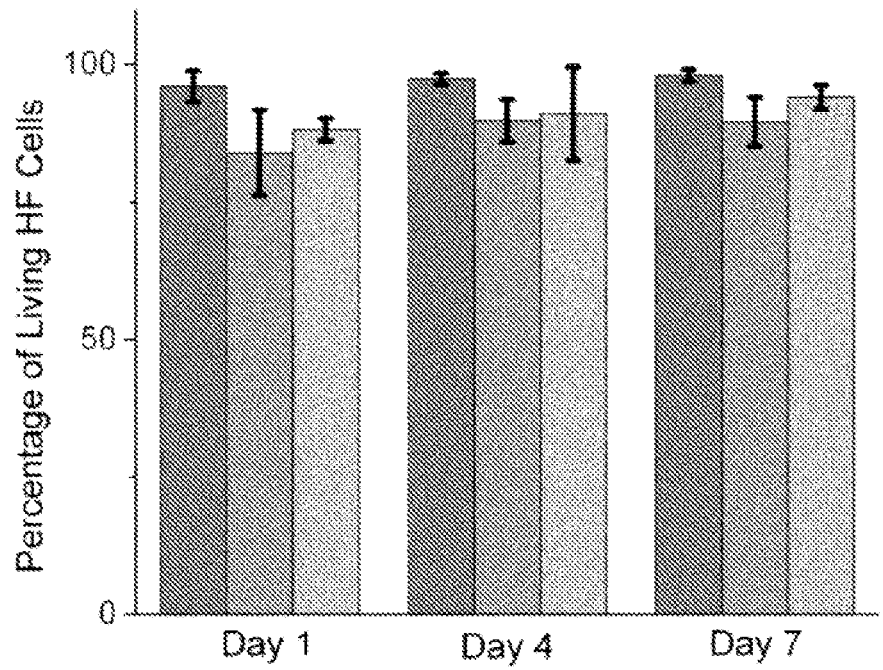
FIG. 37 shows the results of the metabolic activity using Alamar-Blue assay and live/dead assay on HF cells—percentage of Living HF cells.
Figure 38:
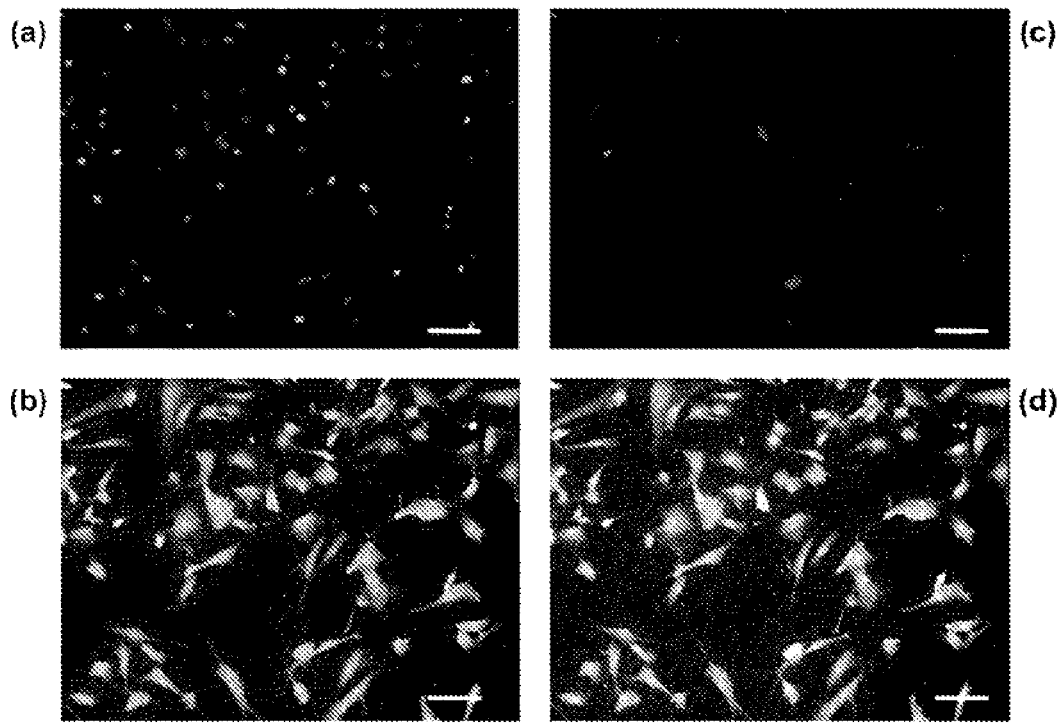
FIG. 38 shows the results of Live-Dead assay of formulation A at day 1. a-c, Channel splitting for the different dyes used (Calcein AM/Etd-1/Hoechst 33258); d, Micrograph after merging the three channels. The scale bar length is 100 μm.
Figure 39:
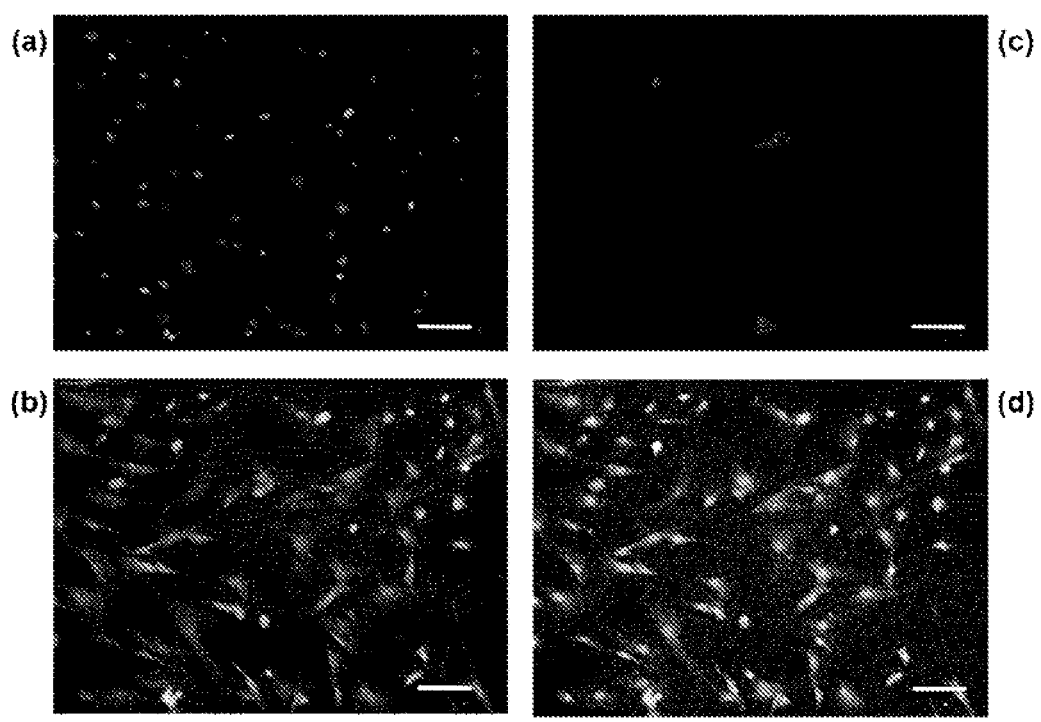
FIG. 39. shows the results of Live-Dead assay of formulation B at day 1. a-c, Channel splitting for the different dyes used (Calcein AM/Etd-1/Hoechst 33258). d, Micrograph after merging the three channels. The scale bar length is 100 m.
Figure 40:
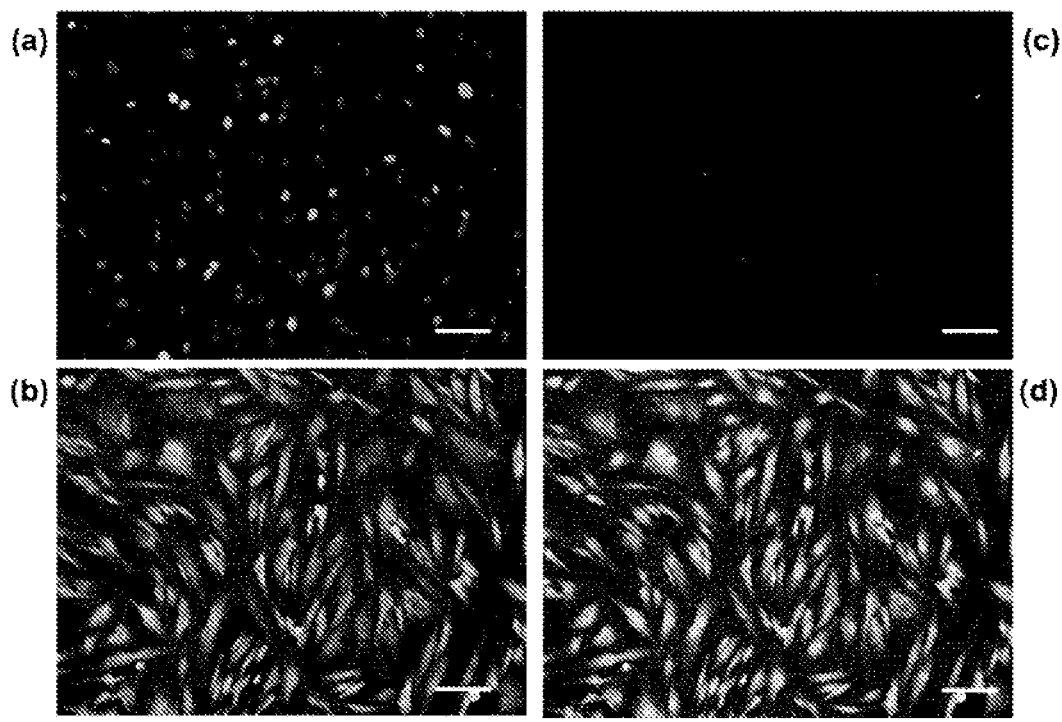
FIG. 40. shows the results of Live-Dead assay of formulation A at day 4. a-c, Channel splitting for the different dyes used (Calcein AM/Etd-1/Hoechst 33258). d, Micrograph after merging the three channels. The scale bar length is 50 m.
Figure 41:
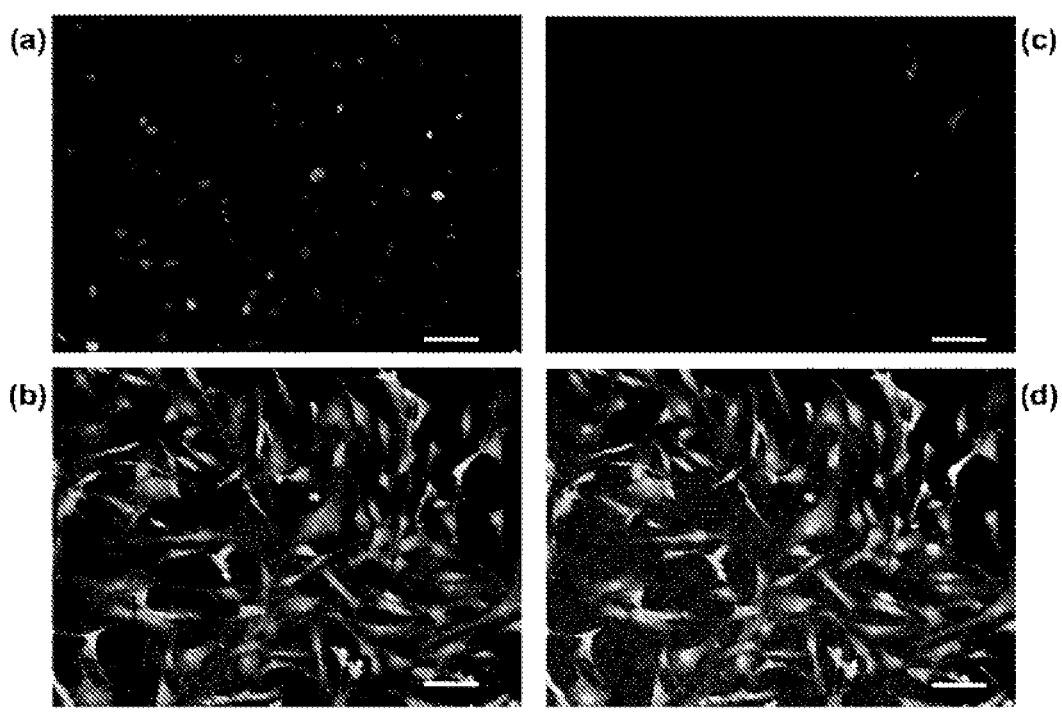
FIG. 41. shows the results of Live-Dead assay of formulation B at day 4. a-c, Channel splitting for the different dyes used (Calcein AM/Etd-1/Hoechst 33258). d, Micrograph after merging the three channels. The scale bar length is 50 m.

Note that the order of the bars in FIGS. 36 and 37 from left to right is the order shown in the legend in FIG. 36 from top to bottom. In FIGS. 38 to 41, contrast was enhanced for visibility in black and white.

Figure 42:
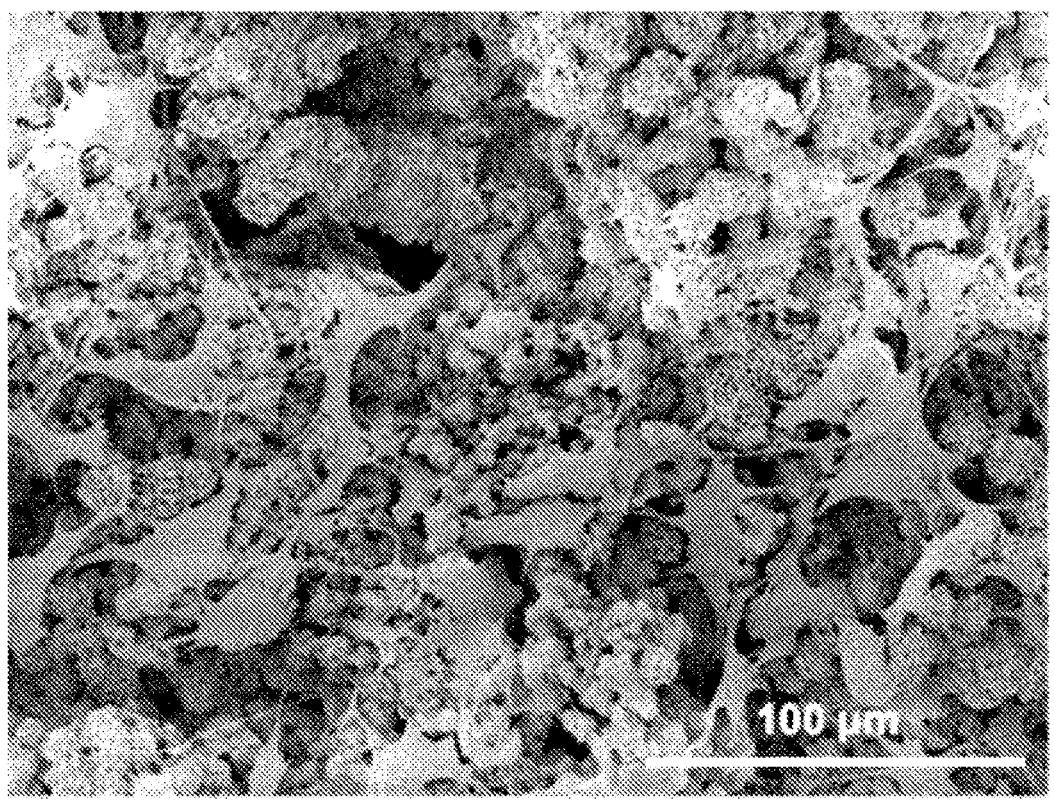
FIG. 42 is a SEM micrograph showing the adhesion and colonization of osteoblast cells onto NMP nanocrystals.

SEM micrograph shows the morphology, adhesion, and colonization of differentiated osteoblasts from mouse bone marrow cells (mBMCs) cultured onto NMP biomaterial. After eight days of culture, the image shows cell-cell and cell-substrate interactions that enabled the formation of a macro-scale tissue construct (FIG. 42). Moreover, comparing the structure of the NMP nanocrystals before and after cells culture, it can be observed an increase of the nanocrystals porosity probably due to the dissolution of the NMP nanocrystals.

Figure 43:
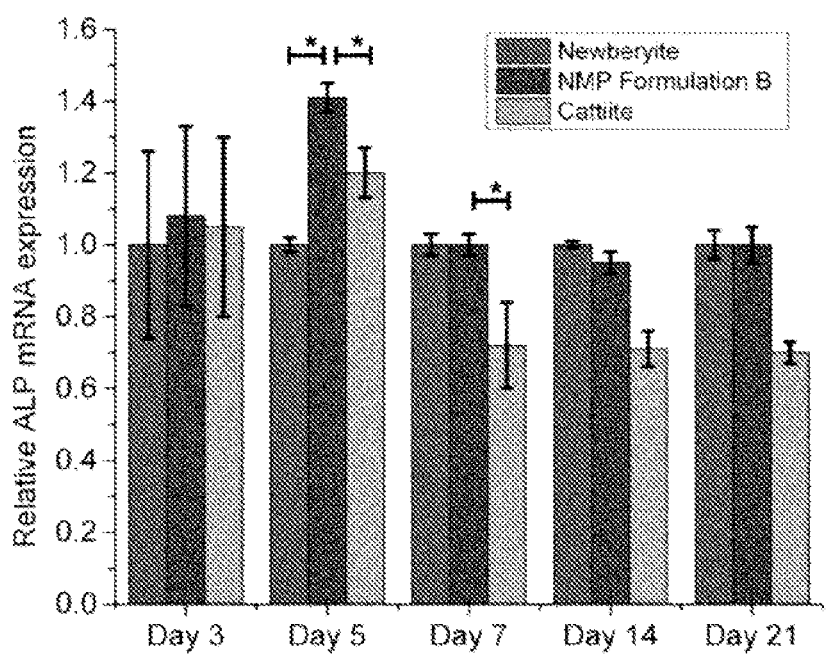
FIG. 43 shows the mRNA quantitative expression of ALP of mouse bone marrow cells grown for 21 days on, from left to right, Newberyite ($MgHPO_4.3H_2O$) (normalized values), NMP formulation B, and Cattiite ($Mg_3(PO_4)_2.22H_2O$)

The NMP gel synthesized in formulation B (pH 7.8) was further studied for bone formation purposes. Runt related transcription factor 2 (RunX2) is considered a key factor of osteogenesis due to the stimulation of osteoblast-related genes such as alkaline phosphatase (ALP), osteocalcin (OCN), osteopontin (OPN), and collagen, type I, alpha1 (COL1A1). The regulation activity of ALP is a key event that occurs during the early time of osteogenesis. Our result shows an early increase and up-regulation of ALP during the first five days respect $MgHPO_4.3H_2O$ and $Mg_3(PO_4)_2.22H_2O$ indicating that NMP had a positive effect on ALP expression and promoted osteogenic differentiation (FIG. 43).

Figure 44:
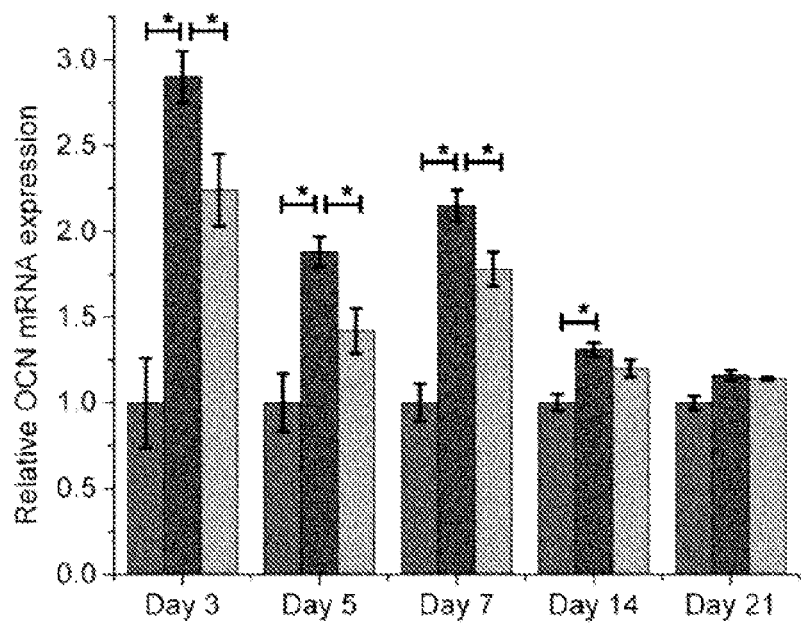
FIG. 44 shows the mRNA quantitative expression of OCN of mouse bone marrow cells grown for 21 days on, from left to right, Newberyite ($MgHPO_4.3H_2O$) (normalized values), NMP formulation B, and Cattiite ($Mg_3(PO_4)_2.22H_2O$)

The synthesis of OCN and OPN is also a key indicator for bone mineralization. OCN is secreted solely by osteoblasts and regulates body metabolism and bone building process, being the most specific marker for osteoblast differentiation and mineralization. Real Time-PCR of OCN showed that during the first 14 days, mBMCs cultured on NMP expressed significant higher levels of the gene than cells cultured on $MgHPO_4.3H_2O$ and $Mg_3(PO_4)_2.22H_2O$ (FIG. 44).

Figure 45:
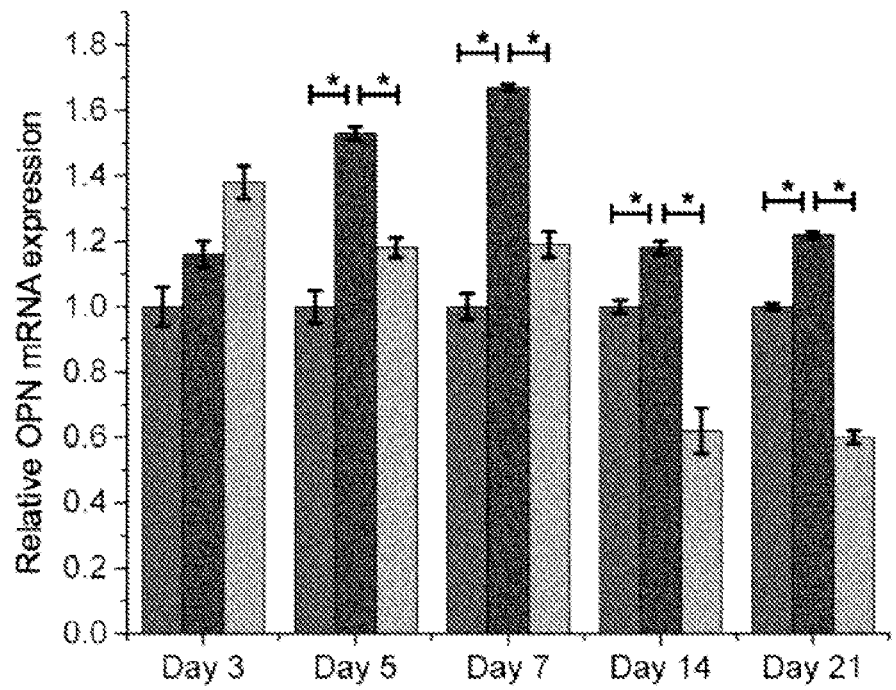
FIG. 45 shows the mRNA quantitative expression of OPN of mouse bone marrow cells grown for 21 days on, from left to right, Newberyite ($MgHPO_4.3H_2O$) (normalized values), NMP formulation B, and Cattiite ($Mg_3(PO_4)_2.22H_2O$)

OPN or bone sialoprotein is a structural protein that accounts ~8% of all non-collagenous proteins found in bone, and it is mainly synthesized by pre-osteoblasts, osteoblasts and osteocytes. Our results shown that NMP up-regulated the expression of OPN up to 21 days (FIG. 45).

We also followed the mRNA expression of COL1A1, a gene responsible to encode the production of pro-alpha1(I) chain of type I collagen that is a constituent of the ECM in connective tissue such as bone, skin, tendon, ligament and dentine. NMP up-regulated COL1A1 expressed by mBMCs reaching a maximum at day 7 in comparison to $MgHPO_4.3H_2O$ and $Mg_3(PO_4)_2.22H_2O$ (FIG. 46). mBMCs cultured on NMP expressed higher levels of RunX2 than mBMCs cultured on Cattiite ($Mg_3(PO_4)_2.22H_2O$) and Newberyite after five days of incubation (FIG. 47).

In FIGS. 43 to 47, differences were assessed by one-way analysis of variance and accepted as statistically significant at $p<0.05*$.

The novel NMP material has osteogenic properties and can trigger a series of events such as osteoblast cell proliferation, collagen synthesis, ECM maturation, and mineralization which follow the temporal pattern of osteogenic differentiation. The 2D material up-regulates the mRNA expression of RunX2/ALP and also the genes responsible of the formation of the extracellular matrix with bone-related protein OCN, OPN, and type I collagen.

NPM Accelerates Bone Healing and Implant Osseointegration

Figure 48:
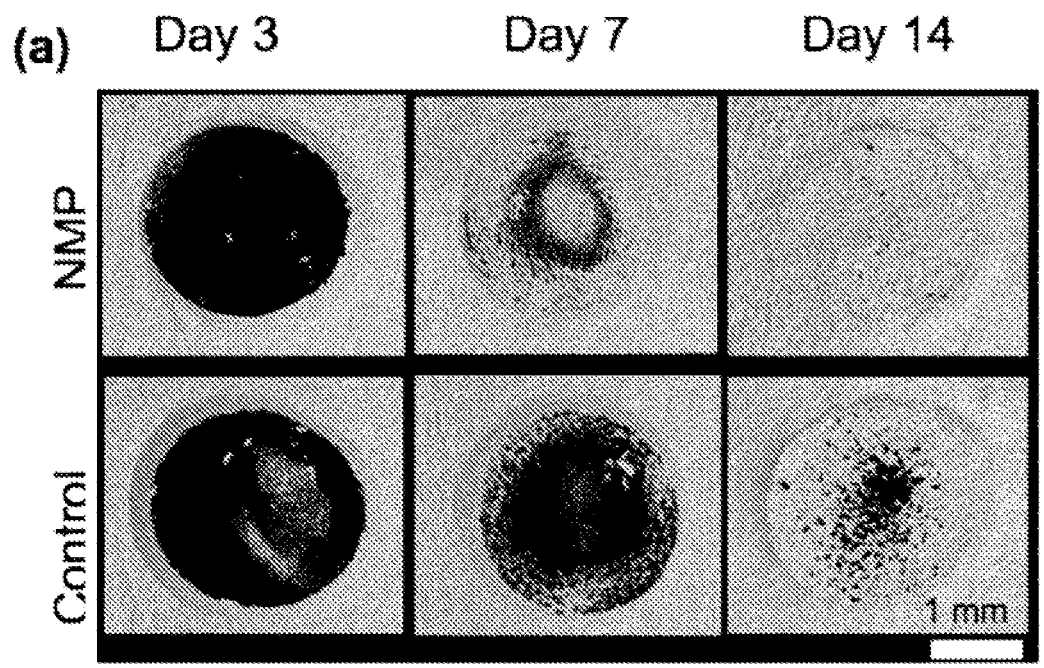
FIG. 48 shows μ-CT 3D models of the bone defects at day 3, 7 and 14.

NMP effects on bone formation (healing and osseointegration) were also investigated in vivo using rats' tibiae model. Computerized micro-tomography (μ-CT) scans were performed on bone samples that were retrieved at different time points 3, 7 and 14 days after surgery for NMP treated and non-treated defects. At day 3, there is no visible difference on μ-CT scan between the control and NMP group. On the other hand, at day 7 the μ-CT scan clearly indicates that the tibial defect treated with NMP shown more bone formation in the defect compared to the control ones (FIG. 48). After 14 days, the tibial defect treated with NMP is almost fully filled with new bone while the control is still partially healed.

Figure 49:
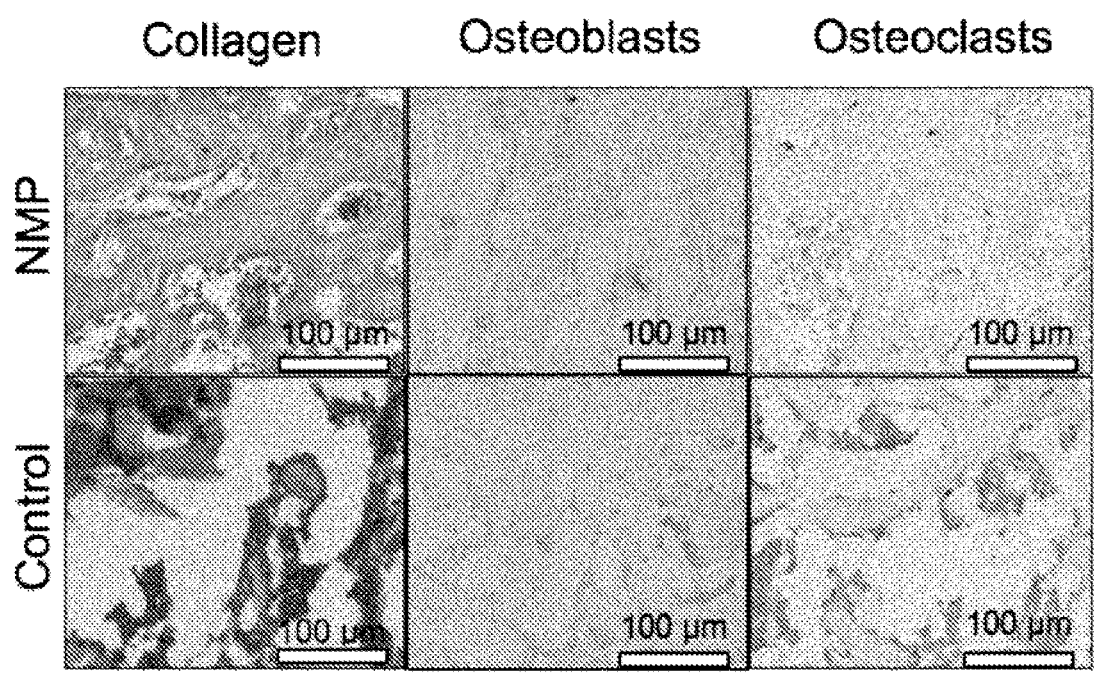
FIG. 49 shows histology and histomorphometry analysis (14 days after surgery): maison trichrome stain (collagen), ALP stain (osteoblasts) and TRAP stain (osteoclasts) in the control and the NMP-treated defects.
Figure 50:
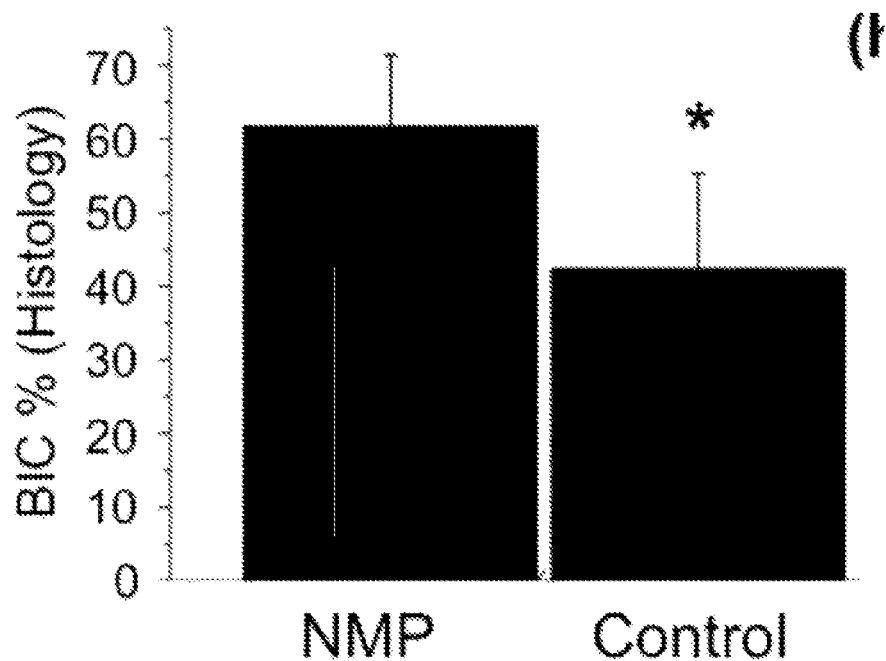
FIG. 50 shows the percentage of bone-implant-contact (BIC) in the control and the NMP-treated defects.
Figure 51:
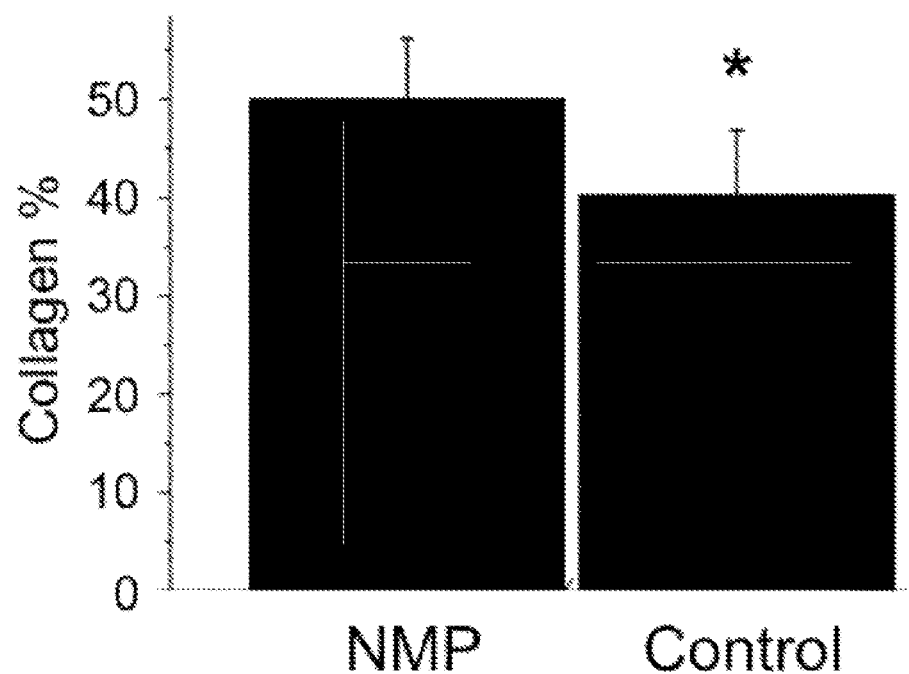
FIG. 51 shows the percentage of collagen in the control and the NMP-treated defects (Maison trichrome stain)
Figure 52:
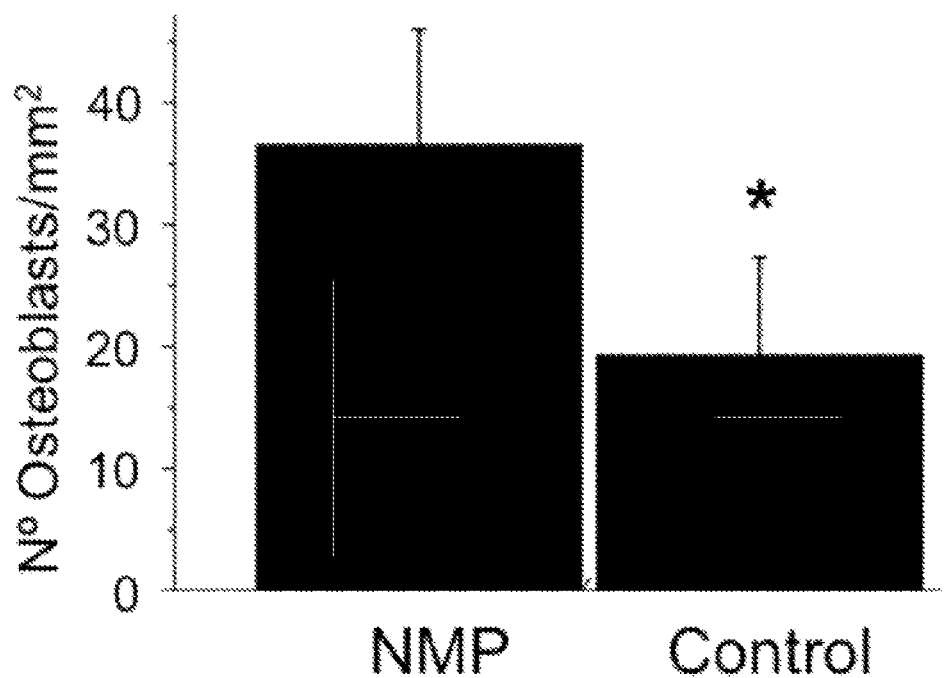
FIG. 52 shows the number of osteoblasts (ALP stain) in the control and the NMP-treated defects.
Figure 53:
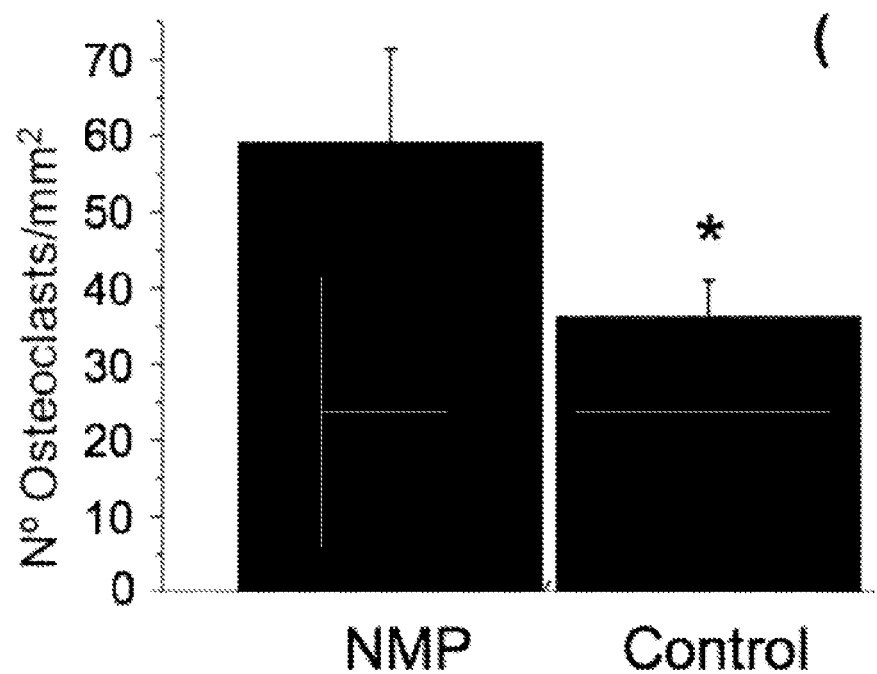
FIG. 53 shows the number of osteoclasts (TRAP stain) in the control and the NMP-treated defects.
Figure 54:
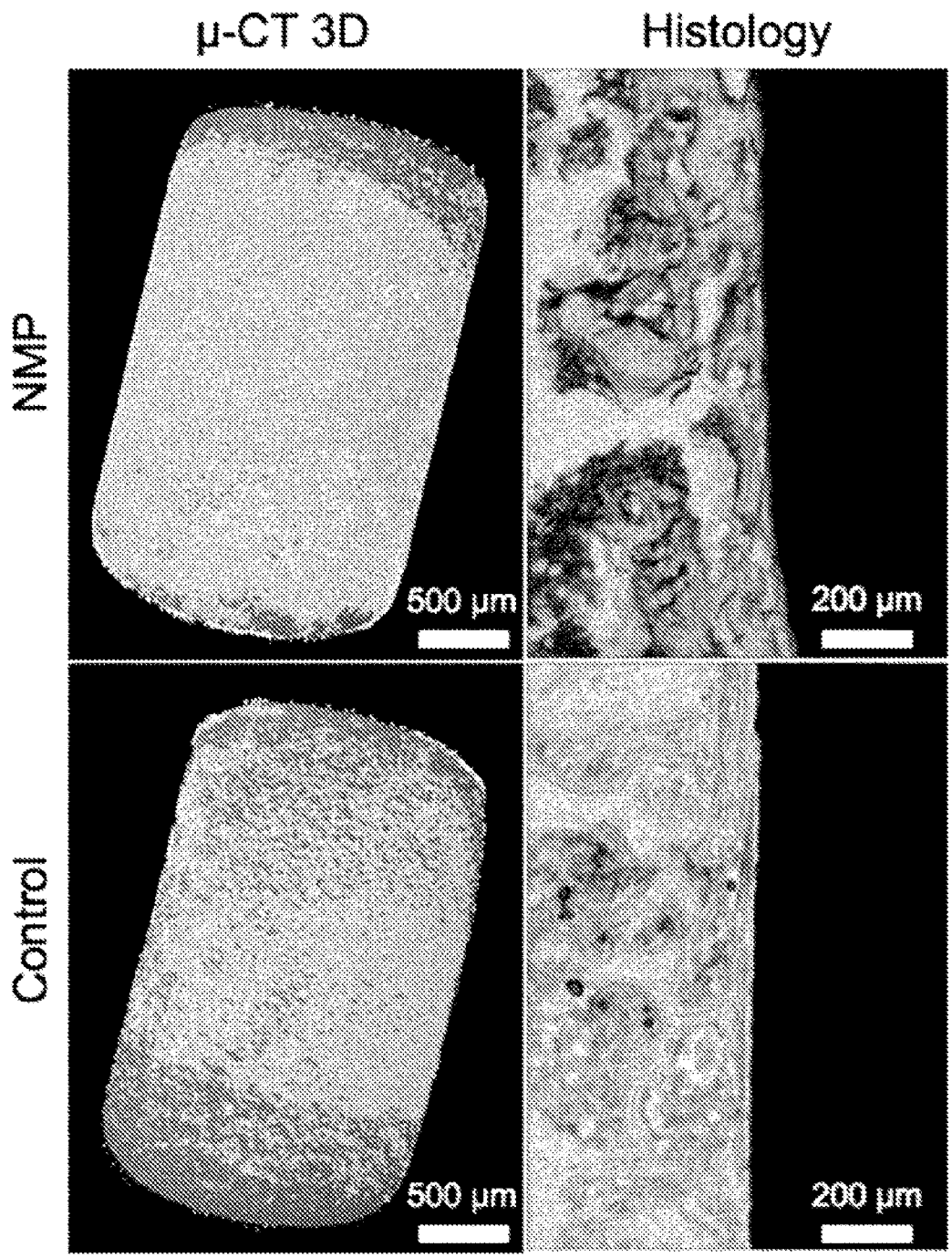
FIG. 54 shows μ-CT 3-D models and coronal histological sections of Ti-implants showing more bone (lighter in color in μ-CT and darker in histology) in contact with implant in NMP-coated implants.

Histology and histomorphometry analysis showed that NMP accelerated bone healing and enhanced osseointegration (FIGS. 49 to 53 and Table 4) through up-regulation of osteoclasts proliferation (FIGS. 49 and 53), osteoblasts differentiation (FIGS. 49 and 54), collagen synthesis (FIGS. 49 and 51) and mineralization (FIGS. 48 and 49). μ-CT and histology of implant show more bone in contact with implant (FIGS. 54 and 50). Histology and histomorphometry indicate that NMP clearly enhanced the bone forming cells; osteoblast and osteoclasts as well as collagen.

TABLE 4

μ-CT analyses show smaller defect volume, less trabecular separation (Tb.Sp), more trabecular thickness (Tb.Th) and trabecular number (Tb.N) in NMP-treated defects.

| Group | NMP | Control |
|---|---|---|
| Defect Vol. (mm³) | 1.51 ± 0.20 | 2.19 ± 0.32 |
| Tb.Th (mm) | 0.30 ± 0.04 | 0.25 ± 0.04 |
| Tb.Sp (mm) | 0.11 ± 0.02 | 0.15 ± 0.05 |
| Tb.N (mm⁻¹) | 2.52 ± 0.25 | 1.98 ± 0.61 |

Figure 55:
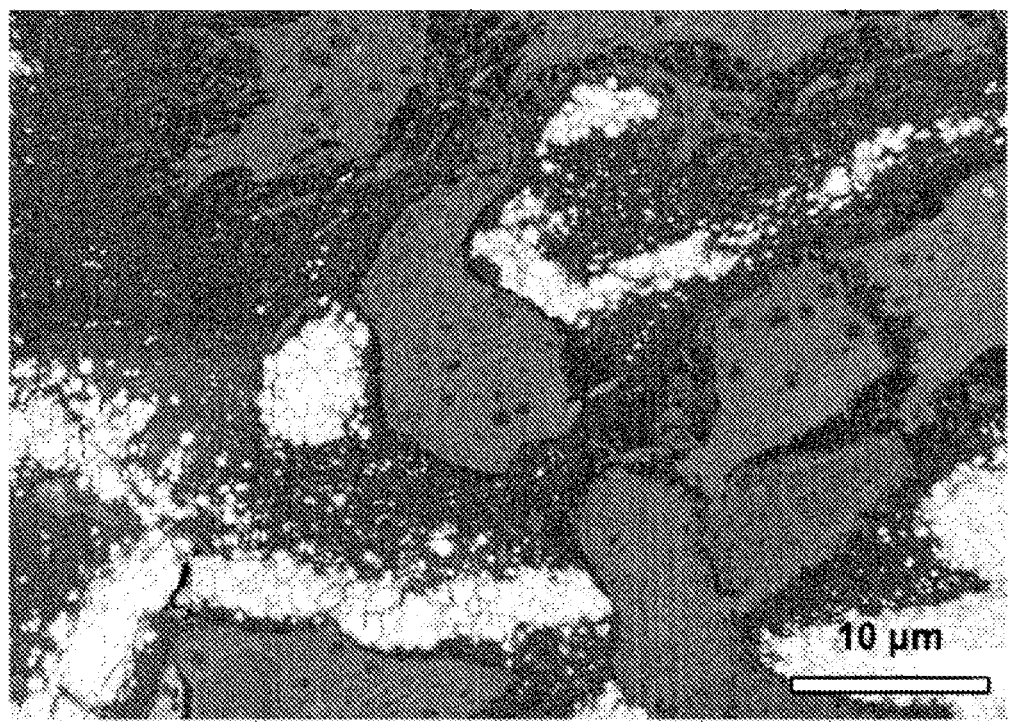
FIG. 55 is a FIB image showing bone matrix undergoing mineralization by osteoblasts in NMP-treated defect at day 7.
Figure 56:
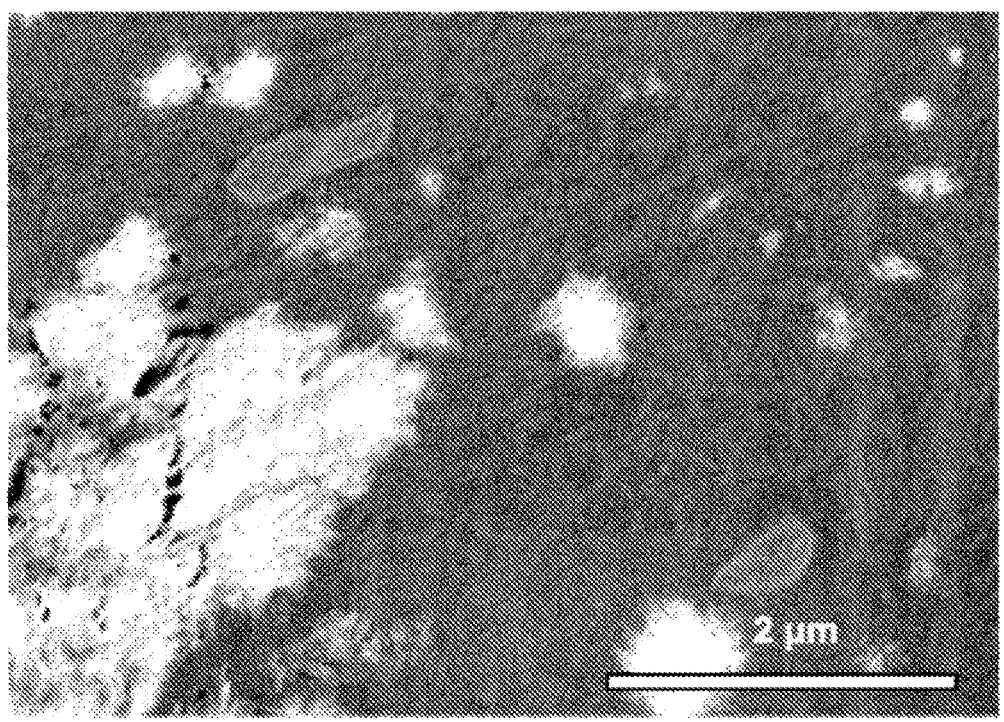
FIG. 56 is a FIB image showing collagen fibers undergoing mineralization in NMP-treated defect at day 7.

Focus Ion Beam SEM (FIB-SEM) was performed on defect samples that were retrieved at day 3 and 7. At day 3, no mineralization was present in both group, however at day 7, FIB-SEM images show collagen bone matrix undergoing mineralization by osteoblasts in NMP-treated defect (FIGS. 55 and 56).

Figure 57:
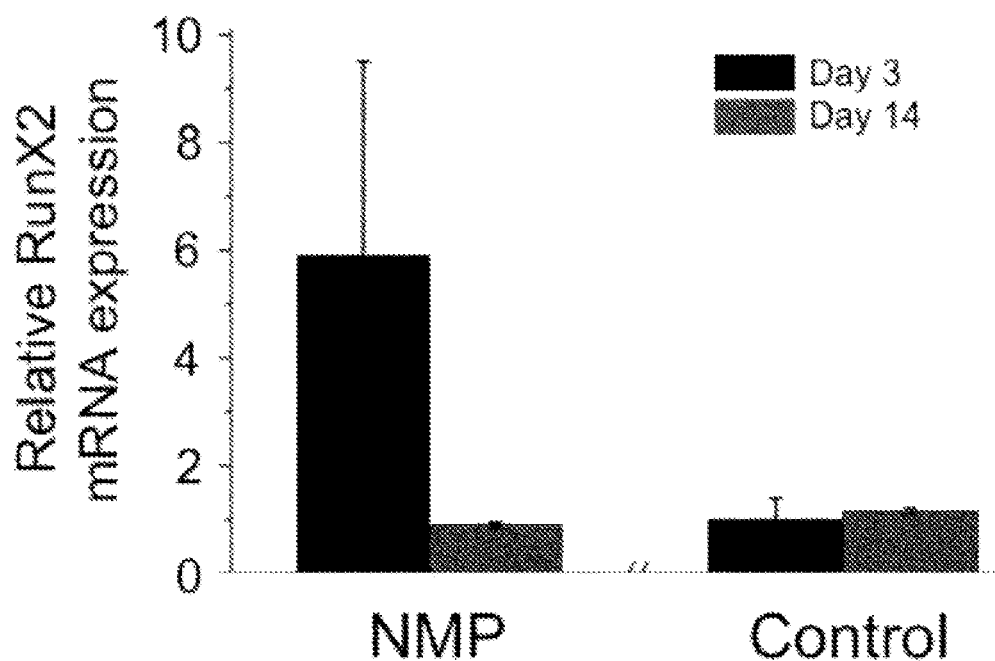
FIG. 57 shows the results of qRT-PCR showing that the expression of RunX2 was up-regulated in NMP treated, at day 3 (on the left) compared to the control, however, no significant difference was observed at day 14 (on the right)

NMP effects on genes expression (COL1A1 and RunX2) were further assessed in vivo by treating rats tibial defect with NMP. Bone samples were retrieved and assessed by qRT-PCR at different time points; 3, 7 and 14 days and showed that expression of COL1A1 and RunX2 were significantly up-regulated already at day 3 following surgery (FIGS. 57 and 58).

Osteoblast differentiation was up-regulated (FIG. 52) due to the NMP effects on osteoblastic gene markers ALP, OPN and RunX2 (FIGS. 43, 45, 47, and 57). The presence of magnesium ions increases the expression of osteoblast phenotype genes. Magnesium increases the expression of ALP, OPN and RunX2. On the other hand, calcium increases the expression of ColI.

Osteoclasts proliferation was also enhanced by NMP (FIGS. 49 and 53). NMP, which is rich of magnesium, enhanced osteoclasts proliferation and mineralization of the healing defects.

Figure 46:
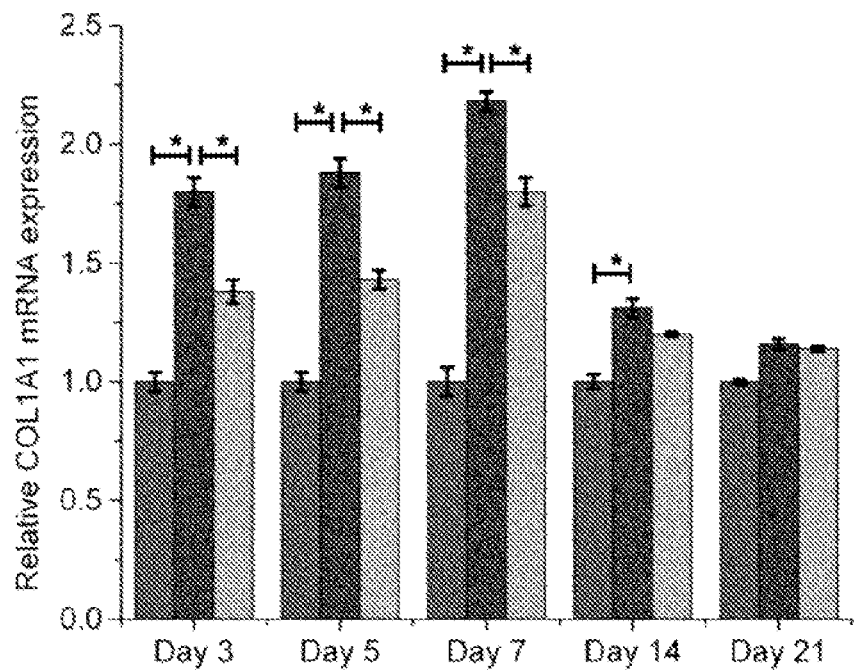
FIG. 46 shows the mRNA quantitative expression of COL1A1 of mouse bone marrow cells grown for 21 days on, from left to right, Newberyite ($MgHPO_4.3H_2O$) (normalized values), NMP formulation B, and Cattiite ($Mg_3(PO_4)_2.22H_2O$)
Figure 47:
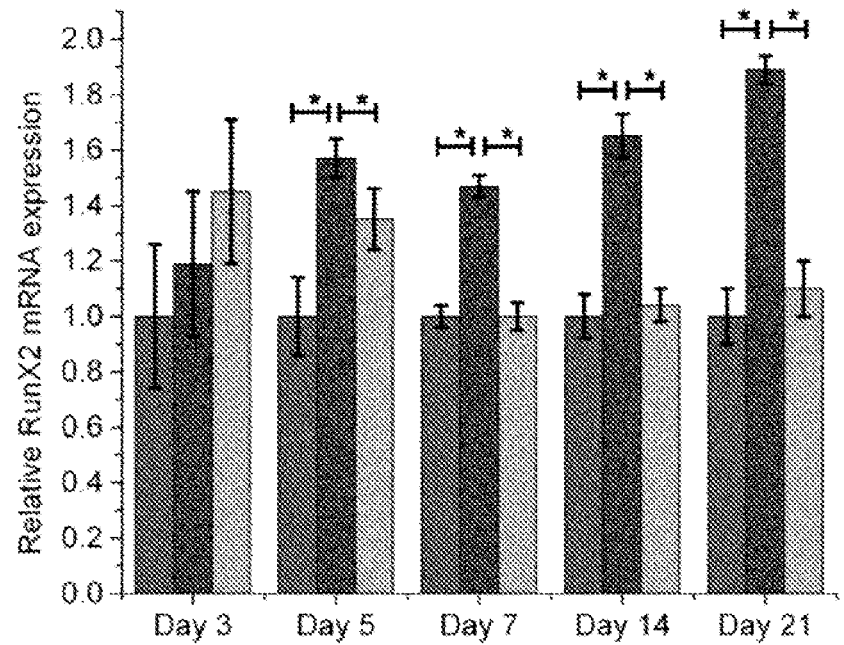
FIG. 47 shows the mRNA quantitative expression of RunX2 of mouse bone marrow cells grown for 21 days on, from left to right, Newberyite ($MgHPO_4.3H_2O$) (normalized values), NMP formulation B, and Cattiite ($Mg_3(PO_4)_2.22H_2O$)
Figure 58:
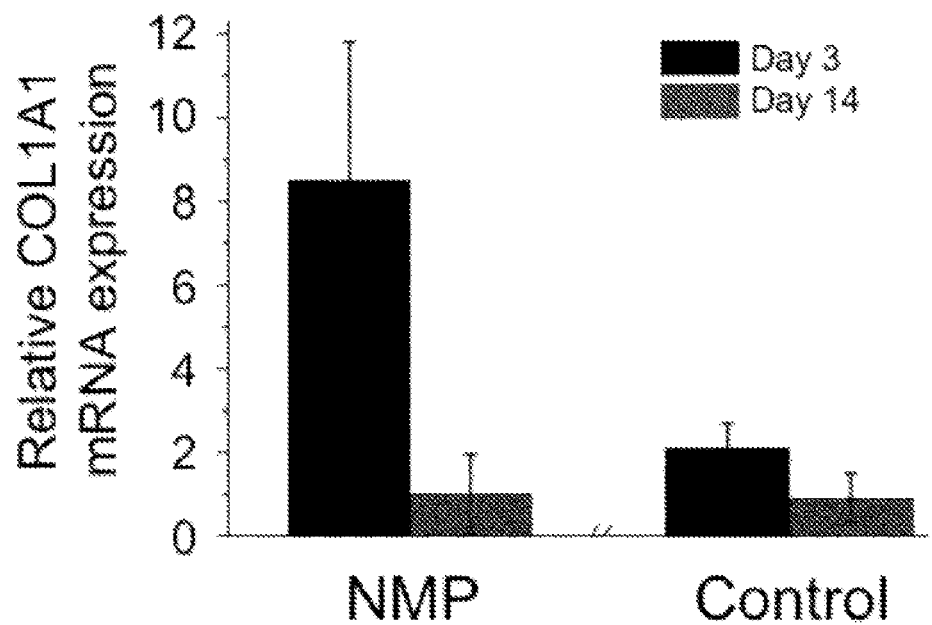
FIG. 58 shows the results of qRT-PCR showing that the expression of COL1A1 was up-regulated in NMP treated, at day 3 (on the left) compared to the control, however, no significant difference was observed at day 14 (on the right)

Collagen synthesis was also up-regulated in NMP treated defects (FIGS. 49 and 51) because NMP enhanced expression of COL1A1 (FIGS. 46 and 58).

Conclusions

In summary, we synthesized a nanocrystalline 2D biomaterial made of $Mg-Na-(HPO_4)-(PO_4)$. Water dispersions of NMP nanocrystals results in the constitution of a physical hydrogel that had thixotropic behavior and was easy to inject.

The physical properties of this novel material can be tailored by varying the mole fraction of $NaOH-Mg(OH)_2-H_3PO_4$.

Cell viability assays with human fibroblasts cells in direct contact with the NMP hydrogel showed its biocompatibility. In vitro mRNA expression of mBMCs cultured on NMP showed the up-regulation of genes (RunX2, ALP, OPN, OCN, and COL1A1). Moreover, it enhanced bone healing and osseointegration by stimulating differentiation and activity of bone cells; osteoblast, osteoclasts and collagen.

Example 2—Synthesis of Further Gels

Here, we describe the synthesis of nanocrystalline materials with platelet morphology. The 2D nanocrystals were characterized using a variety of analytical methods. The nanomaterials are based on a novel family of $M^IM^{II}(HPO_4)^{2-}(PO_4)^{3-}$ where $M^I=Na^+$ and $M^{II}=Mg^{2+}$ alone or combined with $Fe^{2+}$.

The synthesized nanocrystals formed colloidal suspensions that behaved as physical hydrogels presenting long term stability, thixotropy, injectability, and high surface area. Here, we further show an easy and scalable method to synthesize 2D nanomaterials obtained by a simple precipitation route. The easiness of synthesis and the interesting physicochemical properties of these materials open promising application in catalysis, layer by layer deposition, and electrodes for batteries.

Experimental Section

Materials and Methods

We synthesized different $M^IM^{II}(HPO_4)^{2-}(PO_4)^{3-}$ where $M^I=Na^+$ and $M^{II}=Mg^{2+}$ alone or combined with $Fe^{2+}$.

$FeCl_2 \cdot 4H_2O$ and $Mg(OH)_2$ were purchased from Sigma-Aldrich (Milwaukee, Wis., USA).

2D Nanocrystals of $MgNa(HPO_4)^{2-}(PO_4)^{3-}$

Stable colloidal suspension of 2D nanocrystals was done using the following conditions. 85 mg of $Mg(OH)_2$ (1.45 mmol, mole fraction 0.14) were dissolved in 2.2 mL of $H_3PO_4$ 1.5 M (3.30 mmol, mole fraction 0.31). After complete dissolution of $Mg(OH)_2$, 3.8 mL of NaOH 1.5 M (5.7 mmol, mole fraction 0.55) were added under vigorous stirring. The addition of NaOH provoked the instantaneous formation of a white colloidal suspension that after 6 minutes changed to a solid state with a grey color. The final pH of the colloidal suspension was 8.46. After 2 hours, the colloidal suspension was centrifuged at 4000 rpm for 5 minutes and the supernatant was discarded. The solid precipitate was washed with ethanol to remove the excess of water, vacuum dried at room temperature, and stored for characterization.

Combination of $FeCl_2 \cdot 4H_2O$ and $Mg(OH)_2$ 60 mg $FeCl_2 \cdot 4H_2O$ (0.3 mmol, mole fraction 0.02) and 90 mg of $Mg(OH)_2$ (1.54 mmol, mole fraction 0.12) were dissolved in 2.6 mL of $H_3PO_4$ 1.5 M (3.9 mmol, mole fraction 0.31) and to this solution were added 4.5 mL of NaOH 1.5 M (6.75 mmol, mole fraction 0.55) to yield a pale green colloidal suspension. The final pH was 8.10. The mixture was processed as described for Mg.

Synthesis of MgNa(HPO$_4$)$^{2-}$(PO$_4$)$^{3-}$ Colloidal Dispersion Using Different Sources of Mg The colloidal dispersion with Mg was also obtained by using magnesium chloride (MgCl$_2$.6H$_2$O) instead of magnesium hydroxide (Mg(OH)$_2$). The reaction was carried out by dissolving 667.5 mg of MgCl$_2$.6H$_2$O (3.275 mmol) in 2.5 mL of deionized water and 935 mg of Na$_2$HPO$_4$ (6.525 mmol) in 10 mL of deionized water. After dissolving the solids, the Na$_2$HPO$_4$ was poured into the solution of MgCl$_2$.6H$_2$O under stirring. The resulting colloidal dispersion had a white color and after 20 minutes from the beginning of the reaction a grey thixotropic gel was obtained.

NaMg(HPO$_4$)$^{2-}$(PO$_4$)$^{3-}$ was also obtained by replacing Mg(OH)$_2$ with magnesium oxide (MgO). Briefly, 160 mg of MgO were dissolved in 11.2 mL of H$_3$PO$_4$ 1.5 M and 16.8 mL of NaOH 1.5 M were added under vigorous stirring. The colloidal suspension had a white color and after 10 minutes a grey thixotropic gel was obtained.

The replacement of NaOH with sodium tripolyphosphate (Na$_5$P$_3$O$_{10}$) also allowed the production of the M$^I$M$^{II}$(HPO$_4$)$^{2-}$(PO$_4$)$^{3-}$ gel. Briefly, 110 mg of MgCl$_2$.6H$_2$O (0.545 mmol) were dissolved in 2.5 mL of deionized water and 12.5 mL solution of NaOH 0.2 M and Na$_5$P$_3$O$_{10}$ 15% were added under stirring.

Large Scale Mixtures

Most of the previously described colloidal suspension can be made in small volume batches of 50 mL. Using the conditions reported, we studied the scalability of the synthesis using a simple "2-in-" system with one tube connected to a reservoir of a NaOH solution (1.5 M) and the other tube connected to a reservoir of H$_3$PO$_4$ (1.5 M) solution containing Mg(OH)$_2$ (0.6 M). To obtain the NaMg(HPO$_4$)$^{2-}$(PO$_4$)$^{3-}$ colloidal suspension, the minimum flow velocity of the two solutions inside the tube to provoke a turbulent regime with a Reynolds number was >4000. Under these conditions, the turbulent flow at the intersection point provides a good mix of the two solutions and a method for the continuous production of the colloidal suspension.

Characterization

X-ray diffraction patterns of the dried precipitates were recorded with a Bruker D8 Advance (Bruker AXS GmbH, Karlsruhe, Germany) from 50 to 58° 2θ with a copper source ($\lambda_{Cu,Ka}$=1.54 Å) at 40 kV and 40 mA and GADDS detector. The diffraction patterns of the dried precipitates containing Fe were recorded with a Bruker D8 Discover from 50 to 58° 2θ with a cobalt source ($\lambda_{Cu,Ka}$=1.79 Å) at 35 kV and 45 mA and GADDS detector. The diffraction patterns were processed with EVA software (Bruker AXS GmbH, Karlsruhe, Germany) and phase composition was determined by comparing the acquired spectra with the phases identified in the International Centre for Diffraction Data (ICDD) database PDF-4.

Fourier Transform Infrared Spectroscopy (FT-IR) of the dried precipitates were recorded using a Perkin Elmer Spectrum Two (Perkin Elmer Inc, Waltham, Mass., USA) with single bounce diamond for Attenuated Total Reflectance (ATR). Spectra were recorded at room temperature from 450 to 4000 cm$^{-1}$ with a resolution of 4 cm$^{-1}$ and 64 scans.

Thermogravimetric analysis (TGA) was performed to calculate the amount of crystallization water of the dried precipitates (SDT Q600 TA Instruments, TA Instruments-Waters L.L.C. New Castle, USA). TGA was done in vertical mode on a platinum pan from 30 to 800° C. using a heating rate of 5° C./min, and in air atmosphere with a purge flow rate of 100 mL min$^{-1}$.

Zeta potential measurements were carried out to assess the superficial charge of the nanocrystals using a Malvern Nano ZS equipped with disposable folded capillary cells (Malvern Instruments Ltd, Malvern, UK). The nanocrystals concentration used for the measurements was set to 20 mg mL$^{-1}$ and the temperature was kept constant at 25° C.

The morphology of the different nanocrystals obtained was revealed by Scanning Electron Microscopy (SEM) using a FEI Inspect F-50 FE-SEM (FEI Inc, Hillsboro, Oreg., USA) operated at 10 kV. Prior analysis the samples were sputtered achieving a homogenous coating layer of 2 nm Pt (Leica EM ACE600, Leica Microsystems Inc, Concord, Ontario, Canada). The elemental composition of the colloidal suspension was determined using energy dispersive X-ray analysis spectroscopy (EDS) performed with an EDAX Octane Super Silicon Drift Detector and analyzed using TEAM™ software version 4.0.2 (AMETEK, Inc. Berwyn, Pa., USA). The device was installed on a F-50 FE-SEM (FEI Inc, Hillsboro, Oreg., USA) operated in secondary electron mode at 10 kV. ZAF (atomic number (Z), absorption (A), and fluorescence (F)) standard-less analysis was carried out on each of the EDS spectra using eZAF Smart Quant Results Acquisition (TEAM™ software version 4.0.2) to determine the atomic percentage (at. %) of the washed nanocrystals. The EDS spectra were acquired at 10 kV for ~2 min with a count rate of ~3000 counts/s.

The specific surface area of the products was measured by the Brunauer-Emmett-Teller (BET) method using nitrogen adsorption and desorption isotherms on an automated gas adsorption analyzer Tristar 3000 (Micromeritics Instrument Corporation Norcross, Ga., USA).

The force required to inject the thixotropic colloidal suspensions through an insulin needle of 160 μm of internal diameter was measured using a Mach-1 V500cs and Mach-1 Motion software version 4.3.1 (Biomomentum Inc., Laval, Canada). The force was measured with a multiple-axis load cell of 70 N (resolution of 0.007 N) and acquisition rate of 100 Hz. The gel was loaded into the syringe avoiding the presence of bubbles and then the plunger was inserted into the load cell. The force value was measured applying a constant vertical stage velocity of 1 mm s$^{-1}$ (resolution of 0.1 μm).

Results and Discussions

The colloidal suspensions formed physical gels.

The colloidal dispersions showed a thixotropic behavior forming a physical gel. The nanocrystals synthesized presented a two-dimensional morphology that to form a physical hydrogel with a thixotropic clay-like behavior. Clays are plate-like poly-ions with a heterogeneous charge distribution that forms a physical gel in water at concentrations higher than 40 mg/mL due to the simultaneous presence of positive and negative charges that give rise to electrostatic and Van der Waals interactions. This allows the gel to behave as a thixotropic material due to the formation of a 3D network of particles known as the "house of cards" structure. Thixotropic materials can be liquified by applying mechanical energy allowing the physical gel to behave as a liquid; then when the mechanical stress is removed Brownian motions drive the particles into contact to reform the 3D network and the liquefied dispersion becomes gel-like again. Like clays, the simultaneous presence of positive and negative charges allowed the novel synthesized nanocrystals dispersion to form a physical hydrogel with a "clay-like" behavior. As a result of its unique rheological property, the NMP gel could be injected easily through an insulin needle and after manual injection the colloidal suspension would regain solid-like behavior. After injection the material rapidly recovers its solid state and behaves again as solid, this is an important feature for coatings applications procedure.

The FT-IR data, X-ray diffraction pattern of the dried and washed powders demonstrated the nanocrystalline nature of the 2D nanocrystals due to the presence of broad diffraction peaks.

Example 3—from Toothpaste to "Implant-Paste": A New Product for Cleaning Dental Implants Abstract This study aimed at developing an organic-free prophylaxis paste optimized for cleaning dental implants (hereinafter called the "implant-paste"), while preserving their surface integrity.

The implant-paste was developed by combining an inorganic thickening agent made of a nanocrystalline colloidal suspension (Nanocrystalline Magnesium Phosphate) and polishing nanoparticles of hydrated colloidal silica. The implant-paste formulation was optimized to decontaminate titanium surfaces coated with oral biofilm and compared to a commercial toothpaste (Colgate Total; Colgate-Palmoliven, USA). Surface morphology, bacterial load and attachment and chemical properties of titanium surfaces were analyzed and comparisons between different products were done using one-way ANOVA and independent samples t tests.

Figure 59:
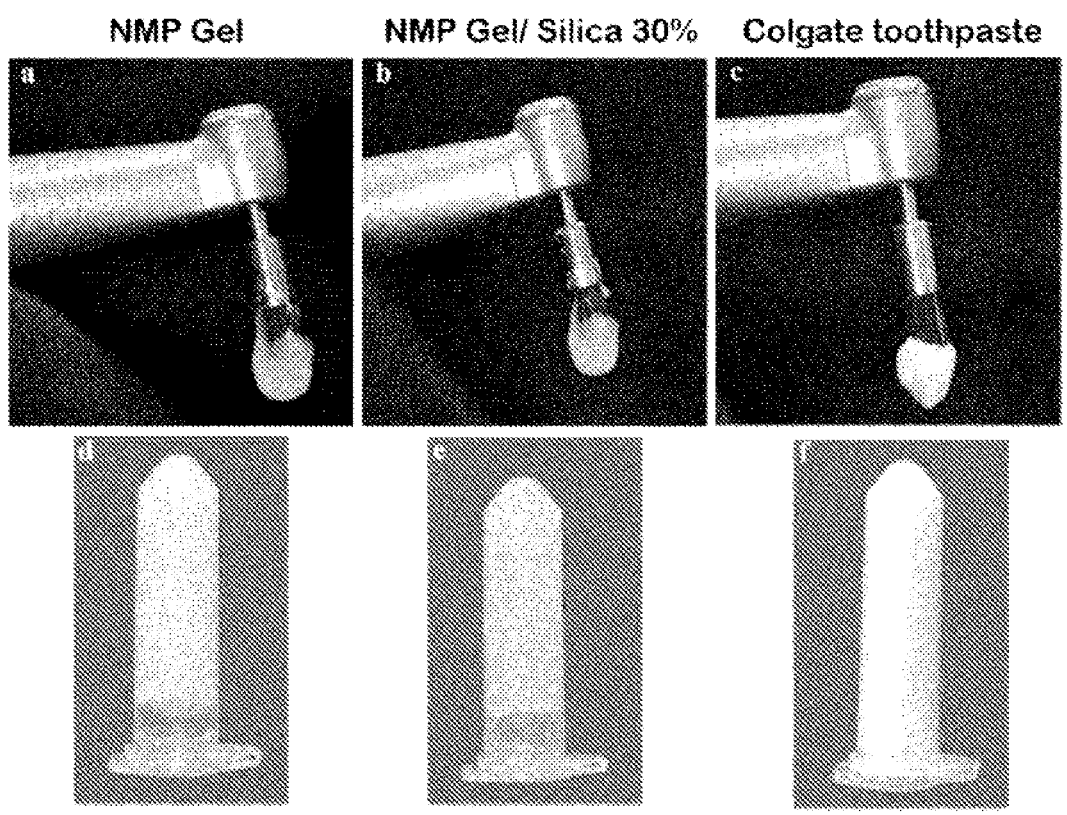
FIG. 59 shows A) (a-c) photographs of a rotary brush loaded with the NMP gel, the developed implant-paste and Colgate toothpaste and (d-f) photographs of the Eppendorf tubes containing the NMP gel, implant-paste and Colgate toothpaste respectively and B) a representative TEM micrograph of a freeze-fractured carbon-platinum replica of a 10% w/w NMP suspension showing the 3D structure and interactions of the nanocrystals composing the NMP gel.
Figure 59:
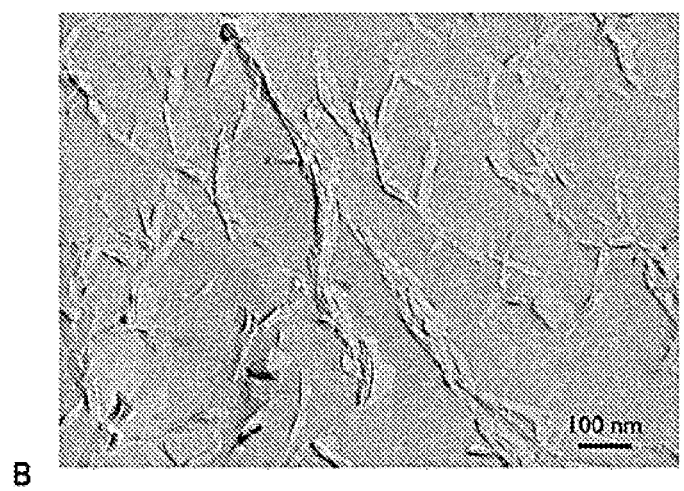

An inorganic prophylaxis paste made of nanocrystalline magnesium phosphate gel (10% w/w) and (30% w/w) hydrated silica was superior to brushing alone and Colgate toothpaste in removing titanium surfaces contaminants and it did not cause surface alteration. The thixotropic and inorganic nature of the nanocrystalline magnesium phosphate implant-paste is ideal for cleaning implant surfaces because, unlike the Colgate and other commercial toothpastes, it does not contain organic-based thickeners that can adhere tightly on titanium surfaces and thus change their surface chemistry and moreover, does not abrade titanium.
Introduction Nanocrystalline magnesium phosphate (NMP) gel is a novel inorganic colloidal suspension. It is stable biocompatible and thixotropic. NMP gel is silicate-free unlike other thixotropic inorganic materials such as silicate clays that could be more abrasive on implant surfaces. This novel gel is also rich in $Na^+$ cations that have toxic effect on bacteria and can disturb the biofilm structure by displacing the divalent cations ($Ca^{++}$). Conventional toothpastes comprise fluoride that can corrode Ti, organic compounds that can alter its surface chemistry and abrasives that can damage its surface microtexture. Accordingly, we hypothesized that prophylaxis pastes free of fluoride and organic compounds would be more efficient for cleaning dental implants. Thus, this study aimed at developing and optimizing a new "implant-paste" specifically designed for decontamination of dental implant.
Materials and Methods The study design was reviewed and approved by the Research Ethics Board Committee of McGill University (application 14-464 GEN). All subjects participating in this study have signed informed written consents before their participation.
Materials Synthesis The implant-paste was developed by combining a thickening agent made of an inorganic nanocrystalline magnesium phosphate (NMP) gel with different concentration of an abrasive agent of hydrated silica nanoparticles. In a typical procedure to synthesize the NMP gel, 300 mg of $Mg(OH)_2$ (5.14 mmol; Mole fraction=0.144 were dissolved in 8.1 mL of $H_3PO_4$ 1.5 M (12.15 mmol; Mole fraction=0.34), followed by the addition of 12.3 mL NaOH solution 1.5 M (18.45 mmol; Mole fraction 0.516). In another typical procedure, 270 mg of $Mg(OH)_2$ (4.62 mmol; Mole fraction=0.13) was dissolved in 7.5 mL of $H_3PO_4$ 1.5 M (11.25 mmol; Mole fraction=0.31), followed by the addition of 13.5 mL NaOH solution 1.5 M (20.25 mmol; Mole fraction=0.56). The addition of the NaOH solution provoked the instantaneous formation of a white liquid suspension made of nanocrystals with a uniform size of 50 nm. The pH of the suspension remained constant for 4 minutes (8.3) then slowly decreased and stabilized at 7.8 after 30 minutes for the first procedure, while it remained constant for 4 minutes at 10.1 then slowly decreased and stabilized at 9.6 after 30 minutes for the second procedure. The liquid suspension changed its color from white to grey and possessed a solid and thixotropic behavior with the final suspension composed of 2D nanocrystals with an undulate structure. The solid content of the paste was then modified by adding 20, 30, 50, or 60% of hydrated silica nanoparticles with average aggregate particles size of 0.2-0.3 µm. The addition of hydrated silica nanoparticles increased the viscosity of the gel depending on the concentration used, however, the thixotropic behavior and pH of the initial gel were not affected (see FIG. 59A).

Indeed, the photographs of a rotary brush loaded with the NMP gel, the developed implant-paste and Colgate toothpaste (a-c, respectively) and the photographs of Eppendorf tubes containing the NMP gel, implant-paste and Colgate toothpaste (d-f, respectively) clearly illustrate that the gel and developed implant-paste are more thixotropic than Colgate toothpaste. The Colgate toothpaste flew without applying mechanical shear while the other pastes did not flow.
Samples Preparation Machined and polished titanium discs (grade 2, Ø 5.0 and 1.0 mm thick; McMaster-Carr, Cleveland, Ohio, United states) were used in this study. The discs were sequentially ultrasonicated in deionized water, acetone and ethanol for 15 minutes each, before drying over-night in a vacuum oven (Isotemp, Fisher Scientific, USA).
Biofilm Contamination The biofilm was developed on the titanium surfaces following a previously described standard protocol—see Gosau, M., et al., Effect of six different peri-implantitis disinfection methods on in vivo human oral biofilm. Clinical Oral Implants Research, 2010. 21(8): p. 866-872; Idlibi, A N., et al., Destruction of oral biofilms formed in situ on machined titanium (Ti) surfaces by cold atmospheric plasma. Biofouling, 2013. 29(4): p. 369-379; Rupf, S., et al., Removing biofilms from microstructured titanium ex vivo: a novel approach using atmospheric plasma technology. PloS one, 2011. 6(10): p. e25893; and Größner-Schreiber, B., et al., Modified implant surfaces show different biofilm compositions under in vivo conditions. Clinical oral implants research, 2009. 20(8): p. 817-826, all of which are incorporated herein by reference.

Alginate impressions were taken to produce study models for each participant's upper jaw. A 1-mm-thick thermoplastic copolyester splints covering all maxillary teeth were produced. The splints were used to fix Ti discs at the buccal aspect of the premolar and molar areas, each splint housed 12 Ti discs. The participants were asked to wear the splints for 24 hours in order to allow for soft biofilm to accumulate on Ti surfaces. The participants were instructed to remove and store the splints during drinking or eating in phosphate buffered saline. After 24 hours, the splints were collected, the discs were washed with sterile saline solution (9%) and stored for further analysis.

Samples Cleaning

A rotary brush was used to clean biofilm-contaminated samples with water-intensive cooling at a speed of ~2500 rpm. The brush was held perpendicularly in gentle contact with the surfaces of the contaminated samples while moving in a circular motion.

The samples were initially brushed without paste for 1, 2 and 5 minutes in order to optimize the brushing time to that causing as little damage as possible to the surfaces (n=6 for each group). The implant-paste formulations; a gel containing 10% (w/w) NMP and 20, 30, 50, or 60% (w/w) of hydrated silica in water were then assessed with the optimized brushing parameters (n=3 for each group). After that, the samples were brushed with the optimized implant-paste and compared to surfaces cleaned with rotary brushes alone and others brushed with a commercial toothpaste (Colgate Total; Colgate-Palmoliven, New York, United states; n=6 for each group).

Analysis Methods

Ti surfaces were analyzed before and after the biofilm contamination and subsequent brushing using the following methods:

X-Ray Photoelectron Spectroscopy (XPS)

XPS is the most widely used surface analysis technique that measures the elemental composition, chemical state and electronic state of the elements within a material. The chemical composition of Ti surfaces was analyzed using X-ray Photoelectron Spectrometer (Thermo Fischer Scientific Inc, East Grinstead, UK). The in was equipped with a monochromatic Al Ka X-Ray radiation source (1486.6 eV, ($\lambda$) 0.834 nm) and an ultrahigh vacuum chamber ($10^{-9}$ torr). For all discs, survey scans were acquired over the range of 0-1350 eV with a pass energy of 200 eV and a resolution of 1.0 eV. A flood gun was used to neutralize the surface charging in all samples. Binding energies, peak areas and atom concentration ratios were obtained using the curve fitting function of Avantage (5.932v) analysis software (Thermo Fisher Scientific, Waltham, Mass. USA).

Live/Dead Bacterial Assays and Fluorescence Microscopy (FM)

Live/dead staining kit (BacLight Bacterial Viability Kit L7012, Molecular Probes, Carlsbad, USA) and fluorescence microscopy were used to evaluate the viability and attachment of bacteria on the contaminated and cleaned Ti discs (n=6 for each group). The live/dead stain was prepared by diluting 1 L of SYTO 9 (excitation ($\lambda$)=485 nm, emission=498 nm) and 1 µL of propidium iodide (excitation=535 nm, emission=617 nm) in 1 mL of distilled water. Discs were placed in 48-well plate, and 500 µL of the reagent mixture was added to each well followed by incubation at room temperature and in the dark for 15 min.

Each disc was then carefully placed on a glass slide, covered with mounting oil and stored in a dark space at 4° C. until further processing. Discs were evaluated using an upright fluorescence microscope (Carl Zeiss Microscopy GmbH, Gottingen, Germany) equipped with a digital camera (AxioCam MRm Rev. 3, Carl Zeiss Microscopy, Gottingen, Germany) and operated with an image processing software (ZEN; Carl Zeiss Microscopy GmbH, Gottingen, Germany). For each disc, five randomly-selected sites were captured; one from the centre and the other four from the quarters of the Ti surface using a 20× objective. Means of red fluorescent areas (dead cells), green fluorescent areas (viable cells), and total fluorescence (total bacteria) per standard microscopic field area (448×335=0.15 $mm^2$) were calculated (expressed as A.U.) using Cell Profiler image analysis software (Broad Institute of MIT and Harvard, Massachusettes, USA).

Scanning Electron Microscope (SEM)

Ti surfaces were scanned before and after biofilm contamination, and after each cleaning procedure to visualize the surface contaminants or any topographical changes. Clean Ti discs were scanned with SEM (FE-SEM S-4700, Hitachi, Japan) without further preparation while the contaminated discs were prepared as follows: the discs were fixed in glutaraldehyde (2.5% in phosphate buffered saline (PBS); PAA Laboratories GmbH, Pasching, Austria) for 2 hours and washed 5 times for 10 minutes in PBS, before dehydrating them in ascending concentrations of ethanol (30-100 v/v %, 15 min each). The discs were then dried using critical point $CO_2$ (Ladd Research Critical Point Dryer). All discs were mounted on SEM-sample stubs and sputtered with gold. The SE mode with an acceleration voltage of 20 kV was selected, and the vacuum pressure was maintained below $1\times10^{-5}$ torr. For direct comparison of surface topography, the same magnification of ×10,000 was selected for all samples.

Confocal Laser Scanning Microscope

A LEXT 3D Confocal Microscope (Olympus America Inc., PA) was used to evaluate the surface roughness of polished Ti discs before and after decontamination. The surface roughness was characterized with roughness profile parameters [average roughness (Ra) and root mean square roughness (Rq)]; a method extensively used for assessing the surface roughness of implants. All values were determined at a cut-off length of 0.08 mm in 50 sections (evaluation length of 4 mm), and evaluated using the LEXT OLS4000 software (Olympus, America Inc., PA). Four discs were used for each group, and measurements were taken at five random areas from each disc.

Statistical Analysis

The primary outcome variables were surface chemical composition, surface roughness, and bacterial attachment and viability. For each cleaning technique, data of the primary variables was statistically analyzed based on paired design for comparison of the measurements from before and after contamination and decontamination. The outcomes of different decontamination methods were also analyzed and compared.

Repeated measures ANOVA and Paired-sample t-tests were used to compare the outcomes of the same groups at different treatment time points while one-way ANOVA and independent samples t-tests were performed to compare the outcomes of different groups and techniques. The data analyses were carried out using SPSS software version 22 (SPSS Inc., IBM Corporation, Somers, N.Y., USA) and Origin 9.0 (Origin lab, Northampton, Mass., USA). A p-value of <0.05 was set to represent a statistically significant difference between groups.

Results

Surface Chemistry of Clean and Biofilm-Contaminated Surfaces

The XPS survey spectra of clean surfaces showed the presence of the following major peaks: O1s (Oxygen), C1s (Carbon), Ti2p (Titanium) and N1s (Nitrogen) (see FIGS. 60A and B). C1s and N1s signals indicate the surface contamination while Ti2p signals demonstrate the presence of the $TiO_2$ oxide layer.

Biofilm contamination of Ti surfaces significantly increased C and N levels at the expense of O and Ti, indicating that the contaminants were mainly organic in nature (FIGS. 60A and B). Ti2p signal almost disappeared from the spectra surveys of biofilm-contaminated surfaces indicating that the biofilm covers entirely the Ti surfaces with the organic contaminants (FIG. 60A).

Note that the order of the columns in the bar chart in FIG. 60B corresponds to that set out in legend presented between (B) and (C). Also, in the bar chart, sa: significantly different from control (clean Ti) group, b: significantly different from biofilm-contaminated group, c: significantly different from Ti surfaces brushed for 1 minute, and d: significantly different from Ti surfaces brushed for 2 minutes ($p<0.05$).

Optimization of Brushing Time

Brushing Ti surfaces for 1 minute significantly decreased the levels of C and N and increased the concentrations of O and Ti (FIG. 60B). Increasing the brushing time to 2 and 5 minutes did not achieve further cleaning benefits but it induced surface scratches as seen on SEM images (FIG. 60C). Thus, the brushing time was fixed to 1 minute.

Optimization of Implant-Paste Formulation

The composition of the NMP gel was optimized as mentioned above to obtain an alkaline pH of 9.6. to 10% w/w.

The biofilm-contaminated surfaces were brushed using the optimized NMP gel (10% with respect to the water content) with and without hydrated silica. SEM images showed that surfaces cleaned with the MNP gel and the gel with 30% hydrated silica were clean without noticeable changes in their topography (see FIG. 61). Samples cleaned with the gel containing 30% hydrated silica were significantly different from the contaminated samples in terms of elemental composition as shown by XPS, they showed higher levels of Ti, 0 and lower levels of C, N, silica (Si) and magnesium (Mg). The MNP gel with less silica also decreased C and N levels but they were less efficient than the gel containing 30% hydrated silica. On the other hand, higher concentrations of silica (>30%) did not improve the cleaning performance but caused surface contamination with implant-paste residues including Si. Small arrows in FIG. 61 indicate the areas where the remnant silica accumulates on Ti surfaces.

Figure 62:
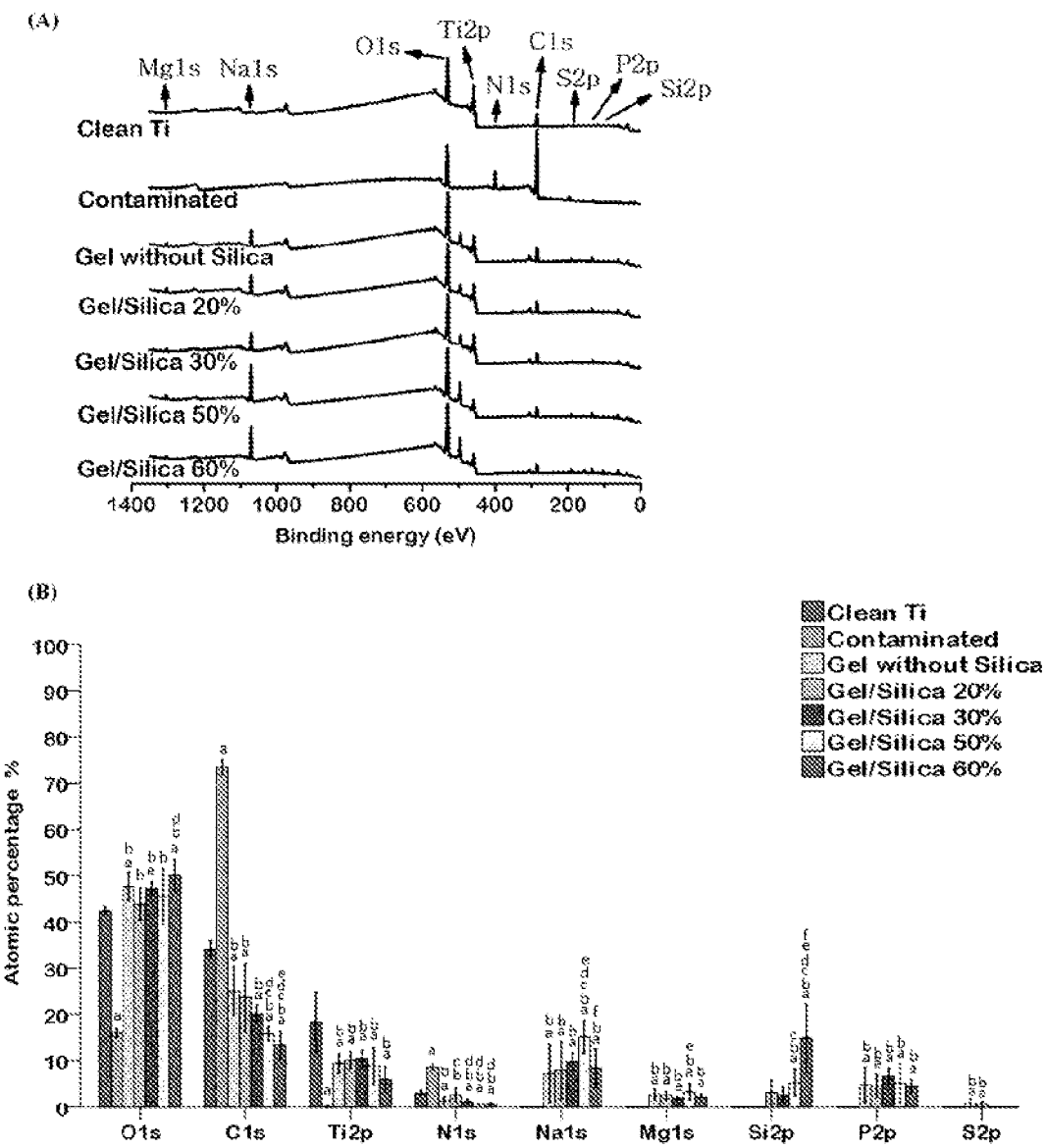
FIG. 62 shows XPS surveys (A) and a bar chart (B) comparing the cleaning efficiency of the NMP gel and the gel containing different concentrations of hydrated silica (Brushing time was 1 minute)

This is also visible on FIG. 62. Note that the order of the columns in the bar chart in FIG. 62 (from left to right) corresponds to that set out from top to bottom in the legend. Also, in the bar chart, a: significantly different from control group, b: significantly different from biofilm contaminated group, c: significantly different from NMP gel group, d: significantly different from Ti surfaces brushed with the gel containing 20% hydrated silica, e: significantly different from Ti surfaces brushed with the gel containing 30% hydrated silica, and f: significantly different compared to Ti surfaces brushed with the gel containing 50% hydrated silica ($p<0.05$).

Based on these results, the optimized implant-paste formulation was the one containing 10% NMP gel and 30% hydrated silica.

Cleaning Uncontaminated (Control) Samples with the Optimized Implant-Paste

Figure 63:
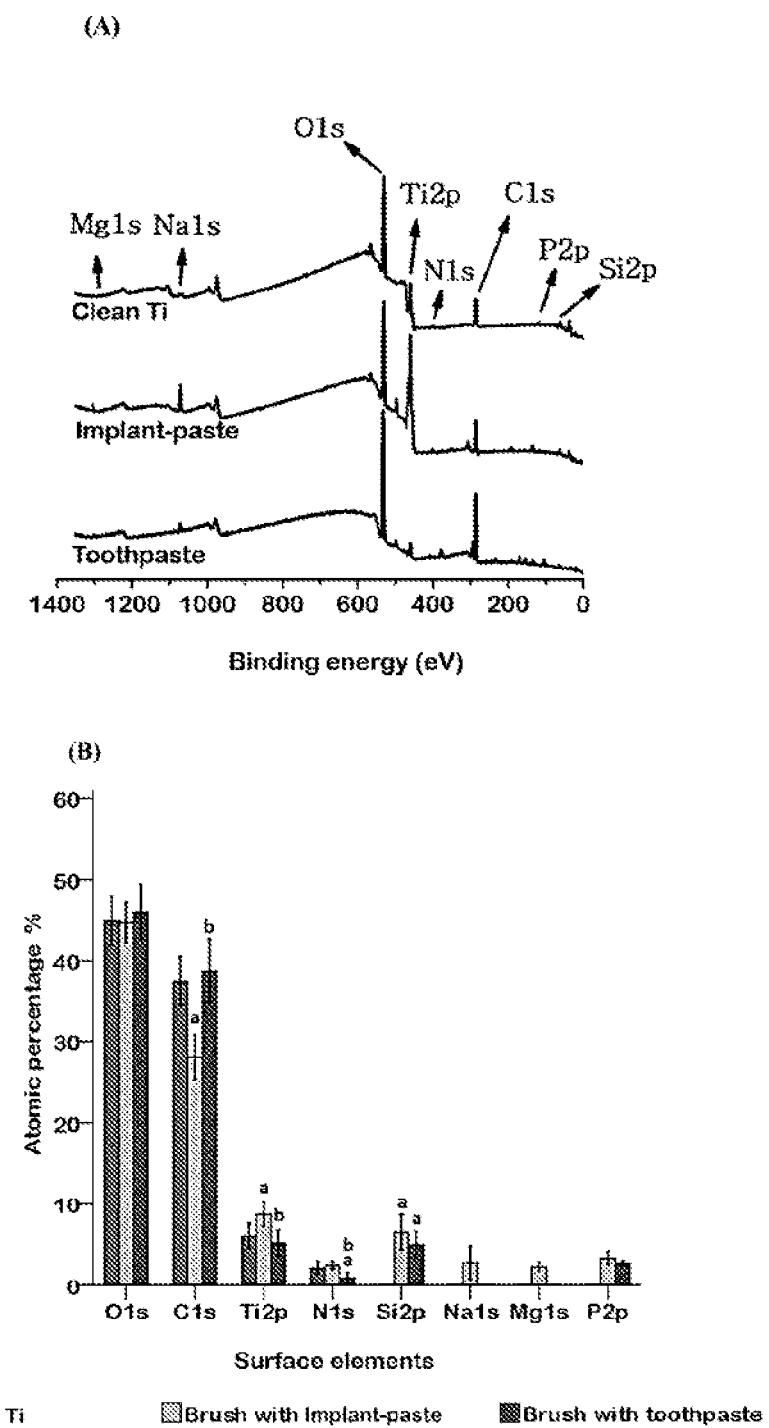
FIG. 63 shows XPS surveys (A) and a bar chart (B) showing the change in the elemental composition of uncontaminated Ti surfaces after cleaning them with the rotary brush and optimized implant-paste (NMP gel containing 30% hydrated silica) and a commercial toothpaste (Colgate), brushing time was 1 minute.

Brushing uncontaminated Ti with the optimized implant-paste increased the surface levels of Ti while decreasing those of C (see FIG. 63). In this figure, a: significantly different from control group.

The commercial toothpaste did not show a change in Ti or C levels.

Figure 64:
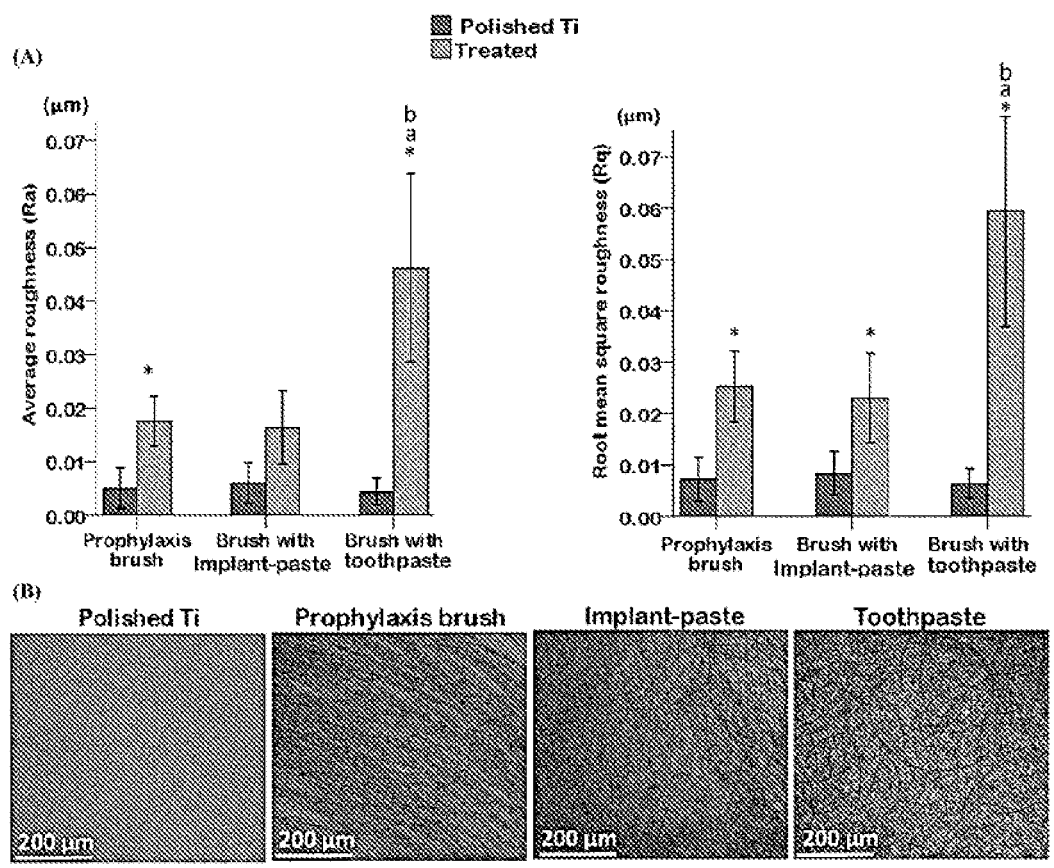
FIG. 64 shows bar charts (A) and confocal laser scanning microscope images (B), comparing the surface roughness of polished Ti surfaces after cleaning with the prophylaxis brush, the optimized implant-paste (NMP gel containing 30% hydrated silica) and commercial toothpaste (Brushing time is 1 minute)

This indicates that the optimized implant-paste is also able to remove the carbon-containing compounds that are adsorbed from atmosphere and usually detected on clean Ti surfaces without inducing a significant increase in their roughness as shown with confocal microscopy (see FIG. 64). In this figure: *: significantly different from clean Ti surfaces, a: significantly different from Ti surfaces cleaned with the prophylaxis brush, b: significantly different from Ti surfaces brushed with optimized implant-paste ($p<0.05$).

The Optimized Implant-Paste Vs Colgate Toothpaste

The optimized implant-paste significantly reduced the atomic concentration of surfaces' contaminants (C and N) and increased the O and Ti levels. However, it did not induce any significant change in the Ti surface roughness (see FIG. 64). Both results contrast with those obtained for surfaces cleaned with the brush alone or the brush with Colgate toothpaste (FIGS. 65A and B). The toothpaste significantly increased the C levels and surface roughness of Ti.

Figure 65:
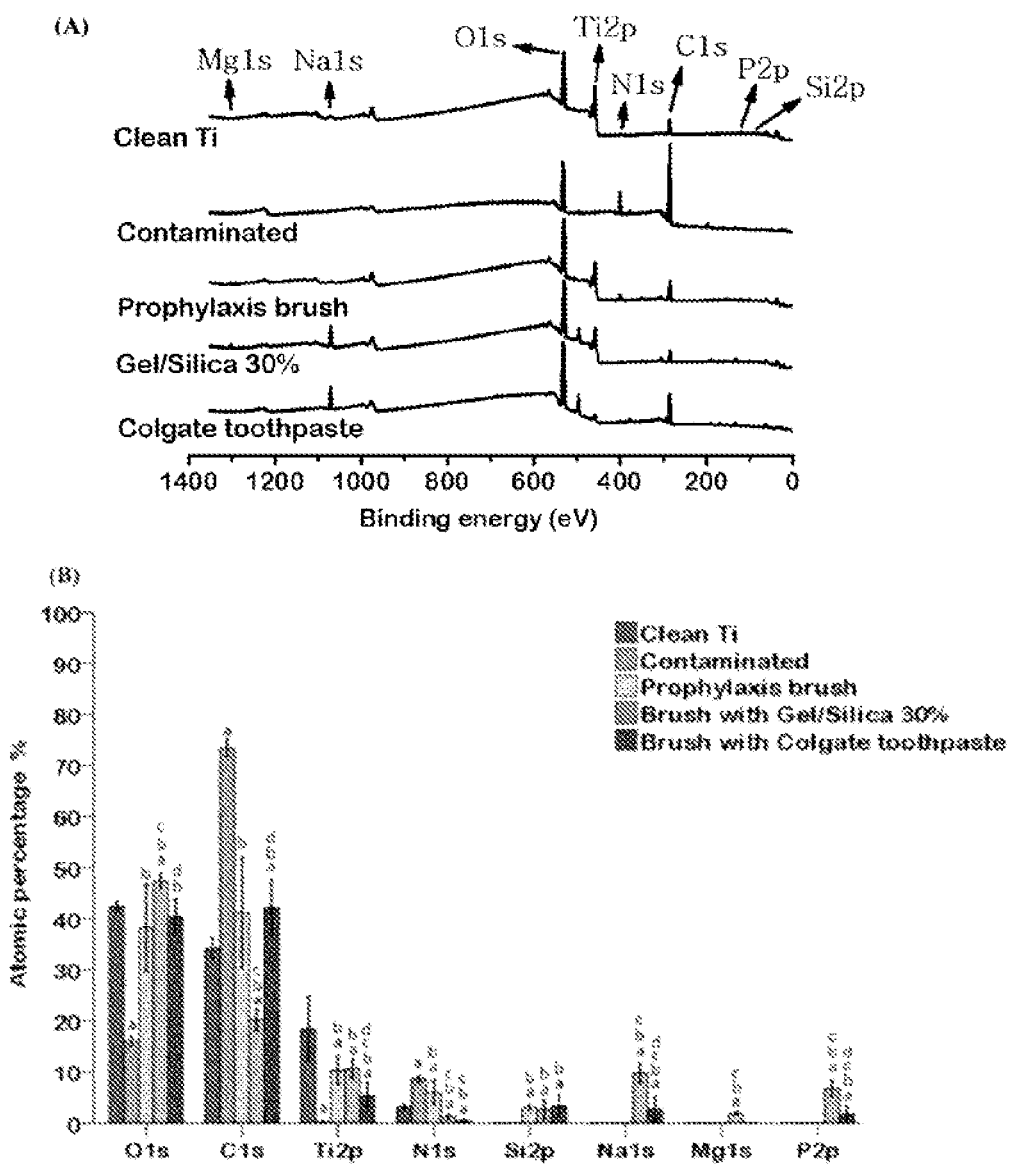
FIG. 65 shows XPS surveys (A) and a bar chart (B) comparing the cleaning efficacy of the prophylaxis brush, the optimized implant-paste and Colgate toothpaste (brushing time was 1 minute)

Note that the order of the columns in the bar chart (from left to right) of FIG. 65 corresponds to that set out in legend (from top to bottom). Also, in the bar chart, a: significantly different from control group, b: significantly different from biofilm-contaminated group, c: significantly different from Ti surfaces cleaned with the prophylaxis brush, d: significantly different from Ti surfaces brushed with the optimized implant-paste ($p<0.05$).

The optimized implant-paste and Colgate toothpaste were able to remove bacteria from biofilm-contaminated Ti surfaces reaching levels of bacteria comparable to those found prior to biofilm contamination (FIGS. 66A and B).

Figure 66:
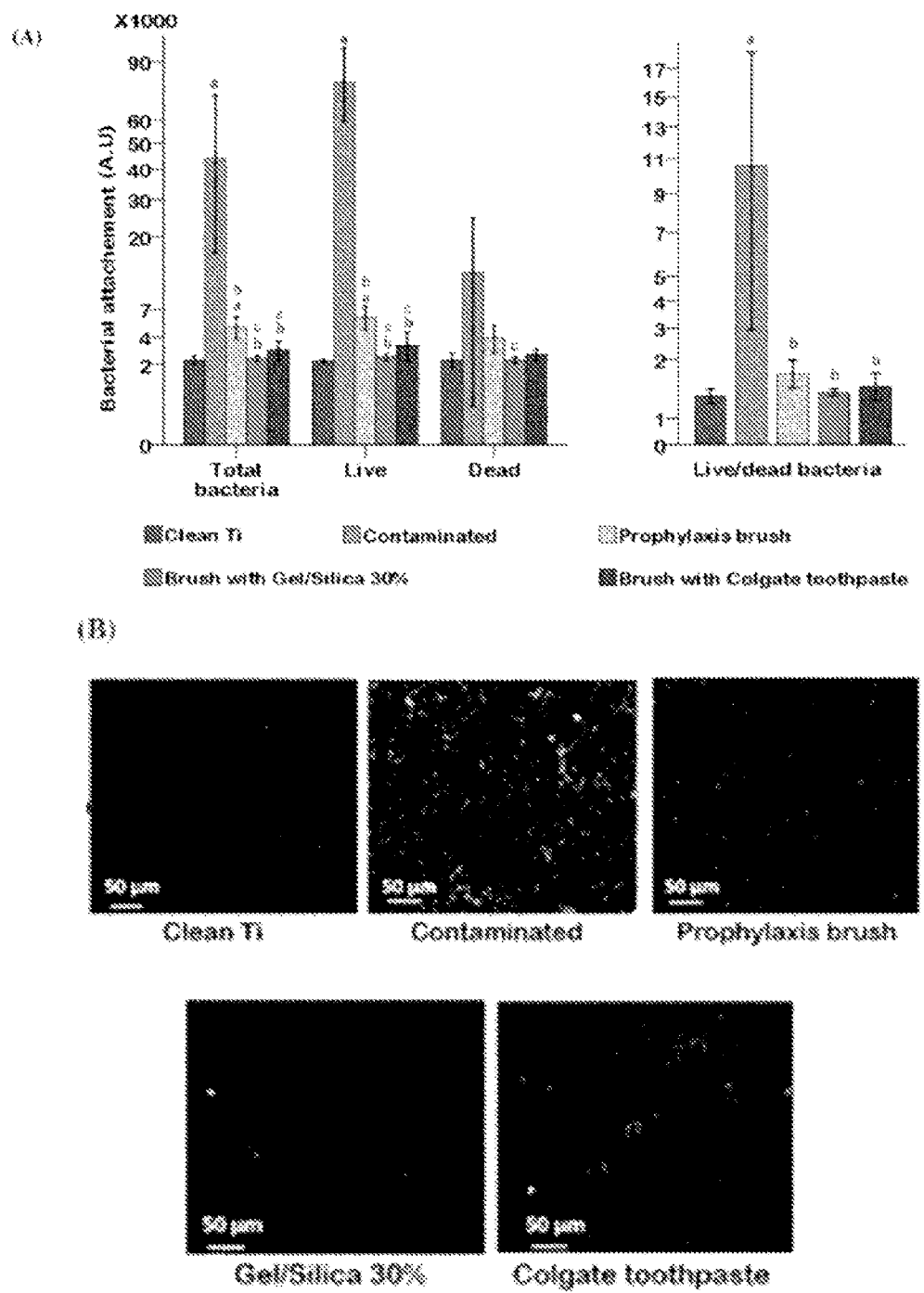
FIG. 66 shows bar charts (A) and live dead staining (fluorescence) images (B) comparing the bacterial removal efficiency of the prophylaxis brush, the optimized implant-paste and Colgate toothpaste (brushing time was 1 minute)

Note that the order of the columns in the bar chart (from left to right) of FIG. 66 corresponds to that set out in legend ($1^{st}$ line and then $2^{nd}$ line from left to right) presented between (A) and (B). Also, in the bar chart, a: significantly different from control group, b: significantly different from biofilm-contaminated group, c: significantly different from Ti surfaces cleaned with the prophylaxis brush, d: significantly different from Ti surfaces brushed with the gel containing 30% hydrated silica ($p<0.05$).

Figure 61:
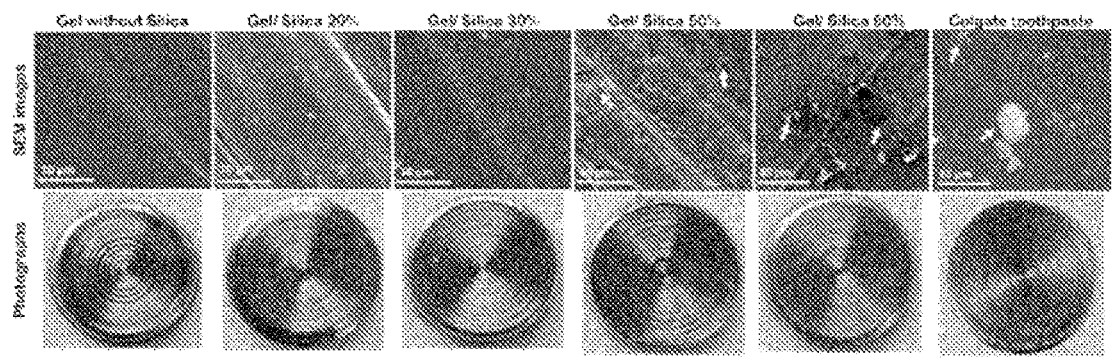
FIG. 61 shows Scanning Electron Microscope images (magnification ×10,000, top row) and photographs (bottom row) showing the topography of the biofilm-contaminated Ti surfaces after brushing with the NMP gel, the gel containing different concentrations of hydrated silica and Colgate toothpaste (brushing time was 1 minute)

SEM images showed surfaces scratches and toothpaste residues on surfaces cleaned with Colgate toothpaste but no scratches or residues could be seen with the optimized implant-paste (FIG. 61).

Discussion

Here we present a novel implant-paste specially designed and optimized for implant surface decontamination. It effectively disinfects contaminated titanium implants without apparent negative impacts on their surface integrity.

In this study, we used in vivo biofilm model because it offers the opportunity to evaluate implant surfaces in realistic clinical conditions; formation of composite plaque, co-adherence of microorganisms and salivary pellicle under the removal forces of salivary flow and chewing activities 29. Several in vitro biofilm models have been tested and validated to study the implant surface bacterial interactions 30-32. This includes for instance the commonly used microtiter plate-based systems 33. However, they fail to precisely simulate the complex structure of biofilm, the dynamics of its pathogenicity and ecological determinants 34, 35.

Prophylaxis instruments such as brushes and rubber cup are used to remove biofilms attached to implant surfaces with or without using prophylaxis pastes. In this study, we used rotary brushes for cleaning Ti surfaces because they are inexpensive and accessible compared to titanium brushes and their plastic bristles should be gentile on Ti. Rotating cups were found to leave remnants of rubber particles on the implant surfaces after cleaning 5, 36. In addition, some cup materials are too abrasive and can cause Ti surface damage 37.

Figure 60:
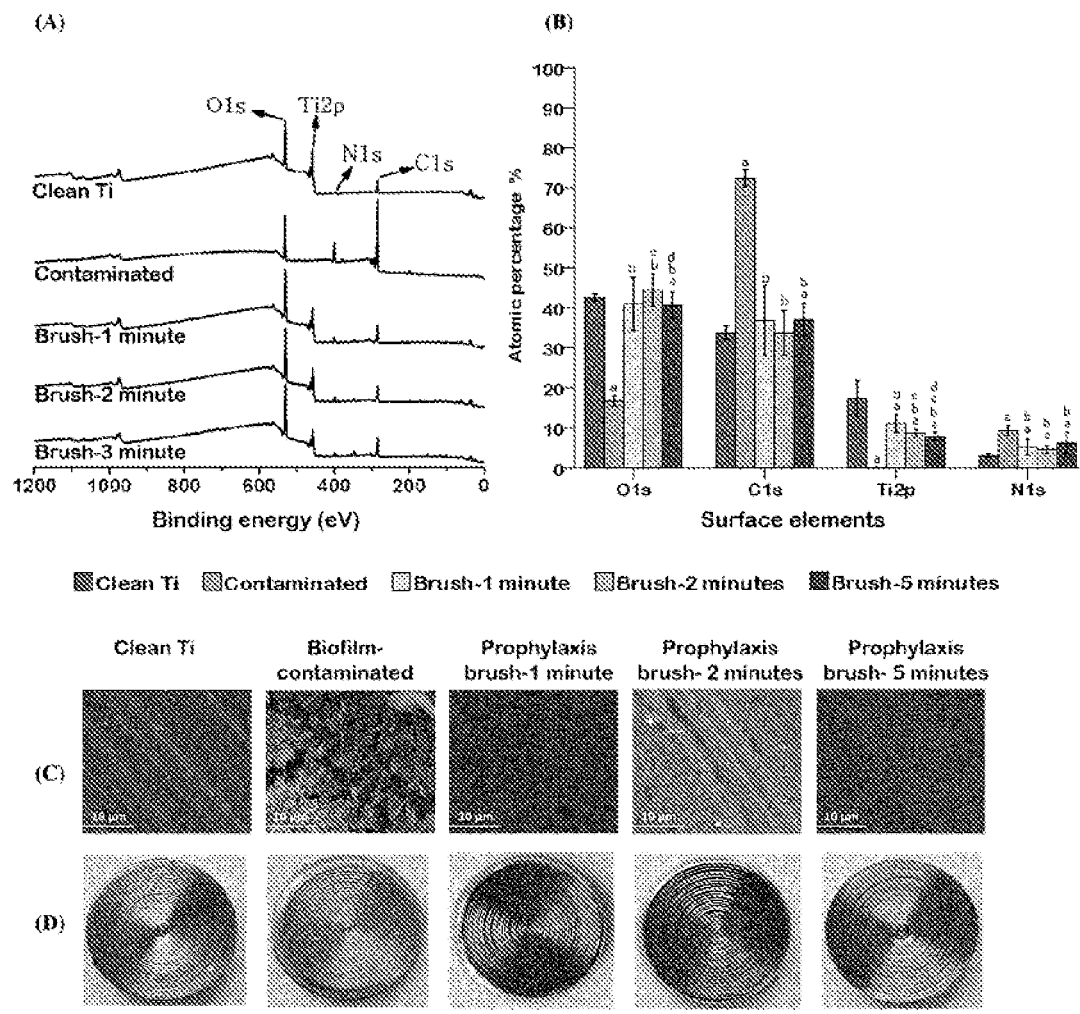
FIG. 60 shows X-ray Photoelectron Spectroscopy (XPS) surveys (A), a bar chart (B), scanning Electron Microscope images at a magnification of ×10,000 (C) and photographs (D) illustrating the cleaning effect of rotary prophylaxis brush at different brushing time on the elemental composition and topography of biofilm-contaminated Ti surfaces.

In the present study, prophylaxis bushes were initially used to decontaminate the implant surfaces without a paste. The purpose of this procedure was to optimize the brushing time and exclude the possible damaging effect of brushing technique. To the best of our knowledge, this is the first study that optimized the time required for Ti decontamination using the prophylaxis brush. The results showed that brushing the biofilm-contaminated implant surface for 1 minute was able to remove the Ti surface contaminants efficiently (FIGS. 60 A and B), without inducing surface scratches or changes (FIGS. 60 C and D).

However, brushing for more than one minute induced visible scratches on the Ti surfaces without improving the cleaning outcomes. Indeed, increasing the brushing time to 2 and 5 minutes negatively affects the Ti surface topography and induced surfaces scratches (FIG. 60). This finding could be attributed to the softness of Ti metal and its poor resistance to physical wear. Therefore, the brushes induced surface scratches on Ti surface when brushing strokes have been increased more than 2500 rpm. To confirm these results, the surface roughness of polished Ti surfaces was measured before and after the one-minute brushing, which showed a significant increase in their roughness. However, the average surface roughness (Ra) after brushing was only $0.018 \pm 0.004$ μm, which falls within the reported threshold Ra (0.2 μm) that does not cause further alteration in surface microbiological load 40.

Accordingly, brushing contaminated Ti implants surfaces for 1 minutes (2500 rpm) was able to decontaminate them without causing mechanical abrasion, though the complete removal of contaminants and re-establishment of the Ti original chemistry were not achieved. This indicates the limited effectiveness of brushes in decontaminating Ti surfaces, which calls for the use of a dentifrice or a prophylaxis paste.

A dentifrice is usually combined with brushes to adjunct the physical removal of plaque and stains through their chemical and physical additives, or to apply therapeutic and preventive agents to tooth surfaces. The dentifrice needs two main ingredients to achieve the mechanical cleaning; an abrasive agent and thickener to hold the abrasives in suspension during brushing. In this study, we developed and optimized prophylaxis paste to decontaminate implant surfaces "implant-paste" and enhance the cleaning efficiency of the brush. For the development of this implant-paste, the sole thickener was composed of an inorganic, silicate free Nanocrystalline Magnesium Phosphate (NMP) gel. The gel composition was optimized to obtain an alkaline pH of 9.6 because the corrosion resistance of Ti is high at this pH. In addition, the implant-paste can be in contact with intraoral structures and teeth for several hours when used for daily cleaning of Ti implants. Consequently, ideally, this optimized implant-paste to have a relatively alkaline pH to minimize potential tooth or implant damage.

The optimized NMP gel has similar biocompatibility and thixotropic properties of Laponite (silicate clays); the most used inorganic thickener in toothpastes. However, the optimized NMP gel has a stable consistency without the need for additional organic thickeners. This is an advantage of our novel gel over the clays-based toothpastes that require organic thickeners (i.e. xanthan gum) to provide optimal consistency. The incorporated organic compounds could adhere to the implant surfaces complicating their decontamination.

The other key component of the implant-paste that contributes to the physical removal of biofilm is the abrasive agent. For our implant-paste, hydrated silica nanoparticles were chosen as abrasives. It is a relatively safe, nontoxic ingredient and mostly compatible with other ingredients, such as glycerine and fluoride. Moreover, low concentration of silicates shows osteoconductive properties that help to induce and accelerate bone regeneration.

We used hydrated silica nanoparticles (~200-300 nm) used as a polishing agent and optimized their content to obtain mild abrasiveness that removes plaque without scratching implant surfaces. It was also used to increase the gel viscosity and to benefit from their osteoconductivity properties. The study results showed that the best decontamination outcomes were obtained with the 10% NMP gel containing 30% hydrated silica. This formula showed an efficient removal of the organic contaminants from Ti surfaces and the least morphological/topographical changes (FIGS. 61 and 62).

The cleaning effectiveness of the optimized prophylaxis paste was further confirmed by its ability to remove carbon-containing compound from clean Ti surfaces (controls), using the optimized brushing time, without causing alteration in their roughness (FIG. 64). The significant drop in carbon level (FIG. 63) after cleaning confirms the effectiveness of the implant-paste in removing the carbon-containing compound that are normally adsorbed on Ti surface from atmosphere.

The superior decontamination efficiency of the implant-paste on biofilm-contaminated surfaces in comparison to the rotary prophylaxis brush and the brush with a commercial toothpaste was also observed (FIG. 65). This confirms that the optimized implant-paste formulation is able to remove the surface organic contaminants regardless of the mechanical action of the rotary brush. On the other hand, the significant increase in the carbon levels after cleaning these surfaces with Colgate toothpaste indicates that the regular toothpastes further contaminate the Ti surface. This result could owed to the organic content of the toothpastes that are usually incorporated for thickening, binding or flavoring benefits. This confirms the superiority of the implant-paste developed in this study, due to its inorganic nature, over the currently available pastes.

The bacteria attached to the surfaces brushed with the optimized implant-paste and Colgate toothpaste were found to be comparable to that found on uncontaminated Ti surfaces (FIG. 66). This result is in agreement with a previous study that indicated the superiority of a toothbrush and dentifrices over different ultrasonic scalers in reducing bacterial load from contaminated implant surfaces.

Conclusions

The optimized inorganic implant-paste shows superior efficiency in decontaminating implants than organic-based Colgate toothpaste without damaging their surfaces integrity. The new inorganic implant-paste developed in this study can remove biofilm from contaminated Ti implants without affecting their surface integrity. Cleaning dental implants with current organic-based toothpastes contaminates the implants surfaces, changing their surface charge, roughness and chemistry, which could have negative impact on re-osseointegration.

To the inventor's knowledge, this is the first paste ever specially designed and optimized for implant surface decontamination. The optimized inorganic implant-paste shows 2 times more effective in decontaminating Ti, 3 times less abrasive than a regular toothpaste and 2 times less bacteria than brushing alone. Therefore, it shows superior efficiency in decontaminating Ti implants than organic-based toothpaste without damaging their surfaces.

Example 4—Controlled Release of Drugs

Above, we showed that sodium magnesium phosphate nanocrystals (gel) are osteoinductive, thixotropic colloidal suspension and can be injected through high gauge needles and therefore can be used for minimal invasive interventions. Here, we investigated how this gel can control the release of local anesthetic (mepivacaine) in-vitro and in-vivo. We also investigated if the NMP loaded with mepivacaine could shorten post-fracture mobilization time, reduce postoperative pain and accelerate bone healing with the ultimate goal of developing an injectable bone regeneration biomaterial with analgesic property.

Materials and Methods

The gel (NMP) for the in vitro release was prepared by dissolving 54 mg of $Mg(OH)_2$ (0.93 mmol, mole fraction 0.13) in 1.65 mL of $H_3PO_4$ 1.5 M (2.47 mmol, mole fraction 0.34), and subsequently 2.32 mL of NaOH 1.5 M (3.78 mmol, mole fraction 0.53) was added under vigorous stirring.

For the in vitro drug release, mepivacaine hydrochloride was dissolved in 1 mL of gel previously prepared to reach different mepivacaine concentration. The pH of the resulting thixotropic colloidal suspension before the addition of mepivacaine was 7.95, while after the addition of the drug changed to 7.1. The gel+mepivacaine was placed in a Pur-L-Lyzer™ dialysis tube with a molecular weight cut-off of 12000 Da, while the control group is represented by the mepivacaine dissolved in PBS (2% w/v) and placed in a dialysis tubes with the same molecular weight cut-off. The tubes were incubated in 30 mL of phosphate buffer saline solution (PBS) at 37° C., and the solution was changed at different time points comprised between 0 and 168 hours. In order to calculate the amount of drug released, the extracted solutions were analyzed with UV-Vis spectroscopy following the absorption of mepivacaine at 263 nm. All experiments were done in triplicates.

The analgesic action of the mepivacaine with gel was assessed in vivo using the mouse-hindpaw-model. Twelve mice were assigned into four groups (n=3, each); saline, mepivacaine, gel and gel+mepivacaine. Each mouse received a single injection of the assigned treatment (5 μL subcutaneously) into the planter surface of the hindpaw. Due to the small volume injectable inside the hindpaw the amount of mepivacaine dissolved inside the gel was increased from 2 to 8% w/v. This drug increase drastically changed the pH of the final gel+mepivacaine colloidal dispersion from 7.5 to 4.1, being too acidic and subsequently destabilizing the gel structure provoking the precipitation of the gel. To address this problem, the gel for the in vivo experiment was synthesized by dissolving 69 mg of $Mg(OH)_2$ (1.18 mmol, mole fraction 0.16) in 1.65 mL of $H_3PO_4$ 1.5 M (2.47 mmol, mole fraction 0.31), and subsequently 2.9 mL of NaOH 1.5 M (4.35 mmol, mole fraction 0.53) was added under vigorous stirring. For the in vivo drug release, 80 mg of mepivacaine hydrochloride were dissolved in 1 mL of gel previously prepared (8% w/v). The pH of the resulting thixotropic colloidal suspension before the addition of mepivacaine was 9.6, while after its addition the pH decreased to 7.6, being more compatible with physiological pH. The sensitivity to thermal stimuli was tested using radiant heat at different time points comprised between 0 and 120 minutes.

The effects of NMP alone, NMP combined with mepivacaine and mepivacaine alone, on post-fracture mobilization, postoperative pain and bone healing were assessed in vivo using a standardized mice tibial fracture model (St-Arnaud, The Journal of steroid biochemistry and molecular biology 121, 254-256 (2010)). Thirty-two mice were randomly assigned into four groups (n=8, each); saline, mepivacaine, NMP and NMP+mepivacaine. Thirty minutes prior to surgical intervention, each mouse was injected with Carprofen (20 mg/kg; SC).

The animal was then anesthetized with isoflurane (3-5% at the induction time and 2-2.5% during the maintenance period). After the animal shows signs of being fully anesthetized, the right leg was shaved and disinfected using chlorohexidine, then, the animal was covered with a sterile drape. A longitudinal skin incision was made in order to expose the right patellar tendon. The tendon was dissected and elevated in order to expose the proximal tibial tuberosity. A 27-gauge spinal needle was introduced into the intramedullary canal of the tibia. A tibial fracture was performed in a standardized manner using a twister (Hiltunen et al., Journal of orthopaedic research 11, 305-312 (1993)). Following creation of fracture, a single post-operative injection of the assigned treatment (20 μL) into the fracture site and the surgical site was closed using 5-0 Vicryl.

Post-operative Animals' pain perception and locomotion were evaluated, at different time point; hours, 24 hours, 3 days, one week and two weeks post fracture, by assessing mice guarding (Yasuda et al., Journal of pain research 6, 161 (2013)) and weight bearing per each leg, respectively. Animals were allowed to habituate to the testing room for at least one hour prior to handling. Guarding behavior was assessed as following; each mouse was placed individually in a clear plastic box on an elevated stainless steel mesh. Both paws (of the fractured and non-fractured legs) were observed closely for 1-minute periods every five minutes for 60 minutes. A score of 0, 1, or 2 was given according to the postural position of each paw in most of the 1-minute scoring periods. If the injured side is blanched or distorted by the mesh, 0 score was given. If the paw is completely off the floor, 2 score was given. If the paw touches the floor without blanching or distorting, 1 score was given. The sum of the 12 scores (one score every five minutes for 60 minutes) (0-24) will be obtained during the 1-hour session for each paw. The final guarding score was obtained by subtracting the score of the injured side from that of the non-injured hind paw (Yasada, supra).

Weight bearing test was performed as following; an incapacitance meter (IITC.inc, CA, US) was used for determination of hind paw weight distribution. Mouse was placed in an angled plexiglass chamber positioned so that each hind paw rest on a separate weighting plate. The weight exerted by each hind limb was measured and averaged over a period of 5 seconds. The change in hind paw weight distribution was calculated by determining the difference in the amount of weight (g) between the left and right limbs. Change in hind paw weight distribution between the left (fractured leg) and right (control) limbs was used as an index of pain in the fractured leg (Bove et al., Osteoarthritis and cartilage 11, 821-830 (2003)). Two weeks following fracture, mice were euthanized and tibial explants were assessed for bone healing and fracture resistance using micro-CT and three point pending test, respectively.

Results and Discussion

The in vitro release experiment of mepivacaine demonstrates that, compared to the control formulation, the gel controlled the release of mepivacaine.

Figure 67:
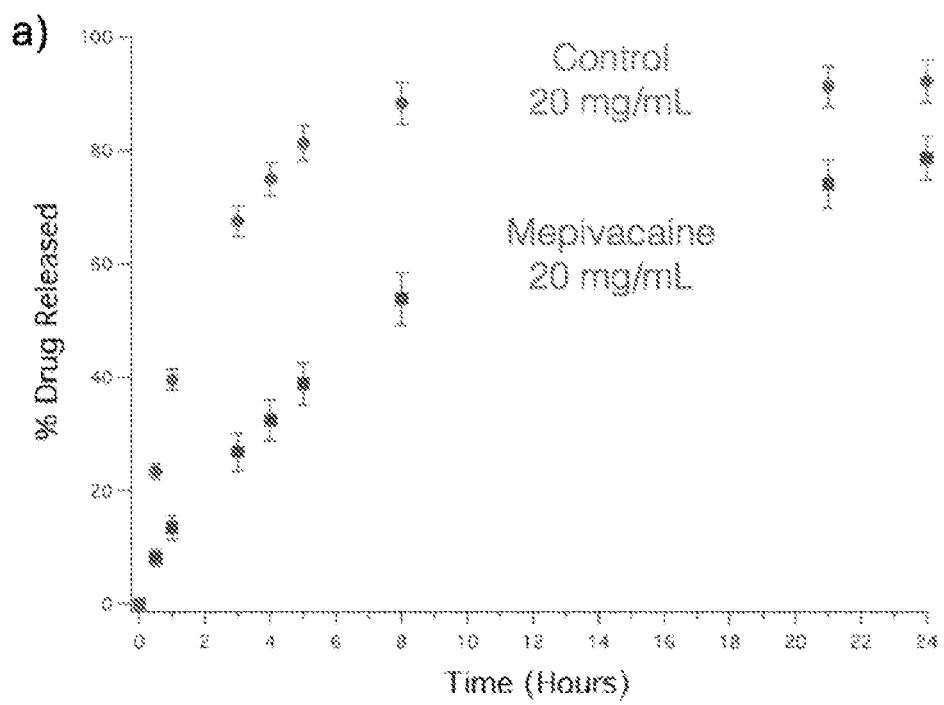
FIG. 67 shows the drug release in vitro showing that the gel can control the liberation of the local anesthetic (loading of NMP with mepivacaine)

As can be seen in FIG. 67, after 8 hours the release of mepivacaine in the control group was almost complete with a total release of 90±5% of drug, while the group of gel+mepivacaine released 50±4% of the drug. Local anesthetics, such as mepivacaine and bupivacaine, have a short duration effect, for example 2 hours. The release profile was slower for gel+mepivacaine than the control group indicating a prolonged release effect, and thus a possible prolongation of the duration of the therapeutic effect of mepivacaine.

Figure 68:
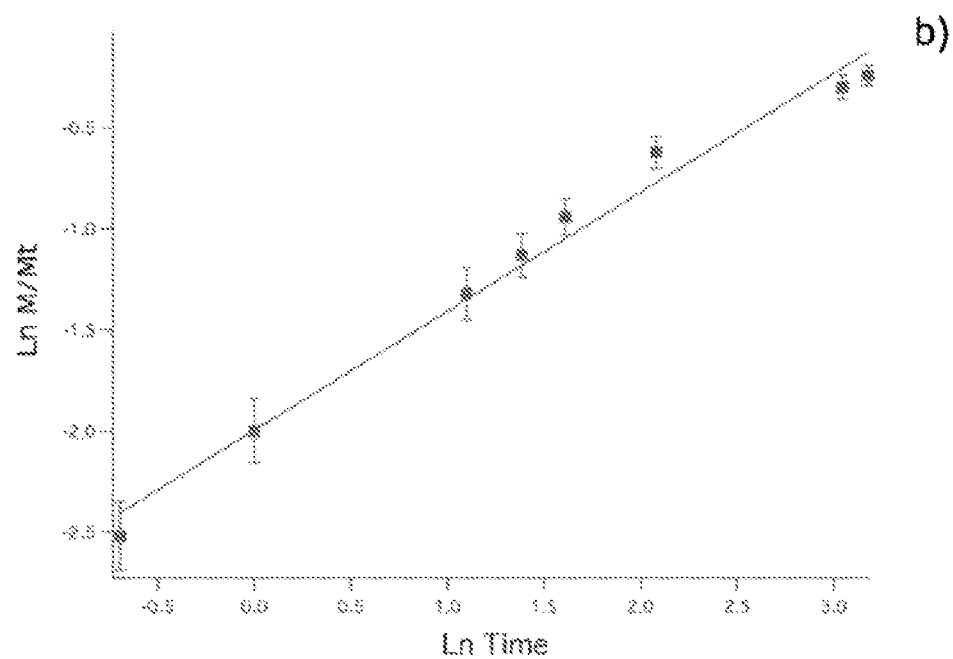
FIG. 68 is the Korsmeyer-Peppa's fitting for the cumulative drug released from gel+mepivacaine samples.

The Korsmeyer-Peppa's model was used for the fitting of the cumulative drug release as shown in FIG. 68. The equation of this model is $M/M_r = kt^n$ where $M/M_r$ is the cumulative amounts of drug released at time t, k is a constant incorporating structural and geometrical characteristics of the drug dosage form, and n is the release exponent that identify the release mechanism. The linear fitting gave an exponent n=0.58 (R=0.99) and according to the Korsmeyer-Peppa's model when n is 0.5<n<1 the mass transport is regulated by non-Fickian diffusion. This result might indicate some physicochemical interaction between the drug and the gel which is responsible of the controlled released.

Figure 69:
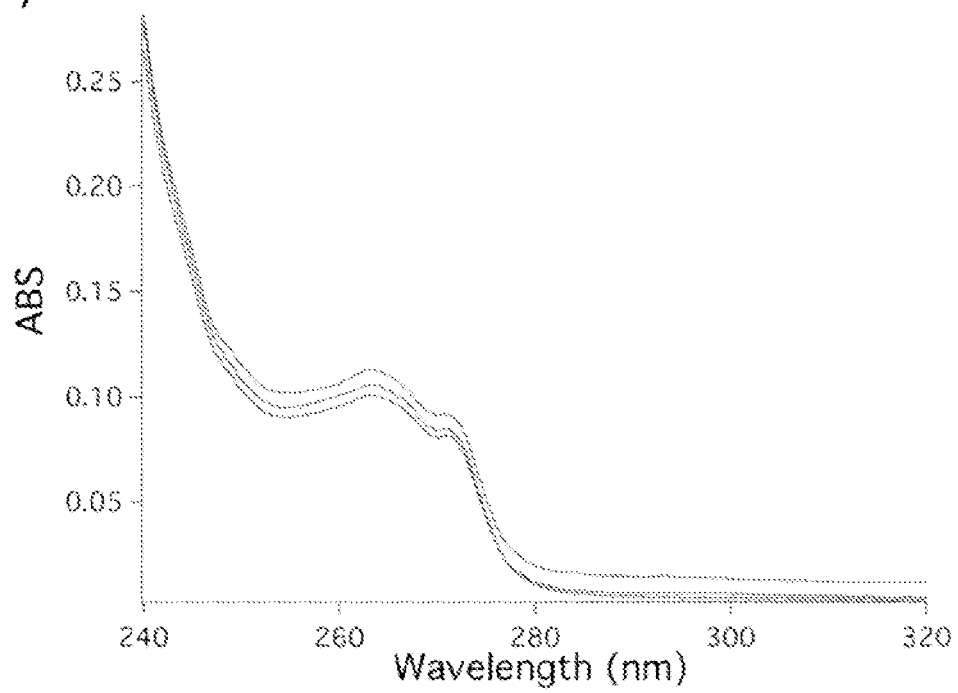
FIG. 69 shows the UV-Vis spectra of the mepivacaine released from the gel after 24 hours.

The stability of mepivacaine in contact with the gel was checked after 24 hours from the beginning of the drug release experiment. The UV-Vis spectra show the molecular integrity of the drug indicating that mepivacaine is compatible with the gel (FIG. 69).

Figure 70:
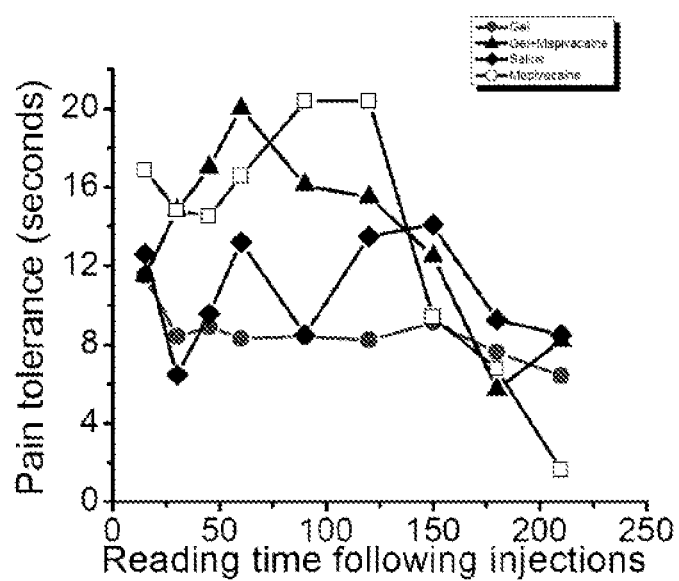
FIG. 70 show the results of the radiant heat test used to evaluate the heat tolerance of mice in vivo using the mouse-hindpaw-model; these results showed that the NMP loaded with mepivacaine provides analgesia and the analgesic action of mepivacaine was prolonged by NMP.

Radiant heat test showed that the gel loaded with mepivacaine provides analgesia effect to mice and the analgesic action effect of the drug can be prolonged using the gel (FIG. 70).

Figure 71:
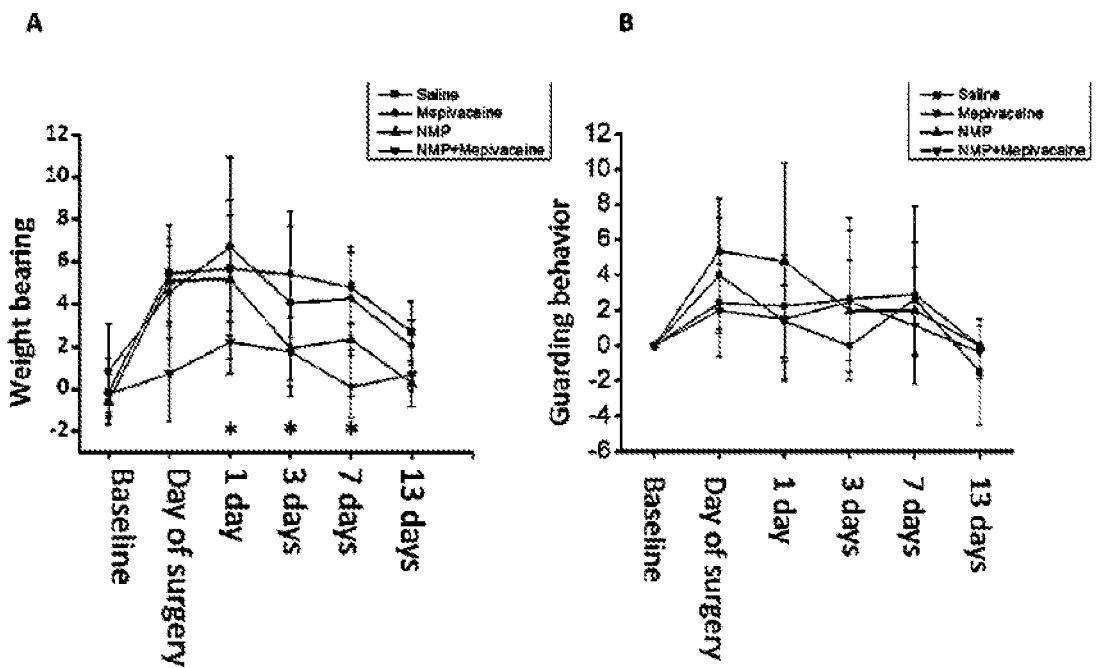
FIG. 71 shows A) weight bearing test results and B) guarding test results for saline, mepivacaine, NMP, and NMP+mepivacaine treatment.

NMP combined with mepivacaine improved weight bearing on fractured leg and reduced post-operative pain (FIG. 71).

Figure 72:
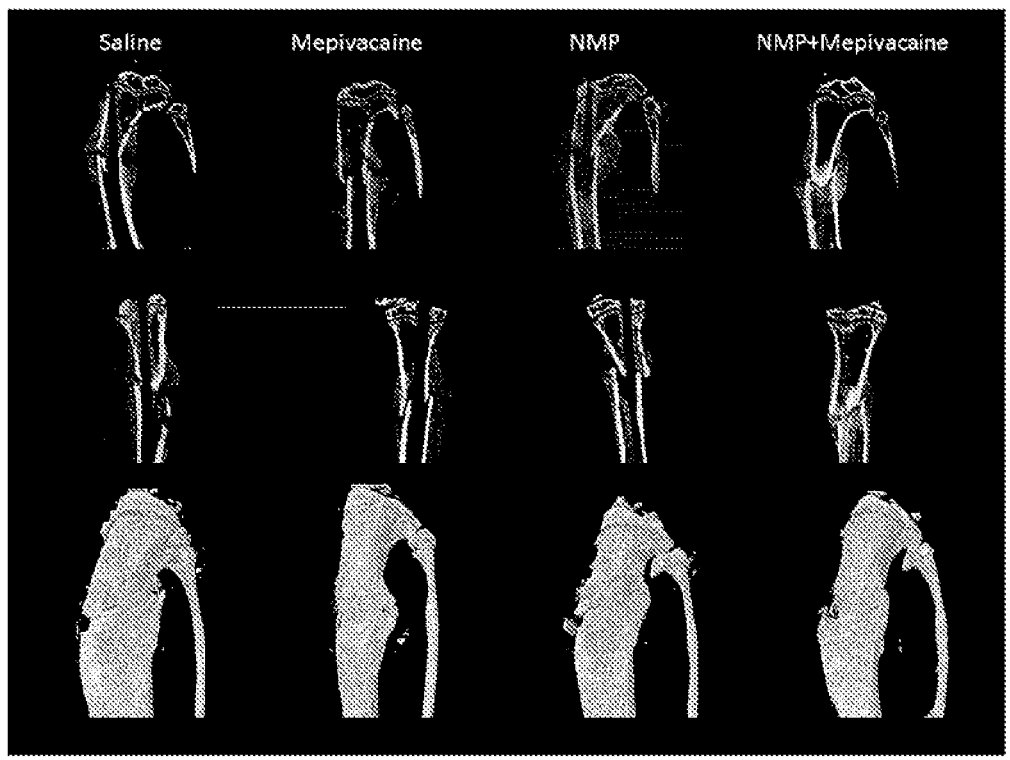
FIG. 72 shows micro-CT sagittal, coronal sections and 3 D reconstructions showing bone formation at fracture site after saline, mepivacaine, NMP, and NMP+mepivacaine treatment.

NMP and NMP+mepivacaine accelerated fracture healing. Indeed, Micro-CT sagittal, coronal sections and 3 D reconstructions showed that bone formation at fracture site was higher in NMP alone and in NMP combined with mepivacaine (FIG. 72).

Figure 73:
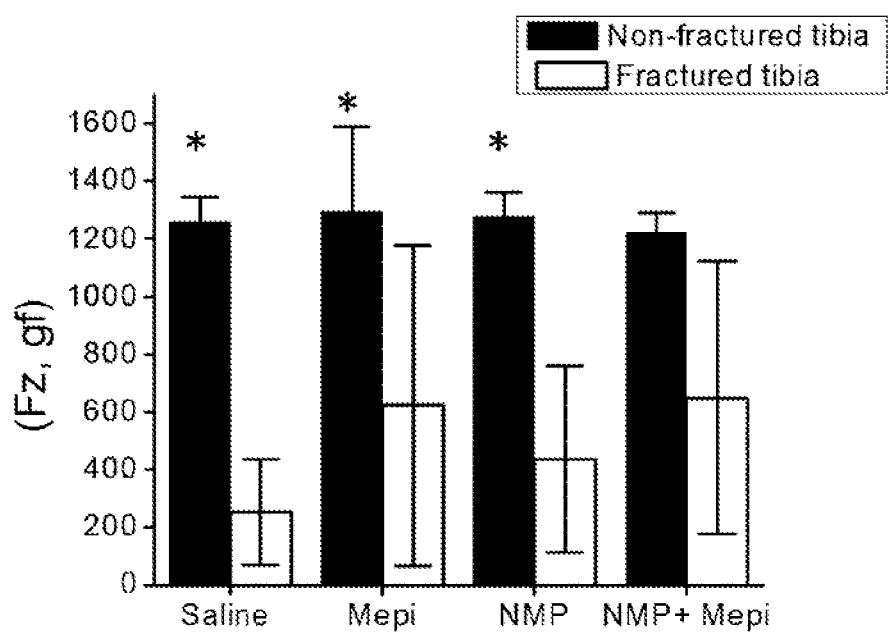
FIG. 73 shows 3-points pending test results after saline, mepivacaine, NMP, and NMP+mepivacaine treatment.

Force to fracture was significantly different between fractured and non-fractured tibia, among saline, mepivacaine and NMP groups (FIG. 73). However, there was no significant difference between fractured and on-fractured legs among NMP+Mepivacaine group.

Discussion and Conclusion

The result of in vitro experiment showed that the gel is able to control the release of mepivacaine better than the control.

The biomaterial described here was injected through high gauge needle into hindpaw of mice and provided effective analgesia to the mice treated with gel+mepivacaine.

In fact, the NMP was able to control the release of mepivacaine for up to 24 hours. Higuchi and Korsmeyer-Peppas models indicated that mepivacaine was released by diffusion. The mepivacaine released by NMP presented no change in its molecular structure as shown by UV-Vis spectra (FIG. 69), indicating that the drug was compatible with NMP. Radiant heat test showed that NMP loaded with mepivacaine provides analgesia and the analgesic action of mepivacaine was prolonged by NMP (FIG. 70). Guarding and weight bearing tests revealed that NMP loaded with mepivacaine shorten the mobilization time and reduce post-operative pain (FIG. 71). Micro-CT data showed that NMP loaded with mepivacaine, accelerated bone healing (FIG. 72). Three point pending test indicated that NMP loaded with mepivacaine enhanced fracture resistance (FIG. 73).

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

1) Acharya et al., Journal of International Oral Health 2014, 6, 36.
2) Aguzzi, C. et al., Appl Clay Sci. 2007, 36 (1-3), 22-36.
3) AlAbbas, F. M. et al., Journal of Pipeline Engineering, 2012. 11(1): p. 63.
4) Alonso-Cristobal et al., ACS App. Mater. Interfaces 2015.
5) A-Radha et al., J. Dent. 2012, 40, 146-153.
6) Amini et al., Crit. Rev. Biomed. Eng. 2012, 40 (5), 363-408.
7) Andersen et al., Acta orthopaedica 78, 187-192 (2007).
8) Aspenberg et al., Acta Orthopaedica73, 489-490 (2002).
9) Aspenberg, P. Avoid cox inhibitors after skeletal surgery! Acta Orthopaedica 73, 489-490 (2002).
10) Babic-Ivancic et al., Water Res. 2006, 40 (18), 3447-55.
11) Baran et al., Spectrochim. Acta A 2004, 60, 1001.
12) Barao et al., Clin. Oral Implants Res. 2012, 23, 1055-1062.
13) Barnes, J Non-Newton Fluid 1997, 70 (1-2), 1-33.
14) Barros et al., Clinical oral implants research, 2011. 22(11): p. 1221-1226.
15) Bassett et al., J Chem Soc 1933, 854-871.
16) Bassett et al., J Chem Soc 1933, 871-876.
17) Bassett et al., J Chem Soc 1933, 877-882.
18) Bergaya et al., Handbook of clay science. Elsevier: Amsterdam; London, 2006; p xxi, 1224 pages.
19) Blanc et al., J. Periodontal Res. 2014, 49, 323-332.
20) Bohner, Biomaterials 2009, 30 (32), 6403-6.
21) Bollen et al., Clin. Oral Implants Res. 1996, 7, 201-211.
22) Bove, S. et al., Osteoarthritis and cartilage 11, 821-830 (2003).
23) Brookshire et al., The Journal of prosthetic dentistry 1997, 78, 286-294.
24) Burgers et al., Clin. Oral Implants Res. 2010, 21, 156-164.
25) Campus et al., Caries Research, 2003.37(1): p. 66-70.
26) Coenye et al., J. Microbiol. Methods 2010, 83, 89-105.
27) Colombo et al., J. Med. Microbiol. 2013, 62, 1592-1600.
28) da Cunha et al., Biomaterials 2014, 35 (32), 8927-8936.
29) Davies et al, Med. Oral Patol. Oral Cir. Bucal. 2010, 15, e976-982.
30) Dawson et al., Adv. Mater. 2011, 23 (29), 3304-3308
31) Dawson et al., Adv. Mater. 2013, 25 (30), 4069-4086.
32) Ding et al., Chem. Mater. 2000, 12 (10), 2845-2852.
33) Dorozhkin et al., Angew. Chem. Int. Edit. 2002, 41 (17), 3130-3146.
34) Driessens et al., J. Mater. Sci. Mater. Med. 1995, 6 (5), 272-278.
35) Elias et al., J Mech. Behav. Biomed. 2008, 1, 234-242.
36) Fais et al., Journal of dentistry, 2012. 40(4): p. 265-275.
37) Faria et al., Brazilian oral research, 2012. 26(6): p. 498-504.
38) Feng et al., Biomaterials 2004, 25 (17), 3421-3428.
39) Figuero, Periodontology 2000, 2014. 66(1): p. 255-273.
40) Franceschi et al., Connect Tissue Res. 2003, 44, 109-116.
41) Fujita et al., J. Cell. Biol. 2004, 166 (1), 85-95.
42) Gaharwar et al., ACS Nano 2014, 8 (10), 9833-9842.
43) Gaharwar et al., Adv. Mater. 2013, 25 (24), 3329-3336.
44) Gedanken et al., Ultrason Sonochem 2004, 11 (2), 47-55.
45) Gerstenfeld et al., Journal of orthopaedic research 21, 670-675 (2003).

46) Ghezzi et al., Acta Biomater. 2012, 8, 1813.
47) Gosau et al., Clinical Oral Implants Research, 2010. 21(8): p. 866-872.
48) Gratzel, Nat. Mater. 2014, 13 (9), 838-842.
49) Greenwood et al., Chemistry of the elements; 2nd ed.; Butterworth-Heinemann: Oxford; Boston, 1997. p xxii, 1341 p.
50) Größner-Schreiber et al., Clinical oral implants research, 2009. 20(8): p. 817-826.
51) Guillou et al., Angew Chem Int Ed Engl 2001, 40 (15), 2831-2834.
52) Hase et al., Microbiology and Molecular Biology Reviews, 2001.65(3): p. 353-370.
53) Hefferren, J. Historical view of dentifrice functionality methods. J. Clin. Dent. 1998, 9, 53-56.
54) Heitz-Mayfield et al., Journal of Clinical Periodontology, 2008. 35(s8): p. 292-304.
55) Hiltunen, A., Vuorio, E. & Aro, H. T. A standardized experimental fracture in the mouse tibia. Journal of orthopaedic research 11, 305-312 (1993).
56) Hirsch et al., Chem Mater 2014, 26 (9), 2934-2942.
57) Hussein et al., Bone 2011, 48, 202.
58) Ida et al., J. Am. Chem. Soc. 2012, 134 (38), 15773-15782.
59) Idlibi et al., Biofouling, 2013. 29(4): p. 369-379.
60) Iwama et al., Cryst. Growth Des. 2010, 10 (8), 3471-3479.
61) Jang et al., ACS Nano 2014, 8 (1), 634-641.
62) Johannsen et al., Swedish dental journal, 1988. 13(6): p. 267-276.
63) Johnson-McDaniel et al., J Am Chem Soc 2013, 135 (5), 1677-1679.
64) Joska et al., Journal of Materials Science: Materials in Medicine, 2010. 21(2): p. 481-488.
65) Kara et al., Biotechnology and bioengineering, 2008. 100(2): p. 231-239.
66) Karlsson et al., Clinical Oral Implants Research, 1998. 9(4): p. 235-242.
67) Katz et al., Angew Chem Int Edit 2004, 43 (45), 6042-6108.
68) Kilpadi et al., Journal of biomedical materials research, 1998. 40(4): p. 646-659.
69) Klammert et al., Acta Biomater. 2011, 7 (9), 3469-3475.
70) Koski et al., ACS Nano 2013, 7 (5), 3739-3743.
71) Lang et al., International Journal of Oral and Maxillofacial Implants, 2004. 19(SUPPL.): p. 150-154.
72) Lee et al., Small 2005, 1 (7), 744-753.
73) LeGeros, Chem. Rev. 2008, 108 (11), 4742-4753.
74) Li et al., Angew Chem Int Edit 2004, 43 (39), 5238-5242.
75) Lindhe et al., Journal of clinical periodontology, 2008. 35(s8): p. 282-285.
76) Ma et al., Adv Mater 2010, 22 (45), 5082-5104.
77) Ma et al., J Phys Chem B 2004, 108 (7), 2115-2119.
78) Ma et al., Nano Lett. 2015, 15 (1), 127-33.
79) Maazouz et al., J Mater Chem B 2014, 2 (33) 5378-5386.
80) Matarasso et al., Clinical oral implants research, 1996. 7(1): p. 64-72.
81) Matono et al., Dental materials journal, 2006. 25(1): p. 104-112.
82) Mayes, International journal of cosmetic science 1979, 1, 329-340.
83) Mdleleni et al., J Am Chem Soc 1998, 120 (24), 6189-6190.
84) Mewis et al., Adv. Colloid Interfac. 2009, 147-48, 214-227.
85) Milošev et al., Acta Chimica Slovenica, 2013. 60(3): p. 543-555.
86) Moore et al., Biomaterials 2010, 31 (7), 1604-1611.
87) Nakagawa et al., Dental materials journal, 2002. 21(2): p. 83-92.
88) NIST XPS Database. Principal Photoelectron Lines Result. Available at http://srdata.nist.gov/xps. 2003.
89) Novoselov et al., Nature 2005, 438 (7065), 197-200.
90) Novoselov et al., Science 2004, 306 (5696), 666-669.
91) Ostrowski et al., ACS Biomater. Sci. Eng. 2015, 1, 52-63.
92) Paineau et al., Langmuir 2011, 27 (12), 7806-7819.
93) Paineau et al., Langmuir 2011, 27 (9), 5562-5573.
94) Pang et al., Chem Commun 2011, 47 (22), 6317-6319.
95) Paolella et al., Nano Lett 2014, 14 (12), 6828-6835.
96) Park et al., Journal of Craniofacial Surgery, 2012. 23(5): p. 1552-1558.
97) Park et al., Journal of periodontology, 2013. 84(8): p. 1191-1198.
98) Pastero et al., Cryst. Growth Des. 2004, 4 (3), 485-490.
99) Paterson et al., X-ray photoelectron spectroscopy, in Clay Mineralogy: Spectroscopic and Chemical Determinative Methods. 1994, Springer. p. 226-259.
100) Pfaffl, Nucleic Acids Res. 2001, 29(9); e45.
101) Rapley et al., International Journal of Oral & Maxillofacial Implants 1989, 5, 47-52.
102) Reffitt et al., Bone 2003, 32 (2), 127-135.
103) Renvert et al., Journal of Clinical Periodontology, 2008. 35(s8): p. 305-315.
104) Rimondini et al., Int. J. Oral Maxillofac. Implants 2002, 17, 793-798.
105) Rui et al., Acs Nano 2013, 7 (6), 5637-5646.
106) Rupf et al PloS one, 2011. 6(10): p. e25893.
107) Sanchez et al., Dent. Mater. 2014, 30, 1161-1171.
108) Sanchez et al., J. Periodontal Res. 2013, 48, 213-220.
109) Santalucia, J., et al., Improved dental abrasive. 1999, Patent publication number CA2322329 A1
110) Schemehorn et al., J. Clin. Dent. 2011, 22, 11-18.
111) Schmage et al., Int J Oral Maxillofac Implants, 2014. 29(2): p. 331-7.
112) Schmidlin et al., J Appl. Oral Sci. 2013, 21, 48-55.
113) Schmidt et al., Nature 2001, 410 (6825), 168-168.
114) Scofield, J. Electron. Spectrosc. 1976, 8, 129.
115) Shirley, Phys. Rev. B 1972, 5, 4709.
116) Siirils and K6n6nen, International Journal of Oral & Maxillofacial Implants 1990, 6, 50-54.
117) Somturk et al., Dalton Trans 2015 (44): p. 13845-13852.
118) Stajer et al., Journal of Biomedical Materials Research Part A, 2008. 87(2): p. 450-458.
119) St-Arnaud, The Journal of steroid biochemistry and molecular biology 121, 254-256 (2010).
120) Stiller et al., Biomaterials 2014, 35 (10), 3154-63.
121) Stovell et al., International Dental Journal, 2013. 63: p. 57-63.
122) Stratakis et al., Chem Rev 2012, 112 (8), 4469-506.
123) Suslick et al., Nature 1991, 353 (6343), 414-416.
124) Tamimi et al., Acta Biomater. 2011, 7 (6), 2678-2685.
125) Tamimi et al., Acta Biomater. 2012, 8 (2), 474-487.
126) Tamimi, et al., Acta Biomater. 2008, 4 (5), 1315-1321.
127) Tang et al., J. Am. Chem. Soc. 2014, 136 (46), 16357-16367.
128) Tellefsen et al., International Journal of Dental Hygiene, 2011. 9(4): p. 284-290.
129) Thomson-Neal et al., Int. J. Periodontics Restorative Dent. 1989, 9, 300-311.

130) Tibbitt et al., Biotechnol. Bioeng. 2009, 103 (4), 655-663.
131) Trpkovska et al., J. Mol. Struct. 1999, 481, 661-666.
132) Truong et al., Sci Rep-Uk 2014, 4.
133) US Patent Publication no. 2015/0150973.
134) Vali et al., J. Colloid Interf. Sci. 1988, 126 (1) 278-291.
135) Vali et al., J. Microsc. 1986, 141, 361.
136) Wang et al., Bone Res. 2014, 2
137) Wang et al., Chem. Rev. 2008, 108 (11), 4628-4669.
138) Wang et al., Chem. Rev. 2014, 114 (19), 9455-9486.
139) Wang et al., Nano Lett 2012, 12 (11), 5632-5636.
140) Wang et al., Nature 2010, 463 (7279), 339-343.
141) Wegst et al., Nat. Mater. 2015, 14 (1), 23-36.
142) Wu et al., Nat. Commun. 2013, 4, doi: 10.1038/ncomms3431.
143) Xavier et al., ACS nano, 2015. 9(3): p. 3109-3118.
144) Xu et al., Chem. Rev. 2013, 113 (5), 3766-3798.
145) Yasuda, Journal of pain research 6, 161 (2013).
146) Zaccone et al., J. Phys. Chem. B 2008, 112 (22), 6793-6802.
147) Zhang et al., Nature 2005, 438 (7065), 201-204.
148) Zhao et al., Nano Lett 2014, 14 (5) 2849-2853.

The invention claimed is:

1. A pharmaceutical composition comprising one or more bioactive agents and a hydrogel as a carrier for the bioactive agents,
wherein said hydrogel comprises at least 1% v/v of a colloidal suspension of $M^I_X M^{II}_Y P_Z$ two-dimensional nanocrystals in water, wherein:
$M^I$ is $Na^+$ and/or $Li^+$,
$M^{II}$ is $Mg^{2+}$ or a mixture of $Mg^{2+}$ with one or more $Ni^{2+}$, $Zn^{2+}$, $Cu^{2+}$, $Fe^{2+}$ and/or $Mn^{2+}$,
P is a mixture of dibasic phosphate ions ($HPO_4^{2-}$) and tribasic phosphate ions ($P_4^{3-}$),
X ranges from 0.43 to 0.60,
Y ranges from 0.10 to 0.18, and
Z ranges from 0.29 to 0.46,
X, Y, Z being mole fraction.

2. The pharmaceutical composition of claim 1 being an implant.

3. The pharmaceutical composition of claim 1 being an injectable.

4. The pharmaceutical composition of claim 1, wherein the bioactive agent is selected from the group consisting of local anaesthetic, antibiotics and beta blockers.

5. A method of targeting delivery of a bioactive agent to a site of need of a patient, the method comprising the steps of administering the pharmaceutical composition of claim 1 to the site of need.

6. The method of claim 5, wherein the site of need is a bone defect or a bone injury.

7. The method of claim 5, wherein said administering step comprises implanting the pharmaceutical composition.

8. The method of claim 5, wherein said administering step comprises injecting the pharmaceutical composition.

9. A paste for cleaning a dental implant, the paste comprising a hydrogel mixed with an abrasive agent,
wherein said hydrogel comprises at least 1% v/v of a colloidal suspension of $M^I_X M^{II}_Y P_Z$ two-dimensional nanocrystals in water, wherein:
$M^I$ is $Na^+$ and/or $Li^+$,
$M^{II}$ is $Mg^{2+}$ or a mixture of $Mg^{2+}$ with one or more $Ni^{2+}$, $Zn^{2+}$, $Cu^{2+}$, $Fe^{2+}$ and/or $Mn^{2+}$,
P is a mixture of dibasic phosphate ions ($HPO_4^{2-}$) and tribasic phosphate ions ($P_4^{3-}$),
X ranges from 0.43 to 0.60,
Y ranges from 0.11 to 0.18, and
Z ranges from 0.29 to 0.46,
X, Y, Z being mole fractions.

10. The paste of claim 9, wherein the hydrogel has a pH between about 9 and about 10.

11. The paste of claim 9, wherein $M^I$ is $Na^+$, $M^{II}$ is $Mg^{2+}$, X is 0.50, Y is 0.13, and Z is 0.37.

12. The paste of claim 9, wherein the abrasive agent is a silica.

13. The paste of claim 9, wherein the abrasive agent is hydrated silica nanoparticles.

14. The paste of claim 9, wherein the abrasive agent particles have a particles size up to about 500 nm.

15. The paste of claim 9, comprising from about 5 to about 60% by weight of the abrasive agent, based on the total weight of the paste.

16. The paste of claim 9, further comprising one or more additives.

17. The paste of claim 9, wherein the abrasive agent is selected from the group consisting of magnesium phosphate silica, a nano-silicate and calcium carbonate.

18. The paste of claim 9, wherein the abrasive agent particles have a particles size up to about 400 nm.

19. The paste of claim 9, comprising from about 20% to about 40%, by weight of the abrasive agent, based on the total weight of the paste.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: chemically synthesized

<400> SEQUENCE: 1
ggcttgggtt tcaggttag                                                   19

<210> SEQ ID NO 2
<211> LENGTH: 20
<212> TYPE: DNA
<213> ORGANISM: Artificial Sequence
<220> FEATURE:
<223> OTHER INFORMATION: chemically synthesized

<400> SEQUENCE: 2
cggtttctta gggtcttgga                                                  20

<210> SEQ ID NO 3
<211> LENGTH: 20
<212> TYPE: DNA
<213> ORGANISM: Artificial Sequence
<220> FEATURE:
<223> OTHER INFORMATION: chemically synthesized

<400> SEQUENCE: 3
ggggacatgc agtatgagtt                                                  20

<210> SEQ ID NO 4
<211> LENGTH: 20
<212> TYPE: DNA
<213> ORGANISM: Artificial Sequence
<220> FEATURE:
<223> OTHER INFORMATION: chemically synthesized

<400> SEQUENCE: 4
ggcctggtag ttgttgtgag                                                  20

<210> SEQ ID NO 5
<211> LENGTH: 22
<212> TYPE: DNA
<213> ORGANISM: Artificial Sequence
<220> FEATURE:
<223> OTHER INFORMATION: chemically synthesized

<400> SEQUENCE: 5
gaggcataaa gggtcatcgt gg                                               22

<210> SEQ ID NO 6
```

```
<211> LENGTH: 22
<212> TYPE: DNA
<213> ORGANISM: Artificial Sequence
<220> FEATURE:
<223> OTHER INFORMATION: chemically synthesized

<400> SEQUENCE: 6
cattaggcgc aggaaggtca gc                                          22

<210> SEQ ID NO 7
<211> LENGTH: 16
<212> TYPE: DNA
<213> ORGANISM: Artificial Sequence
<220> FEATURE:
<223> OTHER INFORMATION: chemically synthesized

<400> SEQUENCE: 7
tgaacagact ccggcg                                                 16

<210> SEQ ID NO 8
<211> LENGTH: 19
<212> TYPE: DNA
<213> ORGANISM: Artificial Sequence
<220> FEATURE:
<223> OTHER INFORMATION: chemically synthesized

<400> SEQUENCE: 8
gataccgtag atgcgtttg                                              19

<210> SEQ ID NO 9
<211> LENGTH: 21
<212> TYPE: DNA
<213> ORGANISM: Artificial Sequence
<220> FEATURE:
<223> OTHER INFORMATION: chemically synthesized

<400> SEQUENCE: 9
ctgctagtac acaagcagac a                                           21

<210> SEQ ID NO 10
<211> LENGTH: 22
<212> TYPE: DNA
<213> ORGANISM: Artificial Sequence
<220> FEATURE:
<223> OTHER INFORMATION: chemically synthesized

<400> SEQUENCE: 10
catgagaaat tcggaatttc ag                                          22
```